US012340916B2

(12) United States Patent
Kelly

(10) Patent No.: US 12,340,916 B2
(45) Date of Patent: *Jun. 24, 2025

(54) MATERIALS AND PROCESSES FOR GENERATING RADIOISOTOPES

(71) Applicant: AdvanCell Isotopes Pty Limited, Sydney (AU)

(72) Inventor: Julian Frederick Kelly, North Adelaide (AU)

(73) Assignee: AdvanCell Isotopes Pty Limited, Sydney (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/618,251

(22) Filed: Mar. 27, 2024

(65) Prior Publication Data

US 2024/0339236 A1   Oct. 10, 2024

Related U.S. Application Data

(63) Continuation of application No. 18/685,737, filed as application No. PCT/AU2022/050958 on Aug. 23, 2022.

(30) Foreign Application Priority Data

Aug. 23, 2021 (AU) .................. 2021902649

(51) Int. Cl.
*G21G 4/08* (2006.01)
*A61K 51/12* (2006.01)
(Continued)

(52) U.S. Cl.
CPC ............ *G21G 4/08* (2013.01); *A61K 51/1289* (2013.01); *C04B 35/495* (2013.01);
(Continued)

(58) Field of Classification Search
None
See application file for complete search history.

(56) References Cited

U.S. PATENT DOCUMENTS 3,453,196 A * 7/1969 Sporek ............... G21G 4/04
250/493.1
4,058,485 A * 11/1977 Cheung ............. B01J 37/0009
502/355
(Continued)

FOREIGN PATENT DOCUMENTS

EP 0466290 A1 1/1992
EP 2125620 B1 8/2013
(Continued)

OTHER PUBLICATIONS

"Secret lives of two elements uncovered by Sandia researchers"; "Secret lives of two elements uncovered by Sandia researchers"; Newd Release; Oct. 22, 2007; https://newsreleases.sandia.gov/releases/2007/secretlives.html (Year: 2007).*
(Continued)

*Primary Examiner* — David Sample
(74) *Attorney, Agent, or Firm* — DLA Piper LLP

(57) ABSTRACT

The present disclosure generally relates to materials, processes, generators, and/or systems, for generating radioisotope. The present disclosure also generally relates to ceramic materials comprising radioisotope suitable for use in a radioisotope generator. The present disclosure also generally relates to processes, generators and/or systems, for producing and capturing radioisotope. The present disclosure also generally relates to the preparation of radioisotope solutions for use in radiopharmacy and/or other clinical applications.

22 Claims, 19 Drawing Sheets

(51) Int. Cl.
  *A61N 5/10* (2006.01)
  *C04B 35/495* (2006.01)
  *C04B 41/45* (2006.01)
  *C04B 41/50* (2006.01)
  *C04B 41/87* (2006.01)
  *G21G 1/00* (2006.01)

(52) U.S. Cl.
  CPC ...... *C04B 41/4535* (2013.01); *C04B 41/4558* (2013.01); *C04B 41/5045* (2013.01); *C04B 41/87* (2013.01); *A61N 5/1001* (2013.01); *G21G 2001/0094* (2013.01)

(56) References Cited

U.S. PATENT DOCUMENTS

| | | | |
|---|---|---|---|
| 4,663,129 A | 5/1987 | Atcher et al. | |
| 12,249,439 B2 | 3/2025 | Kelly | |
| 2004/0186340 A1 | 9/2004 | Reed et al. | |
| 2006/0153760 A1 | 7/2006 | Meikrantz et al. | |
| 2015/0348661 A1 | 12/2015 | Wagh | |
| 2018/0047474 A1* | 2/2018 | O'Hara | C01B 23/0073 |
| 2019/0066860 A1* | 2/2019 | Jernström | G21G 4/10 |

FOREIGN PATENT DOCUMENTS

| | | |
|---|---|---|
| GB | 1168037 | 10/1969 |
| JP | 2011192740 A | 9/2011 |
| RU | 2746985 C1 | 4/2021 |
| WO | 2002034299 A1 | 5/2002 |
| WO | 2013174949 A1 | 11/2013 |
| WO | 2014063198 A1 | 5/2014 |
| WO | 2017093069 A1 | 6/2017 |
| WO | 2018007643 A1 | 1/2018 |
| WO | 2021078954 A1 | 4/2021 |
| WO | WO-2021110950 A1 * | 6/2021 ............. G21F 5/015 |

OTHER PUBLICATIONS

"Enabling next-generation precision cancer therapy investor presentation"; Thor Medical presentation; Jun. 11, 2024 (as evidence only); (Year: 2024).*
Hassfjell et al. "A 212Pb generator based on a 228Th source", 2000, Appl. Radiat. Isot. 55(2001):433-439.
Australia Patent Office Article 15(5) Request Search Statement dated Dec. 3, 2021.
Further Written Opinion for PCT Application No. PCT/AU2022/050958 mailed Aug. 10, 2023.
International Preliminary Report on Patentability for Application No. PCT/AU2022/050958 mailed Nov. 27, 2023.
Written Opinion for PCT Application No. PCT/AU2022/050958 mailed Oct. 14, 2022.
Yong et al. "Towards Translation of 212Pb as a clinical therapeutic; getting the lead in!" 2011, Dalton Trans. 40:6068-6076.
Hassfjell et al. "A Generator for Production of 212Pb and 212Bi", 1994, Appl. Radiat. Isot. 45(10):1021-1025.

* cited by examiner

MATERIALS AND PROCESSES FOR GENERATING RADIOISOTOPES

CROSS REFERENCE TO RELATED APPLICATIONS

This application is a continuation of U.S. patent application Ser. No. 18/685,737, filed Feb. 22, 2024, which is a U.S. National Stage filing under 35 U.S.C. § 371 of International PCT Application No. PCT/AU2022/050958, filed Aug. 23, 2022, which claims the benefit of priority to Australian Application No. 2021902649, titled "Materials and Processes for Generating Radioisotopes," filed Aug. 23, 2021, each of which is incorporated herein by reference in its entirety.

FIELD

The present disclosure generally relates to materials, processes, generators, and/or systems, for generating radioisotope. The present disclosure also generally relates to ceramic materials comprising radioisotope suitable for use in a radioisotope generator. The present disclosure also generally relates to processes, generators and/or systems, for producing and capturing radioisotope. The present disclosure also generally relates to the preparation of radioisotope solutions for use in radiopharmacy and/or other clinical applications.

BACKGROUND

Radioisotopes have a variety of uses including, for example, in medical applications as radiopharmaceuticals in which radioisotopes can effectively deliver lethal radiation directly to cancer cells with little collateral damage to surrounding healthy tissue. However, clinical uptake of this form of therapy is restricted by the availability of suitable radioisotopes and global supply is limited due to various manufacturing constraints, with the current supply of alpha-emitting radioisotope worldwide being only enough to treat around 2000 patients yearly. Moreover, radioisotopes generated by current methods are often contaminated with impurities, including radiochemical impurities, which are difficult to filter or remove from the desired radioisotope, which can hinder clinical application.

A small number of radioisotopes are produced for therapeutic/clinical trial use, for example, lutetium-177 ($^{177}$Lu) and actinium-225 ($^{225}$Ac) which can both be labelled to cancer targeting molecules. However, generating these isotopes in clinically useful amounts requires complex operations, including for example large particle accelerators or nuclear reactors. The supply chains for these radioisotopes are therefore unwieldy, expensive and consequently are limited to just a few manufacturing facilities worldwide.

Lead-212 ($^{212}$Pb) is an excellent alpha-emitting radioisotope for radioligand therapy. Current generators for producing lead-212 ($^{212}$Pb) are column based generators that employ parent radioisotope having relatively short half-life e.g. radium-224 ($^{224}$Ra), which elute $^{212}$Pb from parent radioisotope bound on resin-based ion exchange materials or on inorganic sorbent salts. Such resin-based ion exchange and inorganic sorbent based generators can be subject to significant radiolytic damage which limits their overall durability and limits their clinical application. Furthermore, the extraction of the isolated $^{212}$Pb radioisotope from such resin-based ion exchange and sorbent based generators often requires significant amount of wash fluid thus complicating and lengthening subsequent radiolabelling chemistry processes. Additionally, most $^{212}$Pb generators experience significant yield decrease over time due to radiolytic breakdown of the organic material, such as barium stearate, used to immobilise and house the parent radioisotope and/or require overly complex loading procedures for immobilising the parent radioisotope which can expose users to significant radiation doses.

Accordingly, there is a need for improved materials and processes for generating therapeutic radioisotopes, which can allow for the production of clinically useful doses of therapeutic isotope.

SUMMARY

The present inventors have undertaken research and development into materials and processes for the generation of radioisotopes.

In particular, the present inventors have developed ceramic materials that can be configured to immobilise a radioisotope which can be used as a source for generating a daughter radioisotope. The present inventors have identified that immobilising the parent radioisotope on or within a ceramic material allowed for the effective separation of the gaseous intermediate radioisotope as it decayed and emanated away from the immobilised parent radioisotope, thereby providing downstream advantages including for example reduced contamination of the daughter radioisotope with the parent radioisotope.

In one aspect, there is provided an inert ceramic substrate comprising parent radioisotope immobilised on or within the inert ceramic substrate in an amount effective to generate a medically useful dose of daughter radioisotope through a chain of spontaneous decay from the parent radioisotope via a gaseous intermediate radioisotope, wherein at least some of the immobilised parent radioisotope is bound on or near the surface of the inert ceramic substrate as a radioisotope surface layer to allow for effective emanation of the gaseous intermediate radioisotope away from the inert ceramic substrate.

In another aspect, there is provided a process for preparing an inert ceramic substrate comprising parent radioisotope immobilised on or within the inert ceramic substrate in an amount effective to generate a medically useful dose of daughter radioisotope through a chain of spontaneous decay from the parent radioisotope via a gaseous intermediate radioisotope, the process comprising the steps of: a) depositing a solution comprising a parent radioisotope species on the surface of an inert ceramic substrate; b) heating the inert ceramic substrate to a temperature effective to bind at least some of the parent radioisotope on or near the surface of the inert ceramic substrate forming a heat-treated radioisotope surface layer to allow for effective emanation of the gaseous daughter radioisotope away from the inert ceramic substrate.

The present inventors have also developed a radioisotope generator and system for capturing a population of daughter radioisotope. The radioisotope generator can be configured to house an inert ceramic substrate described herein. According to some embodiments or examples described herein, the effective emanation of gaseous intermediate radioisotope away from the parent radioisotope which is immobilised within the inert ceramic substrate described herein enabled the development of a radioisotope generator that allowed for "line-of-sight" gravity assisted collection of daughter radioisotope with minimal contamination In another aspect, there is provided a radioisotope generator defining a chamber for capturing a population of daughter radioisotope, the chamber configured to house an inert ceramic substrate as described herein in the chamber. In another aspect, there is provided a system for producing and capturing a population of daughter radioisotope, the system: a) a radioisotope generator defining a chamber for capturing a population of daughter radioisotope; and b) an inert ceramic substrate as described herein housed in the chamber. The system may comprise a radioisotope generator as described herein.

The present inventors have also developed a process for capturing a population of daughter radioisotope. In another aspect, there is provided process for capturing a population of daughter radioisotope comprising: a) allowing for the emanation of a gaseous intermediate radioisotope generated through a chain of spontaneous decay from a parent radioisotope immobilised on or within an inert ceramic substrate described herein; and b) collecting at least some of the gaseous intermediate radioisotope for a period of time effective to decay into a daughter radioisotope. The process may comprise a radioisotope generator or system as described herein.

Other aspects and embodiments relating to the present disclosure are described herein. It will be appreciated that each example, aspect and embodiment of the present disclosure described herein is to be applied mutatis mutandis to each and every other example, aspect or embodiment unless specifically stated otherwise. For example, each example, aspect and embodiment of the inert ceramic substrate described herein may apply equally to one or more of the generator, system or process described herein, and vice versa. The present disclosure is not to be limited in scope by the specific examples described herein, which are intended for the purpose of exemplification only.

Functionally-equivalent products, compositions and processes are clearly within the scope of the disclosure as described herein.

BRIEF DESCRIPTION OF DRAWINGS

Embodiments of the present disclosure are further described and illustrated as follows, by way of example only, with reference to the accompanying drawings in which.

DETAILED DESCRIPTION

Figure 1:
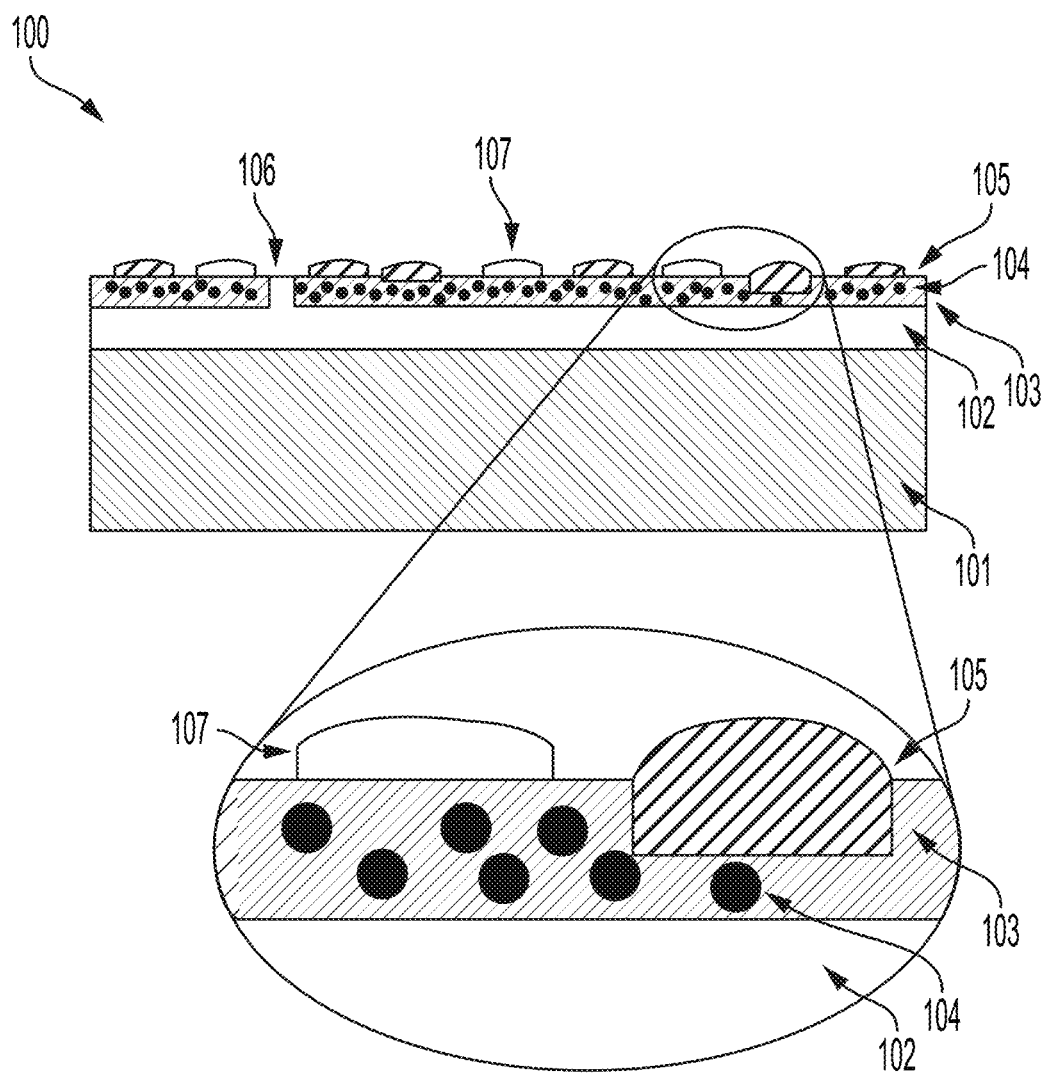
FIG. 1 shows a schematic of one embodiment of an inert ceramic substrate comprising immobilised radioisotope.

The present disclosure describes the following various non-limiting embodiments, which relate to investigations undertaken to develop materials, processes, generators, devices, and/or systems, for generating radioisotope. It was surprisingly found that a scalable process and generator could be provided to reliably produce daughter radioisotope.

Terms

In the following description, reference is made to the accompanying drawings which form a part hereof, and which is shown, by way of illustration, several embodiments. It is understood that other embodiments may be utilized and structural changes may be made without departing from the scope of the present disclosure.

With regards to the definitions provided herein, unless stated otherwise, or implicit from context, the defined terms and phrases include the provided meanings. Unless explicitly stated otherwise, or apparent from context, the terms and phrases below do not exclude the meaning that the term or phrase has acquired by a person skilled in the relevant art. The definitions are provided to aid in describing particular embodiments, and are not intended to limit the claimed invention, because the scope of the invention is limited only by the claims. Furthermore, unless otherwise required by context, singular terms shall include pluralities and plural terms shall include the singular.

All publications discussed and/or referenced herein are incorporated herein in their entirety.

Any discussion of documents, acts, materials, devices, articles or the like which has been included in the present specification is solely for the purpose of providing a context for the present disclosure. It is not to be taken as an admission that any or all of these matters form part of the prior art base or were common general knowledge in the field relevant to the present disclosure as it existed before the priority date of each claim of this application.

Throughout this disclosure, unless specifically stated otherwise or the context requires otherwise, reference to a single step, composition of matter, group of steps or group of compositions of matter shall be taken to encompass one and a plurality (i.e., one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth.

Those skilled in the art will appreciate that the disclosure herein is susceptible to variations and modifications other than those specifically described. It is to be understood that the disclosure includes all such variations and modifications. The disclosure also includes all of the examples, steps, features, methods, compositions, coatings, processes, and coated substrates, referred to or indicated in this specification, individually or collectively, and any and all combinations or any two or more of said steps or features.

In describing examples and embodiments, herein, specific terminology is used for the sake of clarity. For the purpose of description, specific terms are intended to at least include technical and functional equivalents that operate in a similar manner to accomplish a similar result. Additionally, in some instances where a particular embodiment or example includes a plurality of system elements or method steps, those elements or steps may be replaced with a single element or step. Likewise, a single element or step may be replaced with a plurality of elements or steps that serve the same purpose.

The term "and/or", e.g., "X and/or Y" shall be understood to mean either "X and Y" or "X or Y" and shall be taken to provide explicit support for both meanings or for either meaning.

Unless otherwise indicated, the terms "first," "second," etc. are used herein merely as labels, and are not intended to impose ordinal, positional, or hierarchical requirements on the items to which these terms refer. Moreover, reference to a "second" item does not require or preclude the existence of lower-numbered item (e.g., a "first" item) and/or a higher-numbered item (e.g., a "third" item).

Where methods/processes are recited and where steps/stages are recited in a particular order—with or without sequenced prefacing characters added for ease of reference—the steps/stages are not to be interpreted as being temporally limited to the order in which they are recited unless otherwise specified or implied by the terms and phrasing.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example and without limitation, two of item A, one of item B, and ten of item C; four of item B and seven of item C; or some other suitable combination.

As used herein, the term "about", unless stated to the contrary, typically refers to +/−10%, for example +/−5%, of the designated value.

Where parameters for various properties or other values are specified herein for examples or embodiments, those parameters or values can be adjusted up or down by $1/100$th, $1/50$th, $1/20$th, $1/10$th, $1/5$th, $1/3$rd, $1/2$, $2/3$rd, $3/4$th, $4/5$th, $9/10$th, $19/20$th, $49/50$th, $99/100$th, etc. (or up by a factor of 1, 2, 3, 4, 5, 6, 8, 10, 20, 50, 100, etc.), or by rounded-off approximations thereof or within a range of the specified parameter up to or down to any of the variations specified above (e.g., for a specified parameter of 100 and a variation of $1/100$th, the value of the parameter may be in a range from 0.99 to 1.01), unless otherwise specified.

It is to be appreciated that certain features that are, for clarity, described herein in the context of separate embodiments, may also be provided in combination in a single embodiment. Conversely, various features that are, for brevity, described in the context of a single embodiment, may also be provided separately or in any sub-combination.

Throughout the present specification, various aspects and components of the invention can be presented in a range format. The range format is included for convenience and should not be interpreted as an inflexible limitation on the scope of the invention. Accordingly, the description of a range should be considered to have specifically disclosed all the possible sub-ranges as well as individual numerical values within that range, unless specifically indicated. For example, description of a range such as from 1 to 5 should be considered to have specifically disclosed sub-ranges such as from 1 to 3, from 1 to 4, from 1 to 5, from 2 to 4, from 2 to 5, from 3 to 5 etc., as well as individual and partial numbers within the recited range, for example, 1, 2, 3, 4, 4.5 and 5, unless where integers are required or implicit from context. This applies regardless of the breadth of the disclosed range. Where specific values are required, these will be indicated in the specification.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps. The phrase "consisting of means the enumerated elements and no others.

As used herein, the term "decay" refers to the spontaneous transformation of a radioactive nuclide into a different nuclide referred to as its daughter, or its "decay product". The daughter nuclide may be stable or it may itself be radioactive and will thus undergo further spontaneous decay into a different daughter nuclide. It is understood that these radioactive decay processes occur spontaneously without the need for human intervention.

Ceramic Substrates for Immobilising Radioisotope

The present inventors have developed ceramic materials that can be configured to immobilise a radioisotope. The radioisotope can be a parent radioisotope that is the parent for one or more useful daughter radioisotopes, including those provided in the decay series in FIG. 2, such as $^{212}$Pb. The parent radioisotope can be used as a source for a gaseous intermediate radioisotope which can be captured and used in turn as a source for generating a daughter radioisotope using the processes and generators described herein.

According to at least some embodiments or examples described herein, it was found that immobilising the parent radioisotope on or within a ceramic material allowed for the effective separation of the gaseous intermediate radioisotope as it emanated away from the immobilised parent radioisotope, thereby providing downstream advantages including for example reduced contamination of the daughter radioisotope with the parent radioisotope. In one embodiment, there is provided an inert ceramic substrate comprising parent radioisotope immobilised on or within the inert ceramic substrate, for example on or within the surface of the inert ceramic substrate.

In one embodiment or example, there is provided an inert ceramic substrate comprising parent radioisotope immobilised on or within the inert ceramic substrate.

In one embodiment or example, there is provided an inert ceramic substrate comprising parent radioisotope immobilised on or within the inert ceramic, wherein at least some of the immobilised parent radioisotope is bound on or near the surface of the inert ceramic substrate as a radioisotope surface layer to allow for effective emanation of gaseous intermediate radioisotope away from the inert ceramic substrate.

In one embodiment or example, the inert ceramic substrate comprises parent radioisotope immobilised on or within the inert ceramic substrate in an amount effective to generate a medically useful dose of daughter radioisotope through a chain of spontaneous decay from the parent radioisotope via a gaseous intermediate radioisotope, wherein at least some of the immobilised parent radioisotope is bound on or near the surface of the inert ceramic substrate as a radioisotope surface layer to allow for effective emanation of the gaseous intermediate radioisotope away from the inert ceramic substrate.

In another embodiment or example, there is provided an inert ceramic substrate comprising parent radioisotope immobilised on or within the inert ceramic substrate, wherein at least some of the immobilised parent radioisotope is bound on or near the surface of the inert ceramic substrate as a heat-treated radioisotope surface layer to allow for effective emanation of gaseous intermediate radioisotope away from the inert ceramic substrate.

In another embodiment or example, there is provided an inert ceramic substrate comprising parent radioisotope immobilised on or within the inert ceramic substrate in an amount effective to generate a medically useful dose of daughter radioisotope through a chain of spontaneous decay from the parent radioisotope via a gaseous intermediate radioisotope, wherein at least some of the immobilised parent radioisotope is bound on or near the surface of the inert ceramic substrate as a heat-treated radioisotope surface layer to allow for effective emanation of the gaseous intermediate radioisotope away from the inert ceramic substrate.

In another embodiment or example, there is provided an inert ceramic substrate comprising parent radioisotope immobilised on or within the inert ceramic substrate, wherein at least some of the immobilised parent radioisotope is bound on or near the surface of the inert ceramic substrate as a radioisotope surface layer having a thickness of between about 0.1 nm to about 1,000 nm to allow for effective emanation of gaseous intermediate radioisotope away from the inert ceramic substrate.

In another embodiment or example, there is provided an inert ceramic substrate comprising parent radioisotope immobilised on or within the inert ceramic substrate in an amount effective to generate a medically useful dose of daughter radioisotope through a chain of spontaneous decay from the parent radioisotope via a gaseous intermediate radioisotope, wherein at least some of the immobilised parent radioisotope is bound on or near the surface of the inert ceramic substrate as a radioisotope surface layer having a thickness of between about 0.1 nm to about 1,000 nm to allow for effective emanation of the gaseous intermediate radioisotope away from the inert ceramic substrate.

In another embodiment or example, there is provided an inert ceramic substrate comprising parent radioisotope immobilised on or within the inert ceramic substrate, wherein at least some of the immobilised parent radioisotope is bound on or near the surface of the inert ceramic substrate as a radioisotope surface layer to allow for effective emanation of the gaseous intermediate radioisotope away from the inert ceramic substrate, wherein the inert ceramic substrate has a porosity (vol. % based on the total volume of the inert ceramic substrate) of less than about 10, 5, 2, 1, 0.1, or 0.01.

In another embodiment or example, there is provided an inert ceramic substrate comprising parent radioisotope immobilised on or within the inert ceramic substrate in an amount effective to generate a medically useful dose of daughter radioisotope through a chain of spontaneous decay from the parent radioisotope via a gaseous intermediate radioisotope, wherein at least some of the immobilised parent radioisotope is bound on or near the surface of the inert ceramic substrate as a radioisotope surface layer to allow for effective emanation of the gaseous intermediate radioisotope away from the inert ceramic substrate, wherein the inert ceramic substrate has a porosity (vol. % based on the total volume of the inert ceramic substrate) of less than about 10, 5, 2, 1, 0.1, or 0.01.

In another embodiment or example, there is provided a metal oxide substrate comprising parent radioisotope immobilised on or within the metal oxide substrate, wherein at least some of the immobilised parent radioisotope is bound on or near the surface of the metal oxide substrate as a radioisotope surface layer to allow for effective emanation of gaseous intermediate radioisotope away from the inert ceramic substrate.

In another embodiment or example, there is provided a metal oxide substrate comprising parent radioisotope immobilised on or within the metal oxide substrate in an amount effective to generate a medically useful dose of daughter radioisotope through a chain of spontaneous decay from the parent radioisotope via a gaseous intermediate radioisotope, wherein at least some of the immobilised parent radioisotope is bound on or near the surface of the metal oxide substrate as a radioisotope surface layer to allow for effective emanation of the gaseous intermediate radioisotope away from the inert ceramic substrate.

In another embodiment or example, there is provided a metal oxide substrate comprising parent radioisotope immobilised on or within the metal oxide substrate, wherein at least some of the immobilised parent radioisotope is bound on or near the surface of the inert ceramic substrate as a radioisotope surface layer to allow for effective emanation of gaseous intermediate radioisotope away from the inert ceramic substrate, wherein the metal oxide substrate is an oxide of tantalum, niobium, tungsten, molybdenum, vanadium, zirconium, titanium or aluminium, or mixed oxides thereof.

In another embodiment or example, there is provided a metal oxide substrate comprising parent radioisotope immobilised on or within the metal oxide substrate in an amount effective to generate a medically useful dose of daughter radioisotope through a chain of spontaneous decay from the parent radioisotope via a gaseous intermediate radioisotope, wherein at least some of the immobilised parent radioisotope is bound on or near the surface of the inert ceramic substrate as a radioisotope surface layer to allow for effective emanation of the gaseous intermediate radioisotope away from the inert ceramic substrate, wherein the metal oxide substrate is an oxide of tantalum, niobium, tungsten, molybdenum, vanadium, zirconium, titanium or aluminium, or mixed oxides thereof.

In one embodiment, at least some of the immobilised parent radioisotope is bound on or near the surface of the inert ceramic substrate as a heat-treated radioisotope surface layer to allow for effective emanation of the gaseous intermediate radioisotope away from the inert ceramic substrate. In one embodiment, at least some of the immobilised parent radioisotope is bound on or near the surface of the inert ceramic substrate as a radioisotope surface layer having a thickness of between about 0.1 nm to about 1000 nm to allow for effective emanation of the gaseous intermediate radioisotope away from the inert ceramic substrate. In one embodiment, the inert ceramic substrate has a porosity (vol. % based on the total volume of the inert ceramic substrate) of less than about 10, 5, 2, 1, 0.1, or 0.01.

Types of Radioisotope

Any suitable parent radioisotope may be used. In one embodiment, the parent radioisotope is an alpha-emitting radioisotope i.e. capable of emitting an alpha particle (i.e. helium nucleus) and thereby transforms into a different atomic nucleus with a mass number that is reduced by four and an atomic number that is reduced by two.

In one embodiment, the parent radioisotope is an isotope of thorium or radium or a combination thereof. In one embodiment, the parent radioisotope is a thorium radioisotope. The thorium radioisotope may be selected from at least one of thorium-227 ($^{227}$Th), thorium-228 ($^{228}$Th), and thorium-232 (232Th), or combination thereof. In one embodiment, the parent radioisotope is radium. The radium radioisotope may be selected from at least one of $^{224}$Ra and $^{228}$Ra, or a combination thereof.

In one embodiment, the parent radioisotope is $^{228}$Th. $^{228}$Th has a half-life of almost two years and is available commercially. These and other properties of $^{228}$Th make it desirable as a parent radioisotope for producing $^{212}$Pb as an alpha-emitting medical isotope. Once immobilised on or within the inert ceramic substrates described herein, according to some embodiments or examples, $^{228}$Th can be used as a parent radioisotope in a $^{212}$Pb generator for a year or more with only gradual loss of productivity. In one embodiment, the gaseous intermediate radioisotope is a radon radioisotope. The radon radioisotope may be selected from at least one of radon-219 ($^{219}$Rn) or radon-220 ($^{220}$Rn). In one embodiment, the daughter radioisotope is a lead radioisotope. The lead radioisotope may be selected from at least one of lead-211 ($^{211}$Pb) or lead-212 ($^{212}$Pb).

In one embodiment, the parent radioisotope are immobilised on or within the inert ceramic substrate in an amount effective to generate a medically useful dose of daughter radioisotope through a chain of spontaneous decay of a gaseous intermediate isotope. As used herein, the term "medically useful" in relation to the dose of daughter radioisotope refers to an amount of daughter radioisotope (e.g $^{212}$Pb) that can be used as a product for radiopharmacy applications such as radioligand therapy. The parent radioisotope may be provided in an amount effective to generate a medically useful amount (e.g. pre-clinically and/or clinically useful amount) of daughter radioisotope. In one embodiment, the parent radioisotope may be immobilised on or within the inert ceramic substrate in an amount effective to generate a medical dose of daughter radioisotope (e.g. $^{212}$Pb) of between about 1 to about 1,000 MBq. In one embodiment, the parent radioisotope may be immobilised on or within the inert ceramic substrate in an amount effective to generate a medical dose of daughter radioisotope (e.g. $^{212}$Pb) of at least about 1, 2, 5, 10, 50, 60, 90, 120, 150, 200, 250, 300, 400, 500, 600, 700, 800, 900 or 1,000 MBq. In another embodiment, the parent radioisotope may be immobilised on or within the inert ceramic substrate in an amount effective to generate a medical dose of daughter radioisotope (e.g. $^{212}$Pb) of less than about 1,000, 900, 800, 700, 600, 500, 400, 300, 250, 200, 150, 120, 90, 60, 50, 10, 5, 2 or 1. In one embodiment, the parent radioisotope may be immobilised on or within the inert ceramic substrate in an amount effective to generate a medical dose of daughter radioisotope (e.g. $^{212}$Pb) of at least about 50, 70, 100, 120, 140, 160, 180 or 200 MBq. The parent radioisotope may be immobilised on or within the inert ceramic substrate in an amount effective to generate a medical dose of daughter radioisotope (e.g. $^{212}$Pb) in a range provided by any two of these upper and/or lower values, for example between about 50 MBq to about 200 MBq.

In one embodiment, the parent radioisotope immobilised on or within the inert ceramic substrate is present in an amount effective to provide an activity (in MBq per $cm^2$ of inert ceramic substrate surface) of between about 1 to about 1500. The parent radioisotope may be immobilised on or within the inert ceramic substrate in an amount effective to provide an activity (in MBq per $cm^2$ of inert ceramic substrate surface) of at least about 0.01, 0.05, 1, 2, 5, 10, 20, 50, 70, 100, 200, 300, 400, 500, 600, 700, 800, 900, 1000, 1200, or 1500. The parent radioisotope may be immobilised on or within the inert ceramic substrate in an amount effective to provide an activity (in MBq per $cm^2$ of inert ceramic substrate surface) of less than about 1500, 1200, 1000, 900, 800, 700, 600, 500, 400, 300, 200, 100, 70, 50, 20, 10, 5, 2, 1, 0.05 or 0.01. The parent radioisotope may be immobilised on or within the inert ceramic substrate in an amount effective to provide an activity in a range provided by any two of these upper and/or lower values, for example between about 100 to about 1500, between about 10 to about 1000, or between about 50 to about 500, for example about 100. The activity of the parent radioisotope ion immobilised on or within the inert ceramic substrate may be measured using a suitable radioactivity measurement apparatus, or by inference from the amount of daughter radioisotope/s collected at a distance from the substrate. Activity can also be obtained via suitable simulation and modelling, in line with the Examples described herein.

Immobilisation of Parent Radioisotope

The radioisotope is immobilised on or within the inert ceramic substrate. In one embodiment, the parent radioisotope is immobilised on or within the surface of the inert ceramic substrate. For example, the parent radioisotope may be fixed/bound onto the inert ceramic substrate. In one embodiment, the inert ceramic substrate comprises parent radioisotope immobilised on or within the inert ceramic substrate. The immobilised parent radioisotope may be interspersed on or within the inert ceramic substrate. The immobilised parent radioisotope may be interspersed within the lattice of the inert ceramic substrate. The immobilised parent radioisotope may comprise radioisotope that is surface bound to the inert ceramic substrate. The parent radioisotope may be incorporated or embedded within the surface of the inert ceramic substrate or may be provided as a layer on the surface of the inert ceramic substrate. By immobilising the parent radioisotope on or within the inert ceramic substrate, for example on or within the surface of the inert ceramic substrate, intermediate daughter radioisotope that is gaseous can emanate and diffuse away from the substrate to provide effective separation of the emanated daughter radioisotope from the immobilised parent radioisotope.

In one embodiment, at least some of the immobilised parent radioisotope is bound on or near the surface of the inert ceramic substrate as a radioisotope surface layer to allow for effective emanation of the gaseous intermediate radioisotope away from the inert ceramic substrate.

In one embodiment, at least some of the immobilised parent radioisotope is bound on or near the surface of the inert ceramic substrate as a heat-treated radioisotope surface layer to allow for effective emanation of the gaseous intermediate radioisotope away from the inert ceramic substrate. As used herein, the term "heat-treated" radioisotope surface layer refers to a portion of the surface of the inert ceramic substrate which has been thermally treated (i.e. heated) to chemically and/or physically bind parent radioisotope on or near the surface. The heat-treated radioisotope surface layer may be obtainable by a process comprising a) depositing a solution comprising a parent radioisotope species on the surface of an inert ceramic substrate; b) heating the inert ceramic substrate to a temperature effective to bind at least some of the parent radioisotope on or near the surface of the inert ceramic substrate, thereby forming a heat-treated radioisotope surface layer to allow for effective emanation of the gaseous daughter radioisotope away from the inert ceramic substrate.

The heat-treated radioisotope surface layer may be obtainable by a process described herein under the section heading "Process for preparing inert ceramic substrate comprising immobilised radioisotope." According to some embodiments or examples described herein, the present inventors have identified that the immobilised parent radioisotope within the heat-treated radioisotope surface layer is tightly bound on or near the surface of the underlying inert ceramic substrate, where such heat treatment can facilitate chemical exchange of the radioisotope within the atomic lattice at or near the surface of the inert ceramic substrate, forming a thin and tightly bound layer of radioisotope on or near the surface of the inert ceramic substrate. Such heat-treatment allows for little to no parent radioisotope co-emanating with the gaseous intermediate radioisotope as the latter emanates away from the inert ceramic substrate. In other words, the parent radioisotope within the heat-treated radioisotope surface layer spontaneously decays into gaseous intermediate radioisotope which emanates away from the tightly bound parent radioisotope on or near the surface of the inert ceramic substrate (i.e. the heat-treated radioisotope surface layer).

In one embodiment, the binding of the immobilised parent radioisotope on or near the surface of the inert ceramic substrate is such that, in use, it enables the capture of a population of daughter radioisotope having a contamination level of parent radioisotope of less than about 5, 2, 1, 0.1, 0.01 or 0.001% expressed in activity terms relative to the activity of the daughter radioisotope. An example of a contaminant is $^{228}$Th in the $^{212}$Pb produced using the inert ceramic substrate. For example, even if the radioisotope surface layer comes into contact with the collection surface (e.g. the inner walls of a collection chamber) within a radioisotope generator, little to no cross-contamination of the parent radioisotope occurs owing to the tightly bound parent radioisotope surface layer.

The radioisotope surface layer may comprise immobilised parent radioisotope which is uniformly distributed within the layer. The radioisotope surface layer may be located anywhere on the surface of the inert ceramic substrate. The radioisotope surface layer may be a continuous layer on the surface of the substrate. Alternatively, the radioisotope surface layer may be non-continuous with respect to the entire inert substrate surface, and may comprise two or more sections, for example where the layer does not uniformly and fully cover the surface of the inert ceramic substrate. It will be appreciated that such non-continuous layer morphology is still considered a surface layer for the purposes of the present disclosure. For example, the immobilised parent radioisotope may be decorated (e.g. interspersed) on or within the surface of the inert ceramic substrate, forming the radioisotope surface layer to allow for effective emanation of the gaseous intermediate radioisotope away from the inert ceramic substrate.

In one embodiment or example, there is provided an inert ceramic substrate comprises parent radioisotope immobilised on or within the inert ceramic substrate, wherein the immobilised parent radioisotope is decorated on or near the surface of the inert ceramic substrate as a radioisotope surface layer to allow for effective emanation of gaseous intermediate radioisotope away from the inert ceramic substrate.

In one embodiment or example, there is provided an inert ceramic substrate comprises parent radioisotope immobilised on or within the inert ceramic substrate in an amount effective to generate a medically useful dose of daughter radioisotope through a chain of spontaneous decay from the parent radioisotope via a gaseous intermediate radioisotope, wherein the immobilised parent radioisotope is decorated on or near the surface of the inert ceramic substrate as a radioisotope surface layer to allow for effective emanation of the gaseous intermediate radioisotope away from the inert ceramic substrate.

In some embodiments, at least some of the immobilised parent radioisotope forming the radioisotope surface layer is provided as a radioisotope-doped layer within the surface of the inert ceramic substrate. In one embodiment, at least some of the immobilised parent radioisotope is bound on or within the atomic lattice of the inert ceramic substrate to form a radioisotope-doped layer within the surface of the inert ceramic substrate.

The radioisotope-doped layer may comprise immobilised parent radioisotope ions which may be uniformly distributed within the layer. The radioisotope-doped layer may be located anywhere within the surface of the inert ceramic substrate. The radioisotope-doped layer may be a continuous layer within the surface of the substrate. Alternatively, the radioisotope-doped layer may be non-continuous with respect to the entire inert substrate surface, and may comprise two or more sections for example where the layer does not uniformly and fully cover the surface of the inert ceramic substrate. The radioisotope-doped layer may comprise radioisotope ions bound to the inert ceramic substrate. In one embodiment, at least some of the immobilised parent radioisotope ions are interspersed within the inert ceramic substrate to form a radioisotope-doped layer on the surface of the inert ceramic substrate. In one embodiment, at least some of the immobilised parent radioisotope ions are interspersed within the atomic lattice of the inert ceramic substrate to form a radioisotope-doped layer on the surface of the inert ceramic substrate. In one embodiment, the radioisotope-doped layer comprises the parent radioisotope surface bound to the inert ceramic substrate. Typically, the parent radioisotope will be distributed such that a concentration gradient exists throughout the radioisotope-doped layer (e.g. throughout the depth of the layer), often mediated by the concentration and/or degree of penetration of the radioisotope from the surface of the inert ceramic substrate. In this example, it will be appreciated that the concentration of parent radioisotope may be higher at the outer surface of the radioisotope-doped layer and decrease across the radioisotope-doped layer as depth into the inert ceramic substrate increases.

In one embodiment, at least some of the immobilised parent radioisotope forming the radioisotope surface layer is provided as one or more solid compound phases of the radioisotope bound on the surface of the inert ceramic substrate. The underlying surface on which the solid compound phases of the radioisotope are bound may comprise the radioisotope-doped layer described herein. The term "solid compound phases" in relation to the radioisotope is understood to mean any solid form in which the radioisotope can stably exist. The solid compound phases may comprise crystalline phases or amorphous phases, or a combination thereof.

In one embodiment, at least some of the solid compound phases of the radioisotope may comprise one or more crystalline phases of the radioisotope bound on the surface of the inert ceramic substrate. The underlying surface on which the crystalline compound phases of the radioisotope are bound may comprise the radioisotope-doped layer described herein. The term "crystalline phase" in relation to the radioisotope is understood to mean radioisotope existing within a microscopic structure forming a crystal lattice that extends in all directions, for example an oxide. For example, immobilised parent radioisotope may assemble into distinct crystal lattices to form the one or more crystalline phases bound on the surface of the inert ceramic substrate. Alternatively, one or more crystalline phases of the radioisotope-ions may be present on the surface, resulting in one or more polycrystalline radioisotope phases i.e. a radioisotope surface layer comprising a plurality of discrete crystalline phases separated by crystalline or amorphous regions of radioisotope-doped ceramic substrate and/or by regions of inert ceramic substrate that do not contain radioisotope (i.e. un-doped regions). In one embodiment, the immobilised parent radioisotope is provided as one or more crystalline phases bound on the surface of the radioisotope-doped layer. The crystalline phases may be uniformly distributed on or within the radioisotope-doped layer, for example at the nanometre scale (for example as observed under a scanning electron microscope). The one or more crystalline phases of parent radioisotope may be bound to the lattice of the inert ceramic substrate.

Alternatively or additionally, at least some of the solid compound phases of radioisotope may be provided as one or more amorphous phases of radioisotope bound on the surface of the inert ceramic substrate. The underlying surface on which the amorphous phases of the radioisotope are bound may comprise the radioisotope-doped layer described herein. The term "amorphous phase" in relation to the radioisotope is understood to mean radioisotope existing within a microscopic structure without any regular, extended atomic arrangement, i.e. having no defined crystal lattice. In one embodiment, the immobilised parent radioisotope are provided as one or more amorphous phases of parent radioisotope bound on the surface of the inert ceramic substrate. The one or more amorphous phases of radioisotope may be uniformly distributed on the surface of the inert ceramic substrate, for example at the nanometre scale (for example as observed under a scanning electron microscope). The one or more amorphous phases of parent radioisotope may be bound to the lattice of the inert ceramic substrate.

In one embodiment, the one or more of the solid compound, crystalline or amorphous phases are provided as discrete particles bound on the surface of the inert ceramic substrate. The underlying surface on which the discrete particles are bound may comprise the radioisotope-doped layer described herein. The discrete particles may be described as a plurality of "islands" bound on the surface of the inert ceramic substrate. Alternatively or additionally, the one or more of the solid compound, crystalline or amorphous phases are provided as a layer bound on the surface of the inert ceramic substrate.

In some embodiments, the one or more crystalline phases of the parent radioisotope are provided as a plurality of discrete crystalline particles bound to the surface of the inert ceramic substrate or radioisotope-doped layer. Alternatively or additionally, the one or more crystalline phases of parent radioisotope are provided as a crystalline layer bound to the surface of the inert ceramic substrate or radioisotope-doped layer. In some embodiments, the discrete particles and/or layer may be bound to the surface of the underlying radioisotope-doped layer or inert ceramic substrate, and for example may have a close lattice match with one or more crystalline compound phases present at the surface of the inert ceramic substrate or radio-isotope doped layer. The lattice mismatch between the discrete crystalline particles or crystalline layer of radioisotope and the underlying inert ceramic substrate or radioisotope-ion doped layer may be less than about 10, 9, 8, 7, 6, 5, 4, 3, 2 or 1%.

If present, the layer of solid compound, crystalline or amorphous phases may be located anywhere on the surface of the inert ceramic substrate. The layer of solid compound, crystalline or amorphous phases may be a continuous layer on the surface of the substrate. Alternatively, the layer of solid compound, crystalline or amorphous phases may be non-continuous with respect to the entire inert substrate surface, and may comprise two or more sections for example where the layer does not uniformly and fully cover the surface of the inert ceramic substrate.

In one embodiment, the one or more solid compound, crystalline, or amorphous phases of the parent radioisotope comprise an oxide, hydroxide, oxalate, nitride, carbide, sulfide, silicate, intermetallic compound, or a combination thereof, of the radioisotope described herein. In one embodiment, the one or more solid compound, crystalline, or amorphous phases of the parent radioisotope comprise an oxide, hydroxide, fluoride, oxalate, phosphate, nitride, carbide, sulfide, silicate, intermetallic compound, or a combination thereof, of the radioisotope described herein. In one embodiment, the one or more solid compound, crystalline, or amorphous phases of the parent radioisotope comprise an oxide, nitride, fluoride, phosphate, carbide, sulfide, silicate or combination thereof, of the radioisotope described herein. In one embodiment, the one or more solid compound, crystalline, or amorphous phases of the parent radioisotope comprise an oxide, nitride, carbide, sulfide, silicate or combination thereof, of the radioisotope described herein. In one embodiment, the one or more solid compound, crystalline, or amorphous phases of the parent radioisotope comprise an oxide, phosphate, nitride, carbide, sulfide, or combination thereof, of the radioisotope described herein. In one embodiment, the one or more solid compound, crystalline, or amorphous phases of the parent radioisotope comprise an oxide or hydroxide, or combination thereof, of the radioisotope described herein. In one embodiment, the one or more solid compound, crystalline, or amorphous phases of the parent radioisotope is an oxide of the radioisotope described herein.

In one embodiment, the one or more solid compound, crystalline, or amorphous phases of the parent radioisotope comprise thorium dioxide ($ThO_2$) and/or nonstoichiometric thorium oxide ($ThO_{(2+/-x)}$, wherein x is greater than 0 but less than 0.15.

The thickness of the radioisotope surface layer, heat-treated radioisotope surface layer, radioisotope-doped layer, solid compound, crystalline or amorphous phases may vary, for example depending on the amount of parent radioisotope being loaded onto the surface of the inert ceramic substrate. The radioisotope surface layer, heat-treated radioisotope surface layer, radioisotope-doped layer, solid compound, crystalline or amorphous phases may each independently have a thickness effective to provide a concentration of radioisotope in an amount effective to provide an activity (in MBq per $cm^2$ of inert ceramic substrate) as described above, for example between about 1 to about 1500.

In some embodiments, the radioisotope surface layer, heat-treated radioisotope surface layer, radioisotope-doped layer, solid compound, crystalline or amorphous phases, may each independently have a thickness of between about 0.1 nm to about 1,000,000 nm (i.e. 1 mm), between about 0.1 nm to about 100,000 nm (i.e. 100 gm), or between about 0.1 nm to about 1,000 nm (i.e. 1 gm). The radioisotope surface layer, heat-treated radioisotope surface layer, radioisotope-doped layer, solid compound, crystalline or amorphous phases, may each independently have a thickness (in nm) of at least about 0.1, 0.2, 0.4, 0.6, 0.8, 1, 1.2, 1.4, 1.6, 1.8, 2, 2.5, 3, 3.5, 4, 5, 6, 7, 8, 9, 10, 12, 14, 16, 18, 20, 30, 50, 100, 150, 200, 300, 400, 500, 700, 900, 1,000, 10,000, 100,000, or 1,000,000. The radioisotope surface layer, heat-treated radioisotope surface layer, radioisotope-doped layer, solid compound, crystalline or amorphous phases, may each independently have a thickness (in nm) of less than about 1,000,000, 100,000, 10,000, 1,000, 900, 700, 500, 400, 300, 200, 150, 100, 50, 30, 20, 18, 16, 14, 12, 10, 9, 8, 7, 6, 5, 4, 3.5, 3, 2.5, 2, 1.8, 1.6, 1.4, 1.2, 1, 0.8, 0.6, 0.4, 0.2 or 0.1. The radioisotope surface layer, heat-treated radioisotope surface layer, radioisotope-doped layer, solid compound, crystalline or amorphous phases, may each independently have a thickness (in nm) of at least about 0.2, 0.4, 0.6, 0.8, 1, 1.2, 1.4, 1.6, 1.8, 2, 2.5, 3, 3.5, 4, 5, 6, 7, 8, 9, 10, 12, 14, 16, 18 or 20. The radioisotope surface layer, heat-treated radioisotope surface layer, radioisotope-doped layer, solid compound, crystalline or amorphous phases, may each independently have a thickness (in nm) of less than about 20, 18, 16, 14, 12, 10, 9, 8, 7, 6, 5, 4, 3.5, 3, 2.5, 2, 1.8, 1.6, 1.4, 1.2, 1, 0.8, 0.6, 0.4 or 0.2 nm. The thickness may be in a range provided by any two of these upper and/or lower values, for example between about 0.1 nm to about 1,000,000 nm, between about 0.1 nm to about 100,000 nm, between about 0.1 nm to about 1,000 nm, between about 0.1 nm to about 100 nm, between about 1 nm to about 100 nm, or between about 1 nm to about 20 nm. According to some embodiments or examples described herein, a thin radioisotope surface layer described herein (which includes the heat-treated radioisotope surface layer/radioisotope-doped layer/solid compound, crystalline or amorphous phases, on the inert ceramic substrate described herein) allows for effective emanation of the gaseous intermediate radioisotope away from the inert ceramic substrate.

In some embodiments, the radioisotope surface layer may have a thickness of between about 0.1 nm to about 1,000,000 nm (i.e. 1 mm), between about 0.1 nm to about 100,000 nm (i.e. 100 gm), or between about 0.1 nm to about 1,000 nm (i.e. 1 gm). The radioisotope surface layer may have a thickness (in nm) of at least about 0.1, 0.2, 0.4, 0.6, 0.8, 1, 1.2, 1.4, 1.6, 1.8, 2, 2.5, 3, 3.5, 4, 5, 6, 7, 8, 9, 10, 12, 14, 16, 18, 20, 30, 50, 100, 150, 200, 300, 400, 500, 700, 900, 1,000, 10,000, 100,000, or 1,000,000. The radioisotope surface layer may have a thickness (in nm) of less than about 1,000,000, 100,000, 10,000, 1,000, 900, 700, 500, 400, 300, 200, 150, 100, 50, 30, 20, 18, 16, 14, 12, 10, 9, 8, 7, 6, 5, 4, 3.5, 3, 2.5, 2, 1.8, 1.6, 1.4, 1.2, 1, 0.8, 0.6, 0.4, 0.2 or 0.1. The radioisotope surface layer may have a thickness (in nm) of at least about 0.2, 0.4, 0.6, 0.8, 1, 1.2, 1.4, 1.6, 1.8, 2, 2.5, 3, 3.5, 4, 5, 6, 7, 8, 9, 10, 12, 14, 16, 18 or 20. The radioisotope surface layer may have a thickness (in nm) of less than about 20, 18, 16, 14, 12, 10, 9, 8, 7, 6, 5, 4, 3.5, 3, 2.5, 2, 1.8, 1.6, 1.4, 1.2, 1, 0.8, 0.6, 0.4 or 0.2 nm. The thickness may be in a range provided by any two of these upper and/or lower values, for example between about 0.1 nm to about 1,000,000 nm, between about 0.1 nm to about 100,000 nm, between about 0.1 nm to about 1,000 nm, between about 0.1 nm to about 100 nm, between about 1 nm to about 100 nm, or between about 1 nm to about 20 nm.

In some embodiments, the heat-treated radioisotope surface layer may have a thickness of between about 0.1 nm to about 1,000,000 nm (i.e. 1 mm), between about 0.1 nm to about 100,000 nm (i.e. 100 gm), or between about 0.1 nm to about 1,000 nm (i.e. 1 μm). The heat-treated radioisotope surface layer may have a thickness (in nm) of at least about 0.1, 0.2, 0.4, 0.6, 0.8, 1, 1.2, 1.4, 1.6, 1.8, 2, 2.5, 3, 3.5, 4, 5, 6, 7, 8, 9, 10, 12, 14, 16, 18, 20, 30, 50, 100, 150, 200, 300, 400, 500, 700, 900, 1,000, 10,000, 100,000, or 1,000,000. The heat-treated radioisotope surface layer may have a thickness (in nm) of less than about 1,000,000, 100,000, 10,000, 1,000, 900, 700, 500, 400, 300, 200, 150, 100, 50, 30, 20, 18, 16, 14, 12, 10, 9, 8, 7, 6, 5, 4, 3.5, 3, 2.5, 2, 1.8, 1.6, 1.4, 1.2, 1, 0.8, 0.6, 0.4, 0.2 or 0.1. The heat-treated radioisotope surface layer may have a thickness (in nm) of at least about 0.2, 0.4, 0.6, 0.8, 1, 1.2, 1.4, 1.6, 1.8, 2, 2.5, 3, 3.5, 4, 5, 6, 7, 8, 9, 10, 12, 14, 16, 18 or 20. The heat-treated radioisotope surface layer may have a thickness (in nm) of less than about 20, 18, 16, 14, 12, 10, 9, 8, 7, 6, 5, 4, 3.5, 3, 2.5, 2, 1.8, 1.6, 1.4, 1.2, 1, 0.8, 0.6, 0.4 or 0.2 nm. The thickness may be in a range provided by any two of these upper and/or lower values, for example between about 0.1 nm to about 1,000,000 nm, between about 0.1 nm to about 100,000 nm, between about 0.1 nm to about 1,000 nm, between about 0.1 nm to about 100 nm, between about 1 nm to about 100 nm, or between about 1 nm to about 20 nm.

In some embodiments, the radioisotope-doped layer may have a thickness of between about 0.1 nm to about 1,000,000 nm (i.e. 1 mm), between about 0.1 nm to about 100,000 nm (i.e. 100 gm), or between about 0.1 nm to about 1,000 nm (i.e. 1 gm). The radioisotope-doped layer may have a thickness (in nm) of at least about 0.1, 0.2, 0.4, 0.6, 0.8, 1, 1.2, 1.4, 1.6, 1.8, 2, 2.5, 3, 3.5, 4, 5, 6, 7, 8, 9, 10, 12, 14, 16, 18, 20, 30, 50, 100, 150, 200, 300, 400, 500, 700, 900, 1,000, 10,000, 100,000, or 1,000,000. The radioisotope-doped layer may have a thickness (in nm) of less than about 1,000,000, 100,000, 10,000, 1,000, 900, 700, 500, 400, 300, 200, 150, 100, 50, 30, 20, 18, 16, 14, 12, 10, 9, 8, 7, 6, 5, 4, 3.5, 3, 2.5, 2, 1.8, 1.6, 1.4, 1.2, 1, 0.8, 0.6, 0.4, 0.2 or 0.1. The radioisotope-doped layer may have a thickness (in nm) of at least about 0.2, 0.4, 0.6, 0.8, 1, 1.2, 1.4, 1.6, 1.8, 2, 2.5, 3, 3.5, 4, 5, 6, 7, 8, 9, 10, 12, 14, 16, 18 or 20. The radioisotope-doped layer may have a thickness (in nm) of less than about 20, 18, 16, 14, 12, 10, 9, 8, 7, 6, 5, 4, 3.5, 3, 2.5, 2, 1.8, 1.6, 1.4, 1.2, 1, 0.8, 0.6, 0.4 or 0.2 nm. The thickness may be in a range provided by any two of these upper and/or lower values, for example between about 0.1 nm to about 1,000,000 nm, between about 0.1 nm to about 100,000 nm, between about 0.1 nm to about 1,000 nm, between about 0.1 nm to about 100 nm, between about 1 nm to about 100 nm, or between about 1 nm to about 20 nm.

In some embodiments, the solid compound, crystalline or amorphous phases, may each independently have a thickness of between about 0.1 nm to about 1,000,000 nm (i.e. 1 mm), between about 0.1 nm to about 100,000 nm (i.e. 100 μm), or between about 0.1 nm to about 1,000 nm (i.e. 1 μm). The solid compound, crystalline or amorphous phases, may each independently have a thickness (in nm) of at least about 0.1, 0.2, 0.4, 0.6, 0.8, 1, 1.2, 1.4, 1.6, 1.8, 2, 2.5, 3, 3.5, 4, 5, 6, 7, 8, 9, 10, 12, 14, 16, 18, 20, 30, 50, 100, 150, 200, 300, 400, 500, 700, 900, 1,000, 10,000, 100,000, or 1,000,000. The solid compound, crystalline or amorphous phases, may each independently have a thickness (in nm) of less than about 1,000,000, 100,000, 10,000, 1,000, 900, 700, 500, 400, 300, 200, 150, 100, 50, 30, 20, 18, 16, 14, 12, 10, 9, 8, 7, 6, 5, 4, 3.5, 3, 2.5, 2, 1.8, 1.6, 1.4, 1.2, 1, 0.8, 0.6, 0.4, 0.2 or 0.1. The solid compound, crystalline or amorphous phases, may each independently have a thickness (in nm) of at least about 0.2, 0.4, 0.6, 0.8, 1, 1.2, 1.4, 1.6, 1.8, 2, 2.5, 3, 3.5, 4, 5, 6, 7, 8, 9, 10, 12, 14, 16, 18 or 20. The solid compound, crystalline or amorphous phases, may each independently have a thickness (in nm) of less than about 20, 18, 16, 14, 12, 10, 9, 8, 7, 6, 5, 4, 3.5, 3, 2.5, 2, 1.8, 1.6, 1.4, 1.2, 1, 0.8, 0.6, 0.4 or 0.2 nm. The thickness may be in a range provided by any two of these upper and/or lower values, for example between about 0.1 nm to about 1,000,000 nm, between about 0.1 nm to about 100,000 nm, between about 0.1 nm to about 1,000 nm, between about 0.1 nm to about 100 nm, between about 1 nm to about 100 nm, or between about 1 nm to about 20 nm.

Properties of Inert Ceramic Substrates for Immobilising Radioisotope

The parent radioisotope described herein is immobilised on or within an inert ceramic substrate. The term "inert" will be understood to mean that the ceramic substrate is substantially chemically inert, and for example does not chemically react to a significant degree with the immobilised radioisotope interspersed on or within the substrate. The inert ceramic substrate may also not substantially react with atmospheric oxygen and water. Additionally, the inert ceramic substrate may comprise ceramic material of a certain robustness making it less susceptible to radiation damage (i.e. structural damage) inflicted as the parent radioisotope immobilised therein decays into daughter radioisotope. For example, owing to the crystallographic properties of the inert ceramic substrate, a degree of robustness toward radiation damage is provided.

In one embodiment or example, the inert ceramic substrate is an inert metal oxide which the present inventors identified as tough and robust having a reduced susceptibility to radiation damage. While being robust, the inert ceramic substrate is also composed of a material which does not prevent to a significant degree the emanation of gaseous daughter radioisotope away from the parent radioisotope immobilised on or within the inert ceramic substrate as it decays, thereby providing for effective separation of the emanated daughter radioisotope from the immobilised radioisotope.

The inert ceramic substrate may be formed from any suitable ceramic material. For example, the inert ceramic substrate comprises a suitable ceramic material which may have chemical affinity for the parent radioisotope to be immobilised, for example supporting the exchange of parent radioisotope ions with those of the ceramic lattice. In some embodiments, the inert ceramic substrate is configured to support one or more crystalline compound phases of radioisotope.

The inert ceramic substrate may have a morphology suitable for inserting into a radioisotope generator, for example into the source chamber described herein. In one embodiment, the inert ceramic substrate may be provided as a discrete unit, for example a disk, plate, film, platen, slab, tube, tube-section or monolith. The unit may have any desired shape including, but not limited to spherical or semi-spherical. In one embodiment, the inert ceramic substrate is a disk. The disk may be configured to be inserted into a radioisotope generator. Provided the disk is substantially planar in geometry, the disk is not limited to being any particular cross-sectional shape (i.e. spherical, rectangular etc.).

In one embodiment, the inert ceramic substrate has an aspect ratio (i.e. the ratio of a length to a width, where the length and width are measured perpendicular to one another, and the length refers to the longest linear dimension) of greater than 1.0 to about 10.0, for example at least about 2.0, 2.5 3.0, 3.5, 4.0, 5.0, 6.0, 7.0, 8.0, 9.0 or 10.0. According to some embodiments or examples described herein, an inert ceramic substrate having a higher aspect ratio (e.g. greater than 2.0) provides a planar geometry that provides a larger radioisotope surface layer area for effective emanation of gaseous intermediate radioisotope.

The inert ceramic substrate has a degree of porosity effective to allow for the immobilisation of an amount of parent radioisotope yet still allow for effective emanation of gaseous daughter radioisotope away from the inert ceramic substrate surface, thereby providing effective separation of the emanated daughter radioisotope from the immobilised parent radioisotope. The degree of porosity may be greater at the surface of the inert ceramic substrate. The degree of porosity may facilitate the immobilisation of a substantial amount of parent radioisotope. As used herein, the term "porosity" is a measure of the void spaces in a material and is a fraction of the volume of voids over the total volume as a percentage between 0 vol. % and 100 vol. %.

In some embodiments, the inert ceramic substrate has a porosity of between about 0.01 vol. % to about 30 vol. % based on the total volume of the inert ceramic substrate. The inert ceramic substrate may have a porosity (in vol. % based on the total volume of the inert ceramic substrate) of at least about 0.01, 0.1, 1, 2, 5, 10, 20, or 30. The inert ceramic substrate may have a porosity (in vol. % based on the total volume of the inert ceramic substrate) of less than about 30, 20, 10, 5, 2, 1, 0.1, or 0.01. In one embodiment, the inert ceramic substrate has a porosity (in vol. % based on the total volume of the inert ceramic substrate) of less than about 10, 5, 2, 1, 0.1, or 0.01. The porosity may be a range provided by any two of these upper and/or lower values, for example between about 10 vol. % to about 30 vol. %, or between about 0.01 vol. % to about 5 vol. %. The vol. % porosity can be measured by any suitable technique known to the person skilled in the art, including for example using standard mercury porosimetry methods and/or optical or electron microscopy analysis of a cross-section of the inert ceramic substrate. According to some embodiments or examples described herein, an inert ceramic substrate having low porosity may provide one or more advantages, including high yields of daughter isotope. For example, inert ceramic substrates having a morphology that is of low porosity, and in some cases being substantially non-porous (e.g. less than about 1, 0.1 or 0.01 vol. %) allows for more effective and substantially unimpeded emanation of gaseous intermediate isotope away from the radioisotope surface layer.

Related to porosity, the inert ceramic substrate may have low surface area, for example may have a surface area (in m$^2$/g) of less than about 200, 100, 50, 20, 10, 5, 4, 3, 2, 1 or 0.5. The surface area can be measured using standard ASTM C1274 or using N2 adsorption with Brunauer-Emmett-Teller (BET) theory applied over the relative pressure range of 0.05 to 0.20 P/Po at 77 K.

The inert ceramic substrate density has a suitable density, for example to provide a degree of robustness. In some embodiments, the inert ceramic substrate has a density of between about 2.0 g/cm$^3$ to about 15 g/cm$^3$. The inert ceramic substrate may have a density (g/cm$^3$) of at least about 2, 3, 4, 5, 6, 7, 8, 9, 10, 11, 12, 13, 14 or 15. The inert ceramic substrate may have a density (g/cm$^3$) of less than about 15, 14, 13, 12, 11, 10, 9, 8, 7, 6, 5, 4, 3 or 2. The density may be a range provided by any two of these upper and/or lower values, for example between about 4 to 13 g/cm$^3$.

The inert ceramic substrate has a suitable thickness. In some embodiments, the inert ceramic substrate has a thickness (in μm) of between about 0.001 to about 100,000, between about 0.001 to about 10,000, between about 0.001 to about 1000, between about 0.01 to about 100, between about 0.01 to about 10, or between about 0.1 to about 10, or between about 0.005 to about 0.5. The inert ceramic substrate may have a thickness (in gm) of at least about 0.001, 0.002, 0.005, 0.01, 0.015, 0.02, 0.05, 0.1, 0.5, 1, 5, 10, 50, 100, 200, 500, 700, 1000, 5000, 10,000 or 100,000. The inert ceramic substrate may have a thickness (in gm) of less than about 10,000, 10,000, 5000, 1000, 700, 500, 200, 100, 50, 10, 5, 1, 0.5, 0.1, 0.05, 0.02, 0.015, 0.01, 0.005, 0.002, or 0.001. The thickness may be a range provided by any two of these upper and or lower values, for example between about 0.01 gm to about 500 μm. In another embodiment, the inert ceramic substrate may have a thickness (in nm) of at least about 5, 10, 15, 20, 25, 30, 40, 50, 80, 100, 150, 200, 250, 300, 400 or 500. The inert ceramic substrate may have a thickness (in nm) of less than about 500, 400, 300, 250, 200, 150, 100, 80, 50, 40, 30, 25, 20, 15, 10 or 5. The thickness may be a range provided by any two of these upper or lower values, for example between about 15 nm to about 100 nm. In one embodiment, the thickness of the radioisotope surface layer is less than the thickness of the underlying inert ceramic substrate.

The inert ceramic substrate may have a roughened or textured surface. According to some embodiments or examples described herein, it was found that a roughened or textured surface provided an enhanced surface area which can facilitate the loading and immobilising of the radioisotope on or within the inert ceramic substrate. It will be appreciated that such surface roughening or texturing is understood to mean that the surface of the substrate has been manipulated (i.e. roughened or textured) and does not encompass native "dead-flat" or polished metals which may have some form of microscopic roughness. In other words, the surface roughening is achieved by some physical or mechanical processing of the substrates surface, for example via abrading the surface using an abrasive powder (e.g. tungsten carbide) on an oscillating table. The surface roughness may comprise angular patterns.

In some embodiments, the inert ceramic substrate has a surface roughness ($R_t$) of between about 5 μm to about 150 μm (i.e. the peak-to-trough height of one or more angular peaks generated by the roughening). The roughened surface may have a peak count ($R_{pc}$) of less than 180 peaks/cm. The surface roughness may be measured using industry standard ASTM D7127, for example following abrasive treatment.

In some embodiments, the roughened surface of the inert ceramic substrate has an increased % surface area compared to a corresponding non-roughened "dead-flat" substrate, for example at least about a 1, 2, 5, 10, 15 or 20% increase in surface area.

The inert ceramic substrate is selected from a metal oxide, metal nitride, metal carbide, metal sulfide, or combination thereof. The inert ceramic substrate is selected from a metal oxide, metal phosphate, metal nitride, metal carbide, metal sulfide, or combination thereof. Other suitable ceramic materials include inert intermetallic compounds, for example a metal silicide, metal boride, or a metal selenide. In one embodiment, the inert ceramic substrate is a metal oxide.

In one embodiment, the inert ceramic substrate is a metal oxide substrate. The metal oxide substrate may be an oxide of a refractory metal or another transition metal. The metal oxide substrate may be an oxide of tantalum, niobium, tungsten, molybdenum, vanadium, zirconium, titanium or aluminium, or alloys thereof. The metal oxide substrate may be an oxide of tantalum, niobium, tungsten, molybdenum, vanadium, zirconium, titanium. In one embodiment, the inert metal oxide substrate is tantalum oxide ($Ta_2O_5$). Other metals are also envisaged.

In one embodiment, the inert ceramic substrate is provided as a layer (e.g. a film supported on an underlying substrate). In one embodiment, the inert ceramic substrate may be provided as a layer on a metal substrate. The inert ceramic substrate layer may be supported on a metal substrate. The metal substrate may provide further advantages according to some embodiments or examples described herein, including radiation shielding. Additionally, according to some embodiments or examples, the metal substrate can provide stable anchoring for the thinner inert ceramic substrate when in the source chamber described herein, for example, upon contact with a carrier gas.

The metal substrate may have a morphology suitable for inserting into a generator, for example into the source chamber described herein. In one embodiment, the metal substrate may be provided as a discrete unit, for example a disk, plate, film, platen, slab, tube, tube-section or monolith. The metal substrate may have any desired shape including, but not limited to spherical or semi-spherical. In one embodiment, the metal substrate is a disk or slab. The disk may be configured to be inserted into a radioisotope generator.

In some embodiments, the metal substrate has a thickness of between about 1 mm to about 30 mm. The metal substrate may have a thickness (in mm) of at least about 0.5, 1, 2, 3, 4, 5, 6, 7, 8, 9, 10, 12, 15, 20, 25, 30. The metal substrate may have a thickness (in mm) of less than about 30, 25, 20, 15, 12, 10, 9, 8, 7, 6, 5, 4, 3, 2, 1 or 0.5. The thickness may be a range provided by any two of these upper or lower values, for example between about 1 mm to about 10 mm, e.g. about 6 mm. The metal substrate may have a thickness effective to provide a flat surface for the inert ceramic substrate. In some embodiments, thicker metal substrates may be more amenable to recycling/reconditioning/reuse, for example rendering it safer and easier to strip unused radioisotope from the substrate. Additionally, thicker metal substrates may be more amenable to creating a uniform roughened surface as described herein according to some embodiments or examples. In one embodiment, the thickness of the inert ceramic substrate is less than the thickness of the underlying metal substrate.

In one embodiment, the surface of the metal substrate comprising the inert ceramic oxide substrate layer has a surface area of between about 0.125 cm$^2$ to about 50 cm$^2$. The metal substrate comprising the inert ceramic oxide substrate layer may have a surface area (in cm$^2$) of at least about 0.125, 0.25, 0.5, 0.75, 1, 1.5, 2, 3, 4, 5, 10, 15, 20, 25, 30, 35, 40, 45 or 50. The metal substrate comprising the inert ceramic oxide substrate layer may have a surface area (in cm$^2$) of less than about 50, 45, 40, 35, 30, 25, 20, 15, 10, 5, 4, 3, 2, 1.5, 1, 0.75, 0.5, 0.25 or 1.25. A range may be provided by any two of these upper and/or lower values.

In one embodiment, the metal of the metal substrate and inert ceramic substrate (e.g. on the surface of the metal substrate) are the same. In one embodiment, the inert ceramic substrate is a metal oxide substrate, and the metal of the metal substrate and metal oxide substrate are the same.

In one embodiment, the metal substrate is a refractory or other transition metal. The metal substrate may be tantalum, niobium, tungsten, molybdenum, vanadium, zirconium, titanium or aluminium, or alloys thereof. The metal substrate may be tantalum, niobium, tungsten, molybdenum, vanadium, zirconium, or titanium, or alloys thereof. In one embodiment, the inert ceramic substrate is a metal oxide and is provided as a layer (e.g. surface layer) on a metal substrate or electrode thereof selected from tantalum, niobium, tungsten, molybdenum, vanadium, zirconium, titanium or aluminium, or alloys thereof.

In one embodiment, the metal substrate is an anodisable metal. The anodisable metal substrate or electrode thereof may be selected from tantalum, niobium, titanium or aluminium, or alloys thereof. The anodisable metal substrate or electrode thereof may be selected from tantalum, niobium, zirconium, titanium or aluminium, or alloys thereof.

In one embodiment, the inert metal oxide substrate is produced by oxidatively pre-treating the surface of the metal substrate. In one example or embodiment, the inert ceramic substrate is a metal oxide substrate layer comprising a metal oxide produced by the anodic polarisation of the surface of the anodisable metal substrate. In this example or embodiment, the metal substrate is a metal electrode. Anodic polarisation of the metal substrate or electrode thereof is described herein.

Alternatively, in another example, the inert ceramic substrate is a metal oxide layer comprising a metal oxide produced by oxidation (e.g. passive or native oxidation) of the surface of the metal substrate. The oxidation may also be induced by thermally oxidising the metal substrate in an oxygen atmosphere and/or by subjecting the metal substrate to more aggressive oxidising environments (e.g. an atmosphere with an elevated oxygen level).

The metal substrate may have a roughened or textured surface. The embodiments described above in relation to the roughened or textured surface of the inert ceramic substrate equally apply for the roughened or textured surface of the metal substrate. According to some embodiments or examples described herein, it was found that the roughened or textured surface of the metal substrate generated a textured metal oxide layer on the surface of the metal substrate, having an enhanced surface area and wettability which facilitates the loading and immobilising of the radioisotope. In some embodiments, a rough inert ceramic substrate (e.g. a rough metal oxide substrate) natively forms on the roughened surface of the metal substrate, for example by passive oxidation. Alternatively, a rough inert ceramic substrate (e.g. a rough metal oxide substrate) is generated on the surface of the roughened metal substrate or electrode thereof via anodic polarisation, as described herein.

By way of example, a schematic of an inert ceramic substrate comprising immobilised radioisotope is provided in FIG. 1. The inert ceramic substrate comprises a metal substrate (101) and a metal oxide layer on the metal substrate (102). In one example, the metal oxide layer is first prepared by the anodisation of the metal substrate/electrode. At least some of the radioisotope is bound on or near the surface of the metal oxide as a radioisotope surface layer (e.g. any one or more of 103, 104, 105 and 107). In one example, some of the immobilised radioisotope forming the radioisotope surface layer is provided as a radioisotope doped layer (103) on and/or within the surface of the inert metal oxide, wherein radioisotope (104) are interspersed within the surface of the metal oxide. Alternatively or additionally, some of the immobilised radioisotope forming the radioisotope surface layer are provided as one or more solid compound phases bound on the surface of the metal oxide, such as crystalline oxide phases of radioisotope (105) or as amorphous phases of radioisotope (107) bound on or within the surface of the inert metal oxide, and in some cases may be bound on and/or within the radioisotope doped layer (103).

Figure 2:
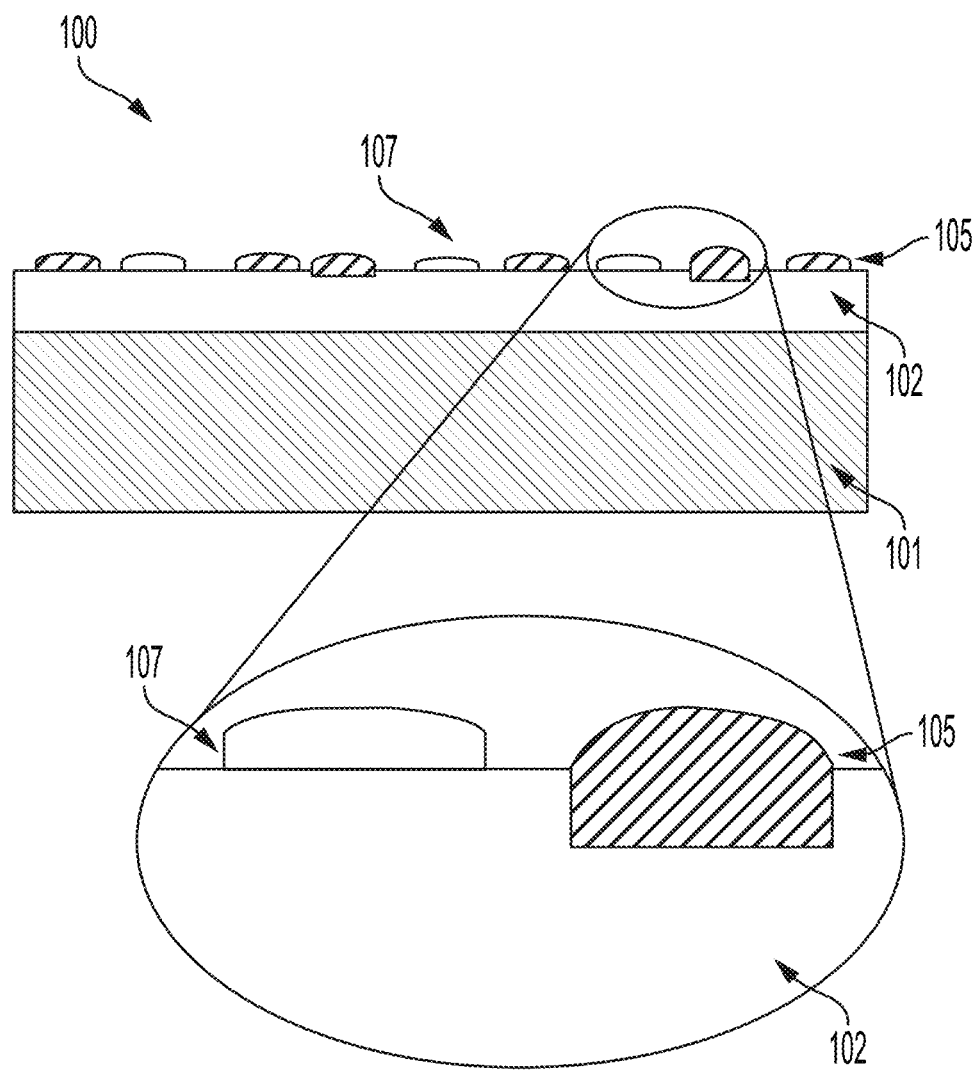
FIG. 2 shows a schematic of another embodiment of an inert ceramic substrate comprising immobilised radioisotope.

In another example, the radioisotope surface layer is provided as one or more solid compound phases of the radioisotope bound on the surface of the inert ceramic substrate as provided in FIG. 2, wherein the immobilised radioisotope forming the radioisotope surface layer are provided as one or more solid compound phases bound on the surface of the metal oxide, such as crystalline oxide phases of radioisotope (105) or as amorphous phases of radioisotope (107) bound on or within the surface of the inert metal oxide.

It will be appreciated that the radioisotope surface layer does not have to be a continuous uniform layer covering the entire surface of the metal oxide surface (102) of the inert ceramic substrate (101). For example, referring to FIG. 1, one or more small sections of the metal oxide surface (106) may protrude through the radioisotope-doped layer (103) as result of non-uniform coverage. Alternatively, the radioisotope surface layer may comprise one or more solid compound phases of parent radioisotope decorated on the surface of the inert ceramic substrate, such as one or more crystalline oxide phases of radioisotope (105) or as amorphous phases of radioisotope (107) bound on or within the surface of the inert metal oxide. In both instances, the metal oxide layer will still be considered as comprising a radioisotope surface layer described herein, irrespective as to whether the immobilised parent radioisotope forms a continuous layer or forms one or more phases/sections decorating the surface of the inert ceramic substrate.

Process for Preparing Inert Ceramic Substrate Comprising Immobilised Radioisotope.

The present disclosure also provides a process for immobilising parent radioisotope on or within an inert ceramic substrate. In one aspect or embodiment, there is provided a process for preparing an inert ceramic substrate comprising parent radioisotope immobilised on or within the inert ceramic substrate, the process comprising the steps of: a) depositing a solution comprising a parent radioisotope species on the surface of an inert ceramic substrate; and b) heating the inert ceramic substrate to a temperature effective to immobilise parent radioisotope on or within the inert ceramic substrate.

In one embodiment or example, there is provided a process for preparing an inert ceramic substrate comprising parent radioisotope immobilised on or within the inert ceramic substrate, the process comprising the steps of: a) depositing a solution comprising a parent radioisotope species on the surface of an inert ceramic substrate; b) heating the inert ceramic substrate to a temperature effective to bind at least some of the parent radioisotope on or near the surface of the inert ceramic substrate forming a heat-treated radioisotope surface layer to allow for effective emanation of gaseous daughter radioisotope away from the inert ceramic substrate.

In a related embodiment or example, there is provided a process for preparing an inert ceramic substrate comprising parent radioisotope immobilised on or within the inert ceramic substrate, the process comprising the steps of: a) depositing a solution comprising a parent radioisotope species on the surface of an inert ceramic substrate; b) heating the inert ceramic substrate to a temperature effective to bind at least some of the parent radioisotope on or near the surface of the inert ceramic substrate forming a heat-treated radioisotope surface layer to allow for effective emanation of gaseous daughter radioisotope away from the inert ceramic substrate.

In a related embodiment or example, there is provided a process for preparing an inert ceramic substrate comprising parent radioisotope immobilised on or within the inert ceramic substrate in an amount effective to generate a medically useful dose of daughter radioisotope through a chain of spontaneous decay from the parent radioisotope via a gaseous intermediate radioisotope, the process comprising the steps of: a) depositing a solution comprising a parent radioisotope species on the surface of an inert ceramic substrate; b) heating the inert ceramic substrate to a temperature effective to bind at least some of the parent radioisotope on or near the surface of the inert ceramic substrate forming a heat-treated radioisotope surface layer to allow for effective emanation of the gaseous daughter radioisotope away from the inert ceramic substrate.

Oxidative Pre-Treatment of the Inert Ceramic Substrate

The solution comprising parent radioisotope species is deposited on the surface of an inert ceramic substrate. The surface of the inert ceramic substrate may be provided by oxidatively pre-treating the inert ceramic substrate prior to deposition of the radioisotope solution. In one embodiment, the process comprises the step of providing an inert ceramic substrate having a surface which has been pre-prepared by oxidative pre-treatment as described herein.

The inert ceramic substrate may be a layer on the surface of a metal. In one embodiment, the inert ceramic substrate layer is a metal oxide layer on the surface of the metal. The metal oxide layer may be prepared by surface modification of the metal. In one embodiment, the metal oxide layer may be prepared by oxidising a metal (i.e. a reaction in which electrons are removed) to prepare a metal oxide layer on the surface of the metal. The oxidation of the surface of the metal may be passive (i.e. occurring spontaneously in air) thereby forming a native metal oxide surface layer on the metal, or it may be energetically driven by an oxidative pre-treatment of the metal surface. For example, the oxidation of the surface of the metal may comprise a chemical reaction with an oxidising agent to form the inert ceramic substrate as a surface oxide layer on the metal.

In one embodiment, the metal may be subjected to thermal oxidation (i.e. heating under an oxygen environment) to generate the metal oxide layer. In another embodiment, the metal may be subjected to anodic polarisation (also called anodising) to generate the metal oxide layer. The metal may also be called a metal substrate, as described herein, and the oxidation described herein can produce a metal oxide layer on the surface of the metal substrate. Accordingly, in one embodiment, the inert ceramic substrate is a metal oxide layer on the surface of a metal substrate. The metal oxide layer may be formed by thermal oxidation or anodic polarisation.

Thermal oxidation is a well-understood process in which a metal (in its zero oxidation state) reacts with atmospheric oxygen at its surface to produce a definable layer of a metal oxide compound. The reaction relies on oxygen moving to the metal surface along cracks in pre-existing thin surface oxide films or by diffusion through such films. Oxygen diffusion is facilitated by temperature so heating the metal will increase both the reaction rate and the thickness of the metal oxide layer generated on the surface of the metal. The metal oxide layer may have variable stoichiometry and it may be initially formed as an amorphous material (with no defined lattice structure).

In one embodiment, the metal is heated in the presence of oxygen to a temperature effective to form a layer of a metal oxide (e.g. the inert ceramic substrate) on the surface of the metal. In one embodiment, the metal is heated in the presence of oxygen to a temperature between about 100° C. to about 900° C. The metal may be heated in the presence of oxygen at a temperature (in C) of at least about 100, 200, 220, 240, 260, 280, 300, 320, 340, 360, 380, 400, 450, 500, 550, 600, 650, 700, 750, 800, 850 or 900. The metal may be heated in the presence of oxygen at a temperature (in C) of less than about 900, 850, 800, 750, 700, 650, 600, 550, 500, 450, 400, 380, 360, 340, 320, 300, 280, 260, 240, 220, 200 or 100. The heating temperature may be a range provided by any two of these upper and/or lower values, for example between about 200° C. to about 900° C., or between about 300° C. to about 800° C.

The metal may be heated in the presence of oxygen from room temperature to the desired heating temperature at a rate of at least 1, 1.5, 2, 2.5, 2, 3.5, 3, 4, 4.5, 5, 6, 7, 8, 9 or 10° C./min. The heating rate may be a range provided by any two of these lower values.

The metal may be heated in the presence of oxygen for a period of time effective to form a layer of a metal oxide (e.g. the inert ceramic substrate) on the surface of the metal. The metal may be heated in the presence of oxygen for a period of time of between about 1 minutes to about 24 hours. The metal may be heated in the presence of oxygen for a period of time of at least about 1, 5, 10, 15, 20, 25, 30, 35, 40, 45, 50, 55, 60, 65, 70, 75, 80, 85, or 90 (minutes), 2, 3, 4, 5, 6, 8, 10, 12, 14, 16, 18, 20, 22 or 24 hours. The metal may be heated in the presence of oxygen for a period of time of less than about 24, 22, 20, 18, 16, 14, 12, 10, 8, 6, 5, 4, 3, 2 (hours), 90, 85, 80, 75, 70, 65, 60, 55, 50, 45, 40, 35, 30, 25, 20, 15, 10, 5, or 1 (minutes). The heating time may be a range provided by any two of these upper and/or lower values, for example between about 10 minutes to about 6 hours. Other heating temperatures and times to those recited herein are also envisaged, including longer heating times.

The metal may be subjected to a surface roughening step to provide a textured surface prior to a thermal oxidation step. The roughened surface is described herein in relation to the inert ceramic substrate. The surface roughening may be achieved by abrading the metal electrode with an abrasive material, for example tungsten carbide, as described herein.

Anodic polarisation is an electrochemical process used to generate metal oxide layers having a controlled thickness. The anodised metal oxide layer is grown by electrically polarising the metal as a positive electrode (anode) in an aqueous electrolyte and passing a direct current across the anode-electrolyte interface. A metal oxide layer is formed by oxygen ions diffusing from the electrolyte interface, through the pre-existing thin oxide layer to the underlying metal. The resulting metal oxide layer thickness is dependent on the voltage driving this transport. Other properties such as the oxide layer porosity and density can often be controlled. According to some embodiments or examples described herein, the present inventors have identified that an inert ceramic substrate prepared via anodic polarisation of a metal electrode provides a strong and robust substrate for immobilising radioisotope on or therein, thereby enabling effective separation of the emanated gaseous daughter radioisotope from the immobilised radioisotope tightly bound to the inert ceramic substrate.

In one embodiment, the process comprises anodising a metal electrode in an electrolyte solution in the presence of a counter electrode to form the metal oxide substrate layer on the surface of the anodisable metal electrode. Accordingly, in one embodiment, the metal oxide substrate may be a surface layer prepared by anodic polarisation of a surface of an anodisable metal electrode.

The metal may be subjected to a surface roughening step to provide a textured surface prior to anodising the metal surface. The roughened surface is described herein in relation to the inert ceramic substrate. The surface roughening may be achieved by abrading the metal electrode with an abrasive material, for example tungsten carbide.

The metal or anode thereof may be an anodisable metal as described herein in relation to the inert ceramic substrate, including for example, tantalum, niobium, titanium, vanadium, zirconium or aluminium, or alloys thereof. In one embodiment, the anodisable metal substrate or electrode thereof is tantalum and the metal oxide substrate layer is amorphous tantalum oxide, $Ta_2O_5$, or a substoichiometric variant thereof, as described herein.

The anodisation may be performed at a voltage effective to oxidise the surface of the metal electrode to form the metal oxide substrate layer. The anodisation may be performed at a voltage of between about 5 V to about 120 V, which may be measured with respect to a platinum or tantalum counter electrode in the same electrolyte solution and at which the water to hydrogen evolution reaction proceeds, or at which a reduction reaction of another electrolyte species proceeds, for example between about 10 V to about 100 V. The anodisation may be performed at a voltage of at least about 5, 10, 20, 30, 40, 50, 60, 70, 80, 90, 100 or 120 V. The anodising step may be performed at a voltage of less than about 120, 100, 90, 80, 70, 60, 50, 40, 30, 20, 10 or 5 V. The anodisation may be performed at a voltage in a range provided by any two of these upper and/or lower values, for example between about 10 V to about 50 V. The anodisation may be performed at a voltage of about 5, 10, 20, 30, 40, 50, 60, 70, 80, 90, 100 or 120 V.

The anodisation may be performed for a period of time at a given voltage effective to oxidise the surface of the metal electrode to form the metal oxide substrate layer. The anodisation may be performed for a period of time of between about 15 minutes to about 180 minutes. The anodisation may be performed for a period of time (in minutes) of at least about 5, 10, 15, 30, 45, 60, 75, 90, 105, 120, 135, 150, 165 or 180. The anodisation may be performed for a period of time (in minutes) of less than about 180, 165, 150, 135, 120, 105, 90, 75, 60, 45, 30, 15, 10 or 5. The anodisation may be performed for a period of time in a range provided by any two of these upper and/or lower values, for example between about 15 minutes to about 120 minutes.

The anodisation of the metal may be a stepwise anodisation process comprising polarising the metal electrode at two or more voltages as described above. The stepwise anodisation process may comprise increasing the voltage from about 5 V to about 120 V over a period of time of between about 30 minutes to about 120 minutes. Other suitable voltages and times are described herein in relation to the anodising step. For example, the anodising sequence may comprise (i) anodising the metal electrode at a first voltage of between about 5 V to about 15 V, then (ii) anodising the metal electrode at a second voltage of between about 15 V to about 25 V, and (iii) anodising the metal electrode at a third voltage of between about 25 V to about 80 V or between about 20 V to about 40 V. Step (i) may be performed for period of time of between about 10 minutes to about 20 minutes. Step (ii) may be performed for a period of time of between about 20 minutes and about 40 minutes. Step (iii) may be performed for a period of time of between about 20 minutes to about 40 minutes. Increasing the voltage in a step-wise manner may provide further advantages such as a well-controlled thickness of the inert metal oxide substrate layer.

The metal electrode may be anodised in any suitable electrolyte solution. For example, the electrolyte solution may be an aqueous solution comprising an inorganic acid, for example phosphoric acid ($H_3PO_4$), or comprising an organic acid, for example citric acid, tartaric acid, lactic acid, acetic acid, malonic acid, or mixtures thereof.

In other embodiments, the metal substrate may be subjected to an oxidative pre-treatment step.

The inert ceramic substrate may be used to immobilise a parent radioisotope within a generator as described herein for use in capturing a population of daughter radioisotope.

In one embodiment, the process comprises contacting the surface of the inert ceramic substrate with an aqueous solution comprising a surfactant prior to depositing a solution comprising a parent radioisotope species on the surface of an inert ceramic substrate, which can lower the surface tension of the deposited solution such that it has a low enough contact angle with the surface of the inert ceramic substrate to enable it to readily wet and spread across the surface without the need for physical agitation. Any suitable surfactant may be used, such as anionic surfactants, non-ionic surfactants or mixtures thereof.

Preparation and Deposition of Radioisotope Solution

The process comprises depositing a solution comprising a parent radioisotope species on the surface of an inert ceramic substrate. The solution may comprise any liquid effective for holding parent radioisotope species in solution therein to allow for efficient loading and dispersion of the parent radioisotope species on the surface of the inert ceramic substrate.

In one embodiment, the solution is an aqueous solution or an alcohol solution. It will be appreciated that an aqueous solution comprises an amount of water. For example, the aqueous solution may comprise water and one or more water miscible solvents, such as an alcohol solvent. It will be appreciated that an alcohol solution comprises an amount of alcohol.

In one embodiment, the aqueous solution comprises an alcohol solvent (i.e. is an aqueous alcohol solution). The aqueous solution may comprise an alcohol solvent in an amount of between about 20% v/v to about 50% v/v based on the total volume of the aqueous solution. The aqueous solution may comprise (in % v/v based on the total volume of the aqueous solution) an alcohol solvent in an amount of at least about 5, 10, 15, 20, 25, 30, 35, 40, 45, 50, 55, 60, 65 or 70. The aqueous solution may comprise (in % v/v based on the total volume of the aqueous solution) an alcohol solvent in an amount of less than about 70, 65, 60, 55, 50, 45, 40, 35, 30, 25, 20, 15, 10 or 5. The aqueous solution may comprise an alcohol solvent in a range provided by any two of these upper and/or lower values, for example between about 20% v/v to about 50% v/v based on the total volume of the aqueous solution. The alcohol solvent may be a polar solvent. The polar solvent may be capable of chemically complexing with radioisotope. The alcohol solvent may be selected from methanol, ethanol, isopropanol, n-propanol, n-butanol, and mixtures thereof. It will be appreciated that the use of a suitable solvent described herein can lower the surface tension of the solution such that it has a low enough contact angle with the surface of the inert ceramic substrate to enable it to readily wet and spread across the surface without the need for physical agitation.

The aqueous solution may further comprise a surfactant, which according to some embodiments or examples described herein, can lower the surface tension of the solution such that it has a low enough contact angle with the surface of the inert ceramic substrate to enable it to readily wet and spread across the surface without the need for physical agitation. In one embodiment, the surfactant may comprise an anionic surfactant, a non-ionic surfactant, or a mixture thereof. In one embodiment, the surfactant is a polyethoxylated fatty acid ester or an ethoxylated aliphatic alcohol. The aqueous solution may comprise a surfactant in an amount of between about 1% v/v to about 10% v/v based on the total volume of the aqueous solution. The aqueous solution may comprise (in % v/v based on the total volume of the aqueous solution) a surfactant in an amount of at least about 0.5, 1, 1.5, 2, 2.5, 3, 3.5, 4, 4.5, 5, 5.5, 6, 6.5, 7, 8, 9 or 10. The aqueous solution may comprise (in % v/v based on the total volume of the aqueous solution) a surfactant in an amount of less than about 10, 9, 8, 7, 6, 5, 4.5, 4, 3.5, 3, 2.5, 2, 1.5, 1 or 0.5. The aqueous solution may comprise a surfactant in a range provided by any two of these upper and/or lower values, for example between about 1% v/v to about 5% v/v based on the total volume of the aqueous solution.

The radioisotope species may be provided as a water-soluble salt or hydrate thereof selected from one or more of hydroxides, halides, nitrates, acetates, sulfates, phosphates, perchlorates, ammonium compounds and anionic oxo-metallate compounds. In one embodiment, the radioisotope species is provided in solvated or complexed cationic form. In one embodiment the radioisotope species is provided in an anionic oxo-metallate form (e.g. $[ThO(HPO_4)_3(H_2PO_4)]^{5-}$).

In one embodiment, the radioisotope species may be a thorium compound or a radium compound, or a combination thereof. In one embodiment, the radioisotope species is a thorium species. The thorium radioisotope species may be selected from at least one of $^{227}Th$, $^{228}Th$ and $^{232}Th$, or combination thereof. In one embodiment, the radioisotope species is a thorium species provided as a nitrate salt or hydrate thereof, for example thorium nitrate $(Th(NO_3)_4)$. In one embodiment, the radioisotope species is a radium species. The radium radioisotope species may be selected from at least one of $^{224}Ra$ and $^{228}Ra$, or a combination thereof. In one embodiment, the radioisotope species is a radium species provided as a nitrate salt or hydrate thereof, for example radium nitrate. The radium radioisotope species may be provided as a hydrated cation thereof, for example, the hydrated radium divalent cation $(Ra(H_2O)_n^{2+})$ In one embodiment, the radioisotope species is provided in the solution at a concentration of between about 0.00001 M (mol/L) to about 1 M, between about 0.00001 M to about 0.5 M, or between about 0.0001 M to about 0.5 M. The radioisotope species may be provided in the solution at a concentration (in M) of at least about 0.00001, 0.0001, 0.001, 0.002, 0.004, 0.006, 0.008, 0.01, 0.05, 0.1, 0.15, 0.2, 0.25, 0.3, 0.35, 0.4, 0.45, 0.5, 0.8 or 1. The radioisotope species may be provided in the solution at a concentration (in M) of less than about 1, 0.8, 0.5, 0.45, 0.4, 0.35, 0.3, 0.25, 0.2, 0.15, 0.1, 0.05, 0.01, 0.008, 0.006, 0.004, 0.002 0.001, 0.0001 or 0.00001. The radioisotope species concentration may be a range provided by any two of these upper and/or lower values, for example between about 0.005 M and about 0.05 M.

The process may further comprise adding a precipitating agent to the radioisotope solution. The precipitating agent may be added to the radioisotope solution prior to deposition of the solution on the surface of the inert ceramic substrate. Alternatively, the precipitating agent may be added to the radioisotope solution after it has been deposited on the surface of the inert ceramic substrate and prior to the heating at step b). The precipitating agent induces precipitation of the radioisotope from the solution prior to the heating at step b), for example as a solid amorphous compound of the radioisotope species, e.g. as a hydroxide of the radioisotope species.

Any suitable precipitating agent can be used. In one embodiment, the precipitating agent is oxalic acid, a hydroxide base (e.g. NaOH, $NH_4OH$, LiOH), or a halide salt. In one embodiment, the precipitating agent is oxalic acid. The concentration of precipitating agent (e.g. oxalic acid) may be between about 0.01 mM (millimoles/L) and about 100 mM. The concentration of precipitating agent (in mM) may be at least about 0.01, 0.05, 0.1, 0.15, 0.2, 0.25, 0.3, 0.35, 0.4, 0.5, 1, 2, 3, 5, 10, 15, 20, 30, 50, 60, 80 or 100, 150, 200, 250, 300, 350, 400, 450 or 500. The concentration of precipitating agent (in mM) may be less than about 500, 450, 400, 350, 300, 250, 200, 150, 100, 80, 60, 50, 30, 20, 15, 10, 5, 3, 2, 1, 0.5, 0.45, 0.4, 0.35, 0.3, 0.25, 0.2, 0.15, 0.1, 0.05, or 0.01. The precipitating agent concentration may be a range provided by any two of these upper and/or lower values.

The process may further comprise raising the pH of the radioisotope solution to a more alkaline pH. By raising the pH of the solution, according to some embodiments or examples described herein, the soluble radioisotope species/ions coalesce into an amorphous hydroxide which can provide improved binding and immobilising on or within the inert ceramic substrate. In this example, the amorphous hydroxide subsequently converts to an oxide phase of the radioisotope upon heating, as described herein. Examples of suitable additives used to raise the pH include one or more alkaline compounds, including for example aqueous ammonium hydroxide. Other solid amine compounds can be used, for example hexamethylene tetramine. The pH of the solution may be raised prior to the heating of the inert ceramic substrate, for example by dropping a suitable solution (e.g. ammonium hydroxide solution) onto the deposited radioisotope solution on the surface of the inert ceramic substrate. Alternatively, the radioisotope solution may be deposited onto the surface of an inert ceramic substrate wherein a solution having a higher pH (e.g. more alkaline pH than the pH of the radioisotope solution) has previously been deposited. Alternatively, the pH of the radioisotope solution may be raised prior to deposition on the surface of the inert ceramic substrate.

In other embodiments, the process may further comprise lowering the pH of the radioisotope solution to a more acidic pH. By lowering the pH of the solution, according to some embodiments or examples described herein, the soluble radioisotope species/ions remain well solvated and able to disperse without substantial aggregation across the surface of the inert ceramic substrate. In this example, the radioisotope subsequently exchanges with lattice ions of the ceramic substrate compound, as described herein. Examples of suitable additives used to lower the pH include one or more acidic compounds, including for example aqueous nitric acid, perchloric acid, trifluoroacetic acid.

The solution comprising the radioisotope species may be deposited on the surface of an inert ceramic substrate by any suitable means, for example by dropping or micropipetting. Once deposited, the inert ceramic substrate may be heated as described herein (e.g. ex-situ deposition and heating). Alternatively, the inert ceramic substrate may be immersed/submerged in the parent radioisotope solution, which can then be heated as described herein (e.g. in-situ deposition and heating). It will be appreciated that the amount of solution can be modified depending on the size of the inert ceramic substrate surface, for example to maximise output of the daughter isotope product. In some embodiments, the inert ceramic substrate is agitated to facilitate spreading of the deposited radioisotope solution and/or mixing of the precipitating agent and/or alkaline and/or acidic additive described herein.

Heat Treatment of Inert Ceramic Substrate

The process comprises heating the inert ceramic substrate to a temperature effective to bind at least some of the parent radioisotope on or near the surface of the inert ceramic substrate. It will be appreciated that heating the inert ceramic substrate will in turn heat the solution deposited on the surface of the inert ceramic substrate.

In one embodiment, the heating of the inert ceramic substrate forms a heat-treated radioisotope surface layer on the surface of the inert ceramic substrate. In one embodiment, the heating of the inert ceramic substrate forms a radioisotope-doped layer within the surface of the inert ceramic substrate. In one embodiment, the heating of the inert ceramic substrate forms one or more solid compound phases, crystalline phases or amorphous phases of radioisotope bound on the surface of the inert ceramic substrate. The inert ceramic substrate, radioisotope surface layer, heat-treated radioisotope surface layer, solid compound phases, crystalline phases and amorphous phases are described herein.

The heating step may be viewed as a thermal treatment of the solution comprising the solubilised radioisotope species and/or precipitated radioisotope species, wherein the radioisotope species is thermally decomposed into parent radioisotope that is immobilised on or within the inert ceramic substrate and is thus tightly bound on or within the inert ceramic substrate. Furthermore, the heat treatment can facilitate radioisotope ion exchange with, and ion migration and interspersion within the atomic lattice of the inert ceramic substrate thereby forming a layer on the surface, as described herein.

The inert ceramic substrate at step b) may be heated to a temperature effective to bind radioisotope on or near the surface of the inert ceramic substrate. The heating may be at a temperature effective to convert the radioisotope species in the solution (e.g. the dissolved and/or precipitated radioisotope species) into mobile parent radioisotope that exchanges or otherwise chemically interacts with, and becomes immobilised on or within the inert ceramic substrate. It will be appreciated that the heating of the solution may also comprise heating the inert ceramic substrate. The temperature may be selected depending on the radioisotope species. In one embodiment, the heating at step b) is at a temperature of between about 100° C. to about 650° C. The heating at step b) may be at a temperature (in C) of at least about 100, 200, 220, 240, 260, 280, 300, 320, 325, 340, 360, 380, 400, 450, 500, 550, 600 or 650. The heating at step b) may be at a temperature (in C) of less than about 650, 600, 550, 500, 450, 400, 380, 360, 340, 325, 320, 300, 280, 260, 240, 220, 200 or 100. The heating temperature may be a range provided by any two of these upper and/or lower values, for example between about 200° C. to about 650° C., or between about 300° C. to about 500° C., for example about 325° C.

The heating temperature may be obtained at a heating rate of at least 1, 1.5, 2, 2.5, 2, 3.5, 3, 4, 4.5, 5, 6, 7, 8, 9 or 10° C./min. The heating temperature may be obtained at a heating rate of less than 10, 9, 8, 7, 6, 5, 4.5, 4, 3.5, 3, 2.5, 2, 1.5 or 1° C./min. The heating rate may be a range provided by any two of these upper and/or lower values.

The inert ceramic substrate at step b) may be heated for a period of time effective to bind radioisotope on or near the surface of the inert ceramic substrate. The heating may be for a period of time effective to convert the radioisotope species in the solution into mobile parent radioisotope that exchanges or otherwise chemically interacts with, and becomes immobilised on or within the surface of the inert ceramic substrate (e.g. as a radioisotope surface layer comprising radioisotope ions tightly bound to the inert ceramic substrate, for example as one or more solid compound phases (e.g. amorphous and/or crystalline phases, which can form following favourable chemical exchange of the radioisotope with the atomic lattice of the inert ceramic substrate).

In one embodiment, the heating at step b) is for a period of time of between about 10 minutes to about 24 hours. The heating at step b) may be for a period of time of at least about 10, 15, 20, 25, 30, 35, 40, 45, 50, 55, 60, 65, 70, 75, 80, 85, or 90 (minutes), 2, 3, 4, 5, 6, 8, 10, 12, 14, 16, 18, 20, 22 or 24 hours. The heating at step b) may be for a period of time of less than about 24, 22, 20, 18, 16, 14, 12, 10, 8, 6, 5, 4, 3, 2 (hours), 90, 85, 80, 75, 70, 65, 60, 55, 50, 45, 40, 35, 30, 25, 20, 15 or 10 (minutes). The heating time may be a range provided by any two of these upper and/or lower values, for example between about 10 minutes to about 6 hours or between about 1 hour to about 3 hours. In one embodiment, the heating at step b) may be for a period of between about 10 minutes to about 180 minutes. The heating at step b) may be for a period of time (in minutes) of at least about 10, 15, 20, 25, 30, 35, 40, 45, 50, 55, 60, 65, 70, 75, 80, 85, 90, 100, 120, 150 or 180. The heating at step b) may be for a period of time (in minutes) of less than about 180, 150, 120, 100, 90, 85, 80, 75, 70, 65, 60, 55, 50, 45, 40, 35, 30, 25, 20, 15 or 10. The heating time may be a range provided by any two of these upper and/or lower values. Other heating temperatures and times to those recited herein are also envisaged, including longer heating times.

The heating at step b) may be a two-step heating process. In one embodiment, the heating at step b) comprises (i) heating the inert ceramic substrate and deposited solution at a first temperature and for a period of time effective to dry the solution on the surface of the inert ceramic substrate (e.g. to drive off/remove/evaporate the aqueous or alcoholic solution) and then (ii) heating the inert ceramic substrate comprising residual radioisotope to a second temperature and for a period of time effective for parent radioisotope ions to exchange with and/or chemically interact with the inert ceramic substrate.

For step (i), the inert ceramic substrate may be heated to a first temperature of between about 60° C. to about 130° C. The inert ceramic substrate at step (i) may be heated to a first temperature (in C) of at least about 50, 60, 80, 100, 110, 120, 130, 140 or 150. The inert ceramic substrate at step (i) may be heated to a first temperature (in C) of less than about 150, 140, 130, 120, 110, 100, 80, 60 or 50. The inert ceramic substrate at step (i) may be heated to a first temperature in a range provided by any two of these upper and/or lower values, for example between about 50° C. to about 150° C., or between about 80° C. to about 120° C., e.g. about 85° C. For step (ii), the inert ceramic substrate may be heated to a second temperature of between about 200° C. to about 650° C. The inert ceramic substrate at step (ii) may be heated to a second temperature (in ° C.) of at least about 200, 220, 240, 260, 280, 300, 320, 325, 340, 360, 380 or 400. The inert ceramic substrate at step (ii) may be heated to a second temperature (in C) of less than about 400, 380, 360, 340, 325, 320, 300, 280, 260, 240, 220 or 200. The inert ceramic substrate at step (ii) may be heated to a second temperature in a range provided by any two of these upper and/or lower values, for example between about 300° C. to about 500° C., e.g. about 325° C. Other heating temperatures are also envisaged.

For step (i) the inert ceramic substrate may be heated at temperature for a period of time (in minutes) of at least about 5, 10, 15, 20, 25, 30, 35, 40, 45, 50, 55, and 60. The heating at step (i) may be for a period of time (in minutes) of less than about 60, 55, 50, 45, 40, 35, 30, 25, 20, 15 or 10. The heating time at step (i) may be a range provided by any two of these upper and/or lower values, for example between about 10 minutes to about 60 minutes e.g. about 30 minutes. For step (ii), the inert ceramic substrate may be heated a temperature for at least about 10, 15, 20, 25, 30, 35, 40, 45, 50, 55, 60, 65, 70, 75, 80, 85, or 90 (minutes), 2, 3, 4, 5, 6, 8, 10, 12, 14, 16, 18, 20, 22 or 24 hours. The heating at step (ii) may be for a period of time of less than about 24, 22, 20, 18, 16, 14, 12, 10, 8, 6, 5, 4, 3, 2 (hours), 90, 85, 80, 75, 70, 65, 60, 55, 50, 45, 40, 35, 30, 25, 20, 15 or 10 (minutes). The heating time at step (ii) may be a range provided by any two of these upper and/or lower values, for example between about 10 minutes to about 6 hours, between about 1 hour to about 3 hours, or between about 10 minutes to about 180 minutes. Other heating temperatures and times to those recited herein for step (i) and step (ii) are also envisaged, including longer heating times.

The heating may be performed using a suitable furnace (e.g. muffle furnace), kiln, autoclave, microwave reactor, or hotplate. Alternatively, the heating may be performed using spray pyrolysis or spray drying of the deposited solution on the surface inert ceramic substrate.

In one embodiment, the heating at step b) comprises heating the inert ceramic substrate under pressure, for example in a sealed vessel (e.g. an autoclave or microwave reactor) such that the solution does not substantially evaporate during the heating. In one embodiment, the inert ceramic substrate is heated under pressure at a temperature of between about 100° C. to about 240° C. The inert ceramic substrate may be heated under pressure at a temperature (° C.) of at least about 100, 110, 120, 130, 140, 150, 160, 170, 180, 190, 200, 210, 220, 240, 260, 280 or 300. The inert ceramic substrate may be heated under pressure at a temperature (C) of less than about 300, 280, 260, 240, 220, 210, 200, 190, 180, 170, 160, 150, 140, 130, 120, 110 or 100. A range may be provided by any two of these upper and/or lower values, for example between about 100 to about 220. In one embodiment, the inert ceramic substrate may be heated under pressure for a period of time of between 2 h to about 24 h. The inert ceramic substrate may be heated under pressure for a period of time (in h) of at least about 0.1, 0.5, 1, 2, 3, 4, 5, 6, 8, 10, 12, 14, 16, 18, 20, 22 or 24. The inert ceramic substrate may be heated under pressure for a period of time (in h) of less than about 24, 22, 20, 18, 16, 14, 12, 10, 8, 6, 5, 4, 3, 2, 1, 0.5 or 0.1. A range may be provided by any two of these upper and/or lower values, for example between about 0.1 h to about 18 h. It is understood that in some embodiments a substantial overpressure is required to prevent solution evaporating at elevated temperatures.

The heating of the inert ceramic substrate under pressure may be a two-stepped process, for example (i) heating the inert ceramic substrate and deposited solution under pressure at a first temperature and for a period of time effective to drive ion exchange between the radioisotope ions and ions of the inert ceramic substrate, and then (ii) heating the inert ceramic substrate and radioisotope species under pressure to a second temperature and for a period of time effective for parent radioisotope ions to undergo further exchange with and/or chemically interact with the inert ceramic substrate. In some embodiments or examples, the heating under pressure at step (i) may generate small regions of an intermediate solid radioisotope compound on the surface of the inert ceramic substrate, which are thermally decomposed during the heating under pressure at (ii) to form one or more crystalline phases of radioisotope that are bound onto the inert ceramic substrate. The heating under pressure at step (i) and/or step (ii) in may also facilitate radioisotope ion exchange with the ceramic substrate surface.

The inert ceramic substrate comprising immobilised parent radioisotope can be used to generate daughter radioisotope using the processes, systems and generators described below.

Radioisotope Generator

The present disclosure also provides a radioisotope generator for capturing a population of daughter radioisotope. In one aspect or embodiment, there is provided a radioisotope generator defining a chamber for capturing a population of daughter radioisotope, the chamber configured to house an inert ceramic substrate according to any aspects, embodiments or examples described herein. As described herein, the inert ceramic substrate housed within the chamber may comprise parent radioisotope immobilised on or within the inert ceramic substrate in an amount effective to generate (i.e. produce) a medically useful dose of daughter radioisotope through a chain of spontaneous decay from the parent radioisotope via a gaseous intermediate radioisotope. It will therefore be understood that a chamber housing the inert ceramic substrate both produces (i.e. generates) and captures a population of daughter radioisotope.

In one embodiment, the chamber comprises a collection surface and is configured to house the inert ceramic substrate in the chamber with the radioisotope surface layer facing the collection surface for collecting at least some of the emanated gaseous intermediate isotope on the collection surface for a period of time effective to decay into daughter radioisotope.

The collection surface may be any surface capable of collecting and retaining emanated gaseous intermediate radioisotope, for example a removable dish/tray/container. The collection surface may comprise any suitable material. In one embodiment, the collection surface may comprise or consist of a cellulose material (such as cellulose filter paper), a polymeric material (e.g. PTFE), or glass. Alternatively, the collection surface may the inner wall of a collection chamber described herein.

In one embodiment, the chamber may be configured to house the inert ceramic substrate wherein the radioisotope surface layer is in line-of-sight configuration with the collection surface. It will be understood that "line-of-sight" communication refers to a configuration where the collection surface and radioisotope surface layer are at some point in time in view of each other within the chamber without any obstacle (such as a closed valve or retractable seal) in between, to allow for the efficient transport of emanated gaseous intermediate radioisotope. In some embodiments, the chamber may be configured with one or more valves, seals and/or closures configured to temporarily physically isolate/separate the inert ceramic substrate from the collection surface, such as when the daughter radioisotope is extracted from the collection surface. While such physical separation of the inert ceramic substrate from the collection surface temporarily disrupts the line-of-sight communication, it will be understood that when collection of emanated radioisotope is occurring, the chamber is configured at some point to provide line-of-sight communication between the radioisotope surface layer and the collection surface. In other words, such line-of-sight configuration does not preclude the presence of one or more closures, seals and/or valves being present in the chamber to temporarily physically isolate/separate the inert ceramic substrate from the collection surface, such as when daughter radioisotope is being extracted from the collection surface.

In a related embodiment, the chamber may be configured to house the inert ceramic substrate wherein the radioisotope surface layer substantially faces downwards to enable gravity assisted collection of at least some of the emanated gaseous intermediate on the collection surface. For example, the chamber may be configured to house the inert ceramic substrate above the collection surface. Again, this does not preclude the presence of one or more closures, seals or valves being present in the chamber to physically isolate/separate the inert ceramic substrate from the collection surface, such as when daughter radioisotope is being extracted from the collection surface.

In one embodiment, the radioisotope generator further comprises a carrier gas inlet port configured to introduce a carrier gas into the chamber to facilitate transfer of emanated gaseous intermediate radioisotope away from the inert ceramic substrate onto the collection surface.

In one embodiment, the radioisotope generator further comprises a vacuum pump configured to apply a vacuum and evacuate the chamber to facilitate transfer of emanated gaseous intermediate radioisotope away from the inert ceramic substrate onto the collection surface.

In one embodiment, the radioisotope generator further comprises a fluid delivery system configured to introduce a collection fluid into the chamber to collect daughter radioisotope from the collection surface. In some embodiments, the radioisotope generator comprises one or more valves, seals and/or closures configured to physically isolate/separate the inert ceramic substrate from the collection surface within the chamber, such as when the daughter radioisotope is extracted from the collection surface. In a related embodiment, the radioisotope generator further comprises a collection fluid outlet port configured to transfer the collection fluid comprising daughter radioisotope from the chamber.

The radioisotope generator may further comprise a system for washing daughter radioisotope product from the collection surface into a product vessel, using an appropriate collection fluid. For example, the generator may further comprise a fluid delivery system configured to introduce a collection fluid into the chamber to collect daughter radioisotope which has deposited on the collection surface. The fluid delivery system may comprise a collection fluid reservoir coupled to a collection fluid inlet port via a collection fluid inlet valve for introducing the collection fluid into the chamber. The fluid delivery system may be controlled by a collection fluid inlet valve operably configured to intermittently open to introduce a series of pulses of the collection fluid through the collection fluid inlet port into the chamber.

The generator may further comprise a collection fluid outlet port configured to transfer the collection fluid comprising the daughter radioisotope from the chamber, for example into a product vessel. The collection fluid outlet port may be controlled by a collection fluid outlet valve and/or pump operably configured to intermittently open to extract the collection fluid comprising the daughter radioisotope from the chamber.

In one embodiment, the generator, in use, is configured to produce at least one medical (e.g. clinical or pre-clinical) dose of daughter radioisotope within a 24 hour period, for example at least 1, 2, 3, 4 or 5 medical doses of daughter radioisotope within a 24 hour period.

In one embodiment, the generator, in use, may be configured to produce at least one medical dose of daughter radioisotope (e.g. $^{212}$Pb) of at least about 1, 2, 5, 10, 50, 60, 90, 120, 150, 200, 250, 300, 400, 500, 600, 700, 800, 900 or 1,000 MBq. In another embodiment, the generator, in use, may be configured to produce at least one medical dose of daughter radioisotope (e.g. $^{212}$Pb) of less than about 1,000, 900, 800, 700, 600, 500, 400, 300, 250, 200, 150, 120, 90, 60, 50, 10, 5, 2 or 1. In one embodiment, the generator, in use, may be configured to produce at least one medical dose of daughter radioisotope (e.g. $^{212}$Pb) of at least about 50, 70, 100, 120, 140, 160, 180 or 200 MBq. The generator, in use, may be configured to produce at least one medical dose of daughter radioisotope (e.g. $^{212}$Pb) in a range provided by any two of these upper and/or lower values, for example between about 50 MBq to about 200 MBq.

In some embodiments or examples, the chamber may comprise a source chamber described herein configured to house the inert ceramic substrate and a collection chamber described herein comprising the collection surface. The chambers may further comprise one or more closures, seals and/or valves separating the source chamber and the collection chamber. In one embodiment or example, there is provided a radioisotope generator for capturing a population of daughter radioisotope generated through a chain of spontaneous decay from a parent radioisotope, the generator comprising: a) a source chamber configured to immobilise a parent radioisotope that decays to emanate a gaseous intermediate radioisotope; b) a collection chamber configured to collect emanated gaseous intermediate radioisotope from the source chamber and retaining the gaseous intermediate radioisotope for a period of time effective to decay into a daughter radioisotope; and c) an optional inter-chamber transfer valve separating the source chamber and collection chamber which is operably configured to transfer the emanated gaseous intermediate radioisotope from the source chamber into the collection chamber.

In one embodiment, the parent radioisotope is immobilised on or within an inert ceramic substrate described herein. For example, the source chamber may be configured to house an inert ceramic substrate comprising immobilised radioisotope as described herein.

The generator may further comprise a carrier gas inlet port configured to introduce a carrier gas stream into the source chamber to facilitate transfer of the emanated gaseous intermediate radioisotope from the source chamber through the inter-chamber transfer valve into the collection chamber, for example to pressurise the source chamber to provide a pressure differential between the source chamber and the collection chamber. The carrier gas inlet port may be controlled by a carrier gas inlet valve operably configured to intermittently open to introduce the carrier gas as a series of pulses into the source chamber.

The generator may further comprise a vacuum pump configured to apply a vacuum to and evacuate the collection chamber to facilitate the transfer of the emanated gaseous intermediate radioisotope from the source chamber through the inter-chamber transfer valve into the collection chamber, for example to evacuate the collection chamber to a vacuum to provide a pressure differential between the collection chamber and the source chamber. The evacuation of the collection chamber may also facilitate the introduction of collection fluid from the collection fluid reservoir into the collection chamber. The evacuation of the collection chamber to a vacuum may be controlled by a vacuum valve operably configured to intermittently open to apply the vacuum to the collection chamber.

The generator may further comprise d) a system for washing daughter radioisotope product from the collection chamber into a product vessel, using an appropriate collection fluid. For example, the generator may further comprise a fluid delivery system configured to introduce a collection fluid into the collection chamber to collect daughter radioisotope which has deposited on the inner wall of the collection chamber. The fluid delivery system may comprise a collection fluid reservoir coupled to a collection fluid inlet port via a collection fluid inlet valve for introducing the collection fluid into the collection chamber. The fluid delivery system may be controlled by a collection fluid inlet valve operably configured to intermittently open to introduce a series of pulses of the collection fluid through the collection fluid inlet port into the collection chamber.

The generator may further comprise a collection fluid outlet port configured to transfer the collection fluid comprising the daughter radioisotope from the collection chamber, for example into a product vessel. The collection fluid outlet port may be controlled by a collection fluid outlet valve and/or pump operably configured to intermittently open to extract the collection fluid comprising the daughter radioisotope from the collection chamber.

Figure 8:
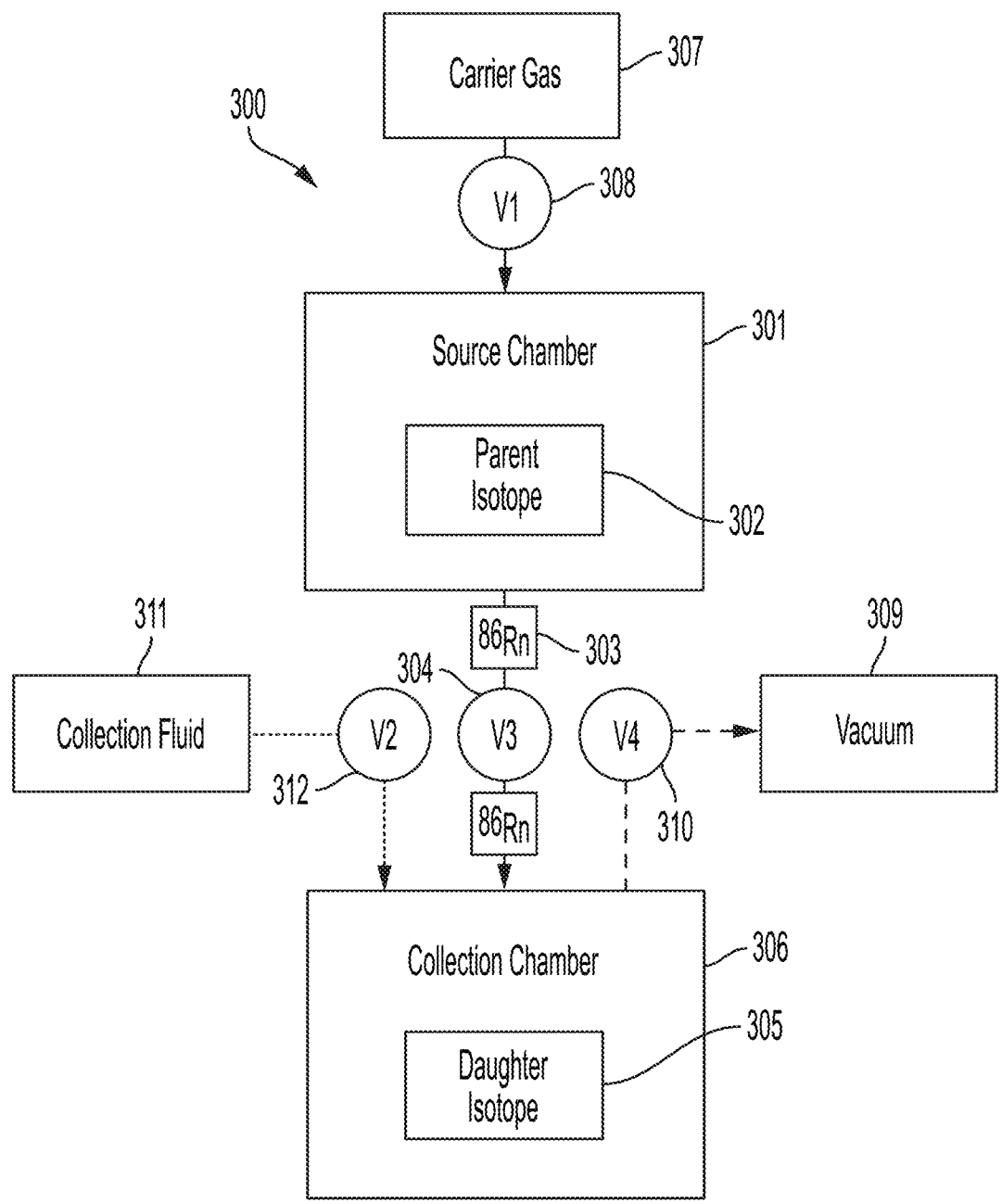
FIG. 8 shows one embodiment of the generator used to generate and capture a population of daughter radioisotope.
Figure 9:
FIG. 9 shows one example of valve operation parameters for transferring the emanated gaseous intermediate radioisotope from the source chamber to the collection chamber, and for collecting daughter radioisotope product.

The features of the generator are described herein, including aspects, examples and embodiments described under the headings "Process for generating daughter radioisotope" and "Collection of daughter radioisotope", and including for example at FIG. 8 and the related description herein.

Systems

The present disclosure also provides a system for producing and capturing a population of daughter radioisotope generated through a chain of spontaneous decay from a parent radioisotope, the system comprising: a) a generator; and b) an inert ceramic substrate according to any aspect, embodiment or examples described herein.

In one aspect or embodiment, there is provided a system for producing and capturing a population of daughter radioisotope generated through a chain of spontaneous decay from a parent radioisotope, the system comprising: a) a radioisotope generator defining a chamber for producing and capturing a population of daughter radioisotope; and b) an inert ceramic substrate according to any aspect, embodiment or examples described herein housed in the chamber.

The inert ceramic substrate may be an inert ceramic substrate according to any aspects, embodiments, or examples described herein. The radioisotope generator may be a generator according to any aspects, embodiments, or examples described herein.

In one embodiment, the radioisotope generator defines a chamber comprising a source chamber and a collection chamber, each of which is described herein.

It will be appreciated that any aspects, embodiments or examples of the radioisotope generator, process and/or inert ceramic substrate as described herein may form one or more aspects, embodiments or examples of the system.

Process for Generating Daughter Radioisotope

Figure 7:
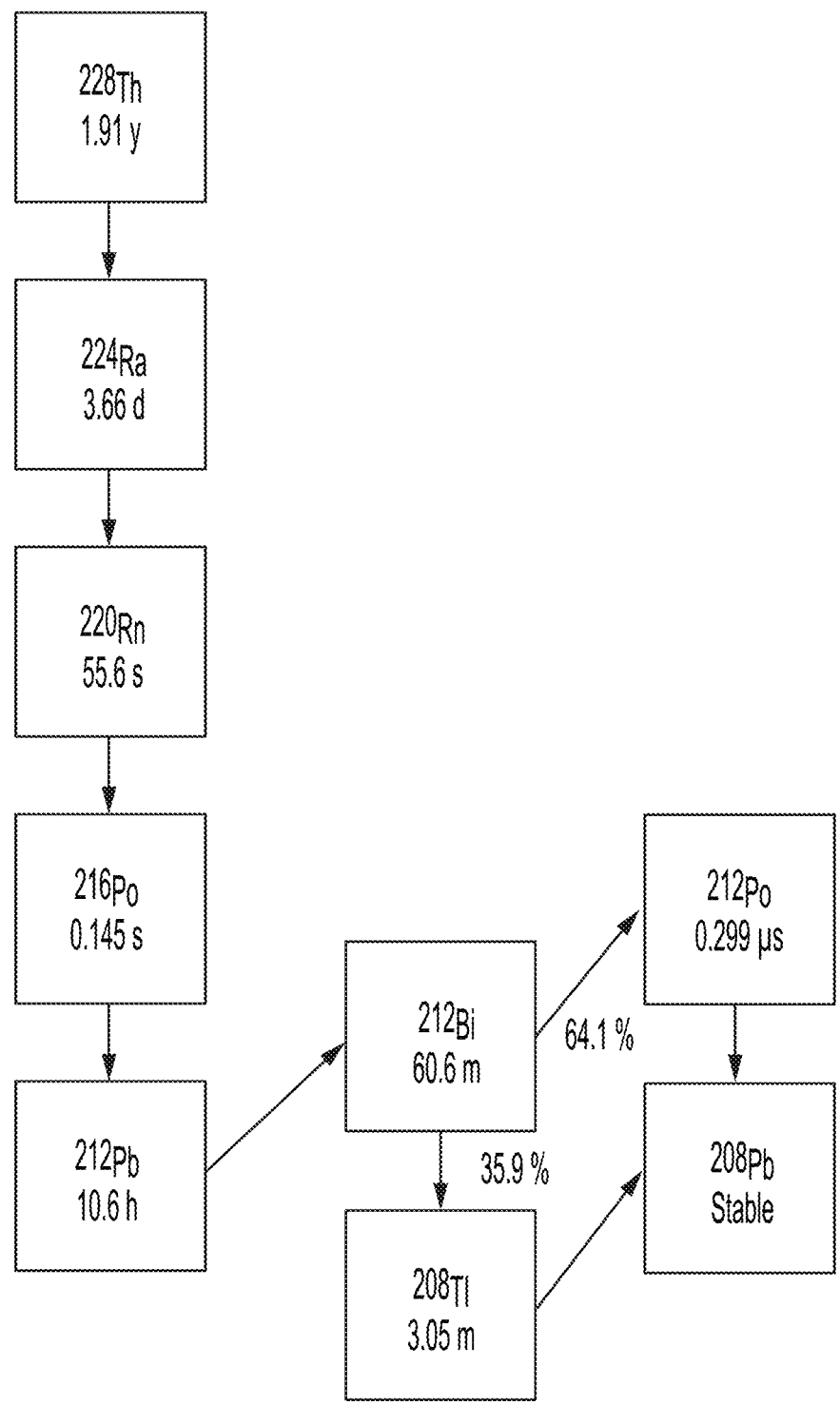
FIG. 7 shows a radioactive decay series for thorium-228 ($^{228}$Th) which in some embodiments comprise the radioisotope of the present disclosure.

The present disclosure also relates to processes for capturing a population of daughter radioisotope. The daughter radioisotope produced by the process described herein is generated through a chain of spontaneous decay from a parent radioisotope via a gaseous intermediate radioisotope. An example of a spontaneous radioactive decay series relating to the present disclosure is provided in FIG. 7, illustrating the $^{228}$Th decay series.

In one embodiment or example, there is provided a process for capturing a population of daughter radioisotope comprising: a) allowing for the emanation of a gaseous intermediate radioisotope generated through a chain of spontaneous decay from a parent radioisotope immobilised on or within an inert ceramic substrate according to aspect, examples or embodiments described herein; and b) collecting at least some of the gaseous intermediate radioisotope for a period of time effective to decay into daughter radioisotope.

The process may comprise a radioisotope generator according to any aspects, embodiments or examples described herein or a system according to any aspects, embodiments or examples described herein.

In some embodiments or examples, the process comprises immobilising the parent radioisotope in a source chamber and transferring the gaseous intermediate radioisotope to a separate collection chamber in which it naturally decays into a daughter radioisotope. In particular, the present inventors have identified that such separation minimises contamination of the daughter radioisotope with the parent radioisotope, providing downstream advantages such as a purer clinical product.

In another aspect or embodiment, there is provided a process for capturing a population of daughter radioisotope generated through a chain of spontaneous decay from a parent radioisotope, the process comprising the steps of:
a) immobilising a parent radioisotope within a source chamber that decays to emanate a gaseous intermediate radioisotope; and
b) transferring at least some of the gaseous intermediate radioisotope from the source chamber through an inter-chamber transfer valve to a collection chamber, wherein the gaseous intermediate radioisotope is retained in the collection chamber for a period of time effective to decay into a daughter radioisotope.

In one embodiment, the inter-chamber transfer valve is intermittently opened to generate a non-continuous transfer of the emanated gaseous intermediate radioisotope from the source chamber into the collection chamber.

The processes described herein can be performed using a radioisotope generator. Referring to FIG. 8, one exemplary embodiment of the generator (300) for isolating and capturing the population of daughter radioisotope is shown. The generator comprises a source chamber (301) that is configured to house an immobilised parent radioisotope source contained therein (302), for example $^{228}$Th. The source chamber (301) is configured to allow gaseous intermediate radioisotope generated where parent radioisotope is immobilised (302) to emanate into the base of the source chamber (301). The emanated gaseous intermediate radioisotope may be a pure gas or may be in a carrier gas (307) which has been introduced (see solid arrow) into the source chamber (301) through a carrier gas inlet port controlled by the opening of a carrier gas inlet valve (308). In one example, the emanated gaseous intermediate radioisotope is $^{220}$Rn. The carrier gas (307) can facilitate the capture of the emanated gaseous intermediate radioisotope.

The generator comprises a collection chamber (306) as a separate component to the source chamber (301). An inter-chamber transfer valve (304) can be used to transfer the emanated gaseous intermediate radioisotope (303) from the source chamber (301) to the collection chamber (306). The inter-chamber transfer valve (304) is configured to be either left open or be intermittently opened to transfer the emanated gaseous intermediate radioisotope (303) from the source chamber into the collection chamber (306), for example as a non-continuous flow (e.g. a series of pulses). It will be appreciated that when the inter-chamber transfer valve (304) is intermittently opened, it moves between a closed state in which the collection chamber (306) is substantially not in gaseous communication with the source chamber (301) (i.e. substantially isolated from one another) and an open state in which the collection chamber (306) and source chamber are in gaseous communication with each other.

The transfer of the gaseous intermediate radioisotope through the inter-chamber transfer valve (304) may be driven by a pressure differential as described herein. The pressure differential may be generated by the introduction of a carrier gas (307) into the source chamber (301). Additionally or alternatively, the pressure differential may be generated by evacuating the collection chamber (306) using the vacuum pump (309), which can be controlled by a vacuum valve (310) (see dashed arrow).

The collection chamber (306) is configured to retain the emanated gaseous intermediate radioisotope for a period of time effective for it to decay into a daughter radioisotope (305), for example high purity $^{212}$Pb product radioisotope that accumulates on the internal walls of the collection chamber (306). The daughter radioisotope (305) can be readily collected, for example with a collection fluid (311) which is introduced into the collection chamber (306). A collection fluid inlet valve (312) can be used to control the introduction of the collection fluid (311) into the collection chamber (306), and for example can be intermittently opened to introduce a series of pulses (see dotted arrow) of the collection fluid (311) into the collection chamber (306). The collection chamber comprises a collection fluid outlet port configured to extract the collection fluid and daughter radioisotope. The extraction of the collection fluid through the collection fluid outlet valve can be controlled by a fluid outlet valve.

The inter-chamber transfer valve (304), carrier gas inlet valve (308), vacuum valve (310), collection fluid inlet valve (312) and/or fluid outlet valve (not shown) may be electronically controlled solenoid valves. Various computer-controlled devices can be utilized to automate and control the timing of the opening of one or more valves described herein, to automate any suitable aspect of radioisotope production and to provide consistent production results in each generation cycle.

Source Chamber Housing Parent Radioisotope

The source chamber is configured to house an immobilised parent radioisotope, wherein the parent radioisotope decays to emanate a gaseous intermediate radioisotope. The source chamber is also configured to facilitate the collection of the intermediate gaseous radioisotope. The parent radioisotope may be immobilised on a substrate, wherein the substrate is housed within the source chamber. In one embodiment, the parent radioisotope is immobilised on or within an inert ceramic substrate described herein. For example, the source chamber may be configured to house an inert ceramic substrate comprising immobilised radioisotope as described herein.

In one embodiment, the parent radioisotope is an alpha-emitter i.e. it decays by emitting an alpha particle (i.e. helium nucleus) and thereby transforms into a different atomic nucleus with a mass number that is reduced by four and an atomic number that is reduced by two.

Although any parent radioisotope may be used as long as they decay through a gaseous intermediate radioisotope, in one embodiment, the parent radioisotope is an isotope of thorium or radium or a combination thereof. In one embodiment, the parent radioisotope is a thorium radioisotope. The thorium radioisotope may be selected from at least one of $^{227}$Th and $^{228}$Th, or a combination thereof. In one embodiment, the parent radioisotope radioisotope is radium. The radium radioisotope may be selected from at least one of $^{224}$Ra and $^{228}$Ra, or a combination thereof.

The immobilised parent radioisotope may be provided in an amount effective to generate a gaseous intermediate isotope for subsequent decay and collection of a daughter radioisotope (e.g. as a product). The parent radioisotope ion may be provided in an amount effective to generate a medically useful amount (e.g. pre-clinically and/or clinically useful amount) of daughter radioisotope. For example, the parent radioisotope ion may be provided in an amount effective to generate a medical dose of daughter radioisotope (e.g. $^{212}$Pb) of at least about 50, 70, 100, 120, 140, 160, 180 or 200 MBq.

The source chamber may be any suitable size or configuration capable of housing an immobilised parent radioisotope therein. The source chamber may be constructed with a material that is not subject to radiolytic breakdown so as not to be affected by gamma radiation or the emanated gaseous intermediate radioisotope, for example one or more metallic materials such as tungsten, tantalum, lead, stainless steel, including alloys and/or cermet materials comprising the same. The source chamber may also be constructed with one or more ceramic materials, such as cubic zirconia, or polymers with high level of radiation tolerance (e.g. polyimide). Such materials are radiolytically stable and not substantially damaged upon contact with alpha particles emitted during decay of the immobilised parent radioisotope or by the gaseous intermediate radioisotope, or by associated gamma photon fluxes.

Non-Continuous Transfer of Gaseous Intermediate Radioisotope

The process described herein comprises immobilising the parent radioisotope in a source chamber and transferring the gaseous intermediate radioisotope to a separate collection chamber in which it naturally decays into a daughter radioisotope. At least according to some embodiments or examples described herein, such separation minimises contamination of the daughter radioisotope with the parent radioisotope, providing downstream advantages such as a safer and/or more active clinical product.

The gaseous intermediate radioisotope is transferred from the source chamber through an inter-chamber transfer valve to a collection chamber. In one embodiment, the inter-chamber transfer valve may be intermittently opened for a period of time effective to transfer the emanated gaseous radioisotope from the source chamber into the collection chamber.

In relation to the operation of one or more valves described herein, the terms "intermittently opened" and "intermittent opening" refer to the opening and closing of the valve a number of times to generate a non-continuous flow of a medium (e.g. gas or liquid) through the valve. In other words, the valve moves between a closed state and an open state a number of times. For example, in relation to the intermittent opening of the inter-chamber transfer valve, the valve may be configured in a normally-closed position and is repeatedly opened a number of times to provide an interrupted, non-continuous transfer of the emanated gaseous intermediate radioisotope from the source chamber into the collection chamber. The intermittent opening of the valve may comprise any number of valve openings, for example at least 2, 5, 10, 20, 30, 40, 50, 100, 200, 300, 400, 500, 600, 700, 800, 900, 1000, 1100, 1200, 1300, 1400, 1500, 1600, 1700, 1800, 1900, 2000, 2200, 2400, 2600, 2800, 3000, 3400, 3800, 4200, 4600, 5000, 5400, 5800, 6200, 7000, 8000, 9000 or 10,000 times prior to extraction and collection of daughter radioisotope from the collection chamber.

At least according to some embodiments or examples described herein, the present inventors have found that the radiochemical purity and/or activity yield of the collected daughter radioisotope can be improved when the inter-chamber transfer valve is intermittently opened to effect a non-continuous transfer of the gaseous intermediate radioisotope from the source chamber to the collection chamber.

When the inter-chamber transfer valve is in each open state, it is open for a period of time effective to transfer the gaseous intermediate radioisotope from the source chamber to the collection chamber. In one embodiment, the inter-chamber transfer valve is in each open state for a period of time of between about 10 milliseconds to about 500 milliseconds. The inter-chamber transfer valve in each open state may be open for a period of time (in milliseconds) of at least about 10, 20, 40, 60, 80, 100, 120, 140, 160, 180, 200, 240, 260, 280, 300, 350, 400, 450 or 500. The inter-chamber transfer valve may be open for a period of time (in milliseconds) of less than about 500, 450, 400, 350, 300, 280, 260, 240, 200, 180, 160, 140, 120, 100, 80, 60, 40, 20 or 10. The inter-chamber transfer valve in each open state may be open for a period of time in a range provided by any two of these upper and/or lower ranges, for example between about 20 milliseconds to about 90 milliseconds.

The intermittent opening of the inter-chamber transfer valve may occur at any suitable interval to achieve the optimum non-continuous transfer of the gaseous intermediate radioisotope. For example, the interval between each opening of the inter-chamber transfer valve may be configured to allow sufficient time for the gaseous intermediate radioisotope to grow in concentration in the source chamber between each opening.

In one embodiment, the inter-chamber transfer valve may be intermittently opened at an interval of between about 3 seconds to about 10 minutes after the previous valve opening to provide the non-continuous transfer of the emanated gaseous radioisotope from the source chamber to the collection chamber. The inter-chamber transfer valve may be intermittently opened at an interval of at least about 3, 4, 5, 6, 8, 10, 15, 30, 60 seconds, 1.5, 2, 2.5, 3, 3.5, 4, 4.5, 5, 5.5, 6, 6.5, 7, 7.5, 8, 8.5, 9, 9.5 or 10 minutes after the previous valve opening. The inter-chamber transfer valve may be intermittently opened at an interval of less than about 10, 9.5, 9, 8.5, 8, 7.5, 7, 6.5, 6, 5.5, 5, 4.5, 4, 3.5, 3, 2.5, 2, 1.5 minutes, 60, 30, 15, 10, 8, 6, 5, 4 or 3 seconds after the previous valve opening. The interval after the previous valve opening may be in a range provided by any two of these upper and/or lower values, for example between about 10 seconds to about 10 minutes, about 1 minute to about 10 minutes, about 1 minute to about 5 minutes, for example about 2 minutes.

The intermittent opening of the inter-chamber transfer valve may comprise any number of valve openings. In one embodiment, the inter-chamber transfer valve may be intermittently opened between 50 times to 10,000 times prior to extraction and collection of daughter radioisotope from the collection chamber. The inter-chamber transfer valve may be intermittently opened at least 50, 100, 200, 300, 400, 500, 600, 700, 800, 900, 1000, 1100, 1200, 1300, 1400, 1500, 1600, 1700, 1800, 1900, 2000, 2200, 2400, 2600, 2800, 3000, 3400, 3800, 4200, 4600, 5000, 5400, 5800, 6000, 6200, 7000, 8000, 9000 or 10,000 times prior to extraction and collection of daughter radioisotope from the collection chamber. The inter-chamber transfer valve may be intermittently opened less than 10,000, 9000, 8000, 7000, 6000, 6200, 5800, 5400, 5000, 4600, 4200, 3800, 3400, 3000, 2800, 2600, 2400, 2200, 2000, 1900, 1800, 1700, 1600, 1500, 1400, 1300, 1200, 1000, 900, 800, 700, 600, 500, 400, 300, 200, 100 or 50 times prior to the extraction and collection of daughter radioisotope from the collection chamber. The inter-chamber transfer valve may be opened a number of times in a range provided by any two of these upper and/or lower values.

According to some embodiments or examples described herein, the present inventors have identified that the overall yield of daughter radioisotope can be optimised by adjusting the interval at which the inter-chamber transfer valve is intermittently opened. For example, the intermittent opening of the inter-chamber transfer valve described herein allows for the "shot-wise" transfer of gaseous intermediate radioisotope from the source chamber and its "step-wise" accumulation in in the collection chamber. Advantages of this "shot-wise" transfer of gaseous intermediate radioisotope can include, for example, less surface area over which the gaseous intermediate radioisotope is distributed and from which the daughter radioisotope product must be collected, thus reducing the overall size/footprint of the generator compared to larger generators that rely on continuous transfer and capture of gaseous intermediate radioisotope from resin-based ion exchange source chambers. At least according to some embodiments or examples described herein, the non-continuous transfer of $^{220}$Rn (e.g. emanated gaseous intermediate radioisotope) as a series of pulses also allows for the isolation and collection of $^{212}$Pb having low levels of the stable daughter isotope $^{208}$Pb (which is the final daughter isotope in the natural decay of $^{228}$Th/$^{212}$Pb, see FIG. 7). The shot-wise accumulation and transfer of $^{220}$Rn can lead to lower levels of $^{208}$Pb in the $^{212}$Pb product because it takes less time to accumulate a useful clinical dose in the collection chamber, which, in turn, is made possible by the intermittent opening of the inter-chamber transfer valve. As it is impossible to chemically separate $^{212}$Pb from $^{208}$Pb, capturing a product having more $^{212}$Pb than $^{208}$Pb can lead to more effective radiolabelling of targeting ligands, higher specific activity doses and ultimately a more effective and safer therapeutic for use in radiopharmacy (e.g. in radioligand therapy).

The inter-chamber transfer valve may be intermittently opened at an interval effective to provide daughter radioisotope in the collection chamber having an activity (in MBq) of between about 20 to about 500. The inter-chamber transfer valve may be intermittently opened at an interval effective to provide daughter radioisotope in the collection chamber having an activity (in MBq) of at least about 20, 40, 60, 80, 100, 120, 140, 160, 180, 200, 220, 240, 260, 280, 300, 340, 380, 420, 460 or 500. The inter-chamber transfer valve may be intermittently opened at an interval effective to provide daughter radioisotope in the collection chamber having an activity (in MBq) of less than about 500, 460, 420, 380, 340, 300, 280, 260, 240, 220, 200, 180, 160, 140, 120, 100, 80, 60, 40, or 20. A range may be provided by any two of these upper and/or lower values.

In one embodiment, the activity of the gaseous intermediate radioisotope in the source chamber is between about 5% to 99% of the activity of the parent radioisotope prior to opening of the inter-chamber transfer valve. The activity of the gaseous intermediate radioisotope in the source chamber may be at least about 5, 10, 15, 20, 25, 30, 35, 40, 45, 50, 55, 60, 65, 70, 75, 80, 85, 90 or 99% of the activity of the parent radioisotope prior to opening of the inter-chamber transfer valve. The activity of the gaseous intermediate radioisotope in the source chamber may be less than 99, 95, 90, 85, 80, 75, 70, 65, 60, 55, 50, 45, 40, 35, 30, 25, 20, 15, 10 or 5% of the activity of the parent radioisotope prior to opening of the inter-chamber transfer valve. The % activity may be a range provided by any two of these upper and/or lower values.

In one embodiment, the activity of the gaseous intermediate radioisotope in the source chamber is between about 10 kBq to about 1,000,000 kBq prior to opening of the inter-chamber transfer valve. The activity of the gaseous intermediate radioisotope (in kBq) in the source chamber may be at least about 10, 100, 1000, 10,000, 100,000, 200,000, 300,000, 400,000, 500,000, 600,000, 700,000, 800,000, 900,000 or 1,000,000 prior to opening of the inter-chamber transfer valve. The activity of the gaseous intermediate radioisotope (in kBq) in the source chamber may be less than 1,000,000, 900,000, 800,000, 700,000, 600,000, 500,000, 400,000, 300,000, 200,000, 100,000, 10,000, 1000, 100 or 10 prior to opening of the inter-chamber transfer valve. The activity may be a range provided by any two of these upper and/or lower values, for example between about 100 kBq to about 500,000 kBq. The activity may be estimated from the theoretical secular equilibrium activity derivable from the activity of the parent radioisotope on the inert ceramic substrate, described herein.

Figure 10:
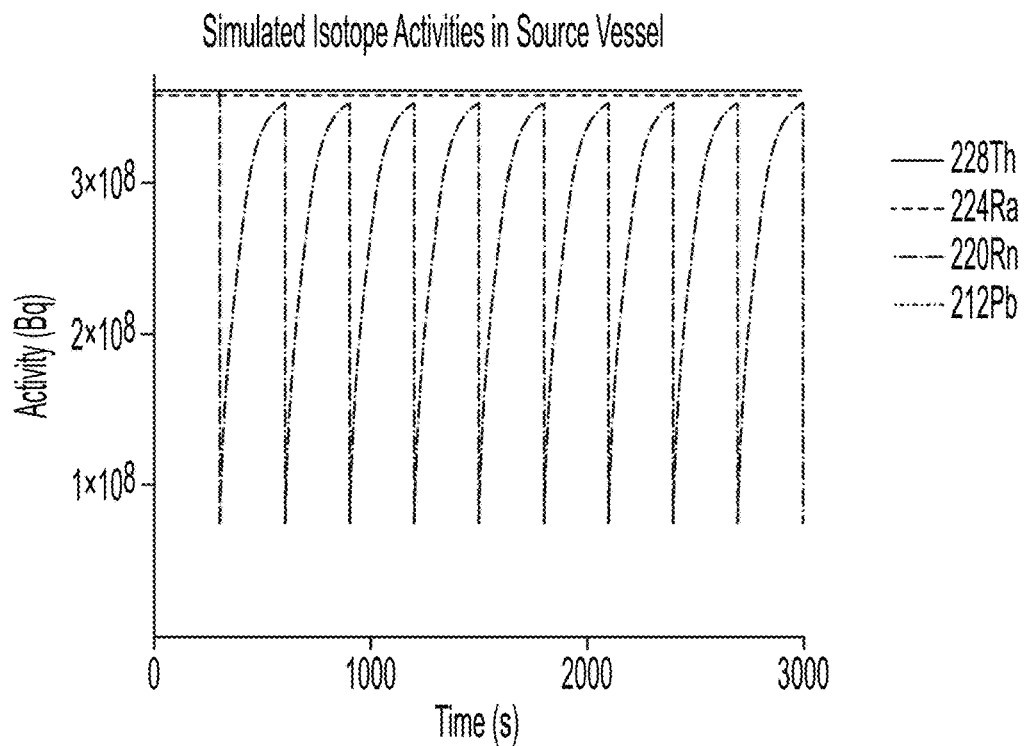
FIG. 10 shows simulated activities of the radioisotope thorium-228 ($^{228}$Th); radium-224 ($^{224}$Ra); and radon-220 ($^{220}$Rn) in the source chamber over a 3000 second period.

In one embodiment, the inter-chamber transfer valve is opened when a) the activity of the gaseous intermediate radioisotope is at or close to a rate of in-growth that is between about 20% to about 80% of the maximum in-growth rate of the gaseous intermediate radioisotope in the source chamber (i.e. the point in time when the inter-chamber transfer valve is opened to transfer gaseous intermediate radioisotope from the source chamber is at or close to a point that is between about 20% to about 80% of the steepest part of the temporal in-growth curve of the gaseous intermediate isotope from the parent radioisotope; see FIG. 10). Alternatively or additionally, the inter-chamber transfer valve is opened when b) when the gaseous intermediate radioisotope held in the collection chamber following the preceding transfer has decayed to a point that is between about 20% to about 80% of the steepest part of the temporal in-growth curve of the gaseous intermediate isotope from the parent radioisotope.

According to some embodiments or examples described herein, by opening the inter-chamber transfer valve only at intervals which correspond to the optimal activity of the gaseous intermediate radioisotope in the source chamber in terms of maximum in-growth rate balanced with holding the previously transferred gaseous intermediate radioisotope in the collection chamber for an optimal period of time to allow it to decay into the daughter radioisotope, the overall yield of daughter radioisotope is increased. An example of an interval that exploits the maximum in-growth rate of gaseous radioisotope activity in the source chamber is opening the inter-chamber transfer valve between about 1 minute to about 5 minutes, for example about 2 minutes, after the previous valve opening.

Pressure Driven and Vacuum Driven Gas Transfer Events

In one embodiment, the transfer of the emanated gaseous intermediate radioisotope through the inter-chamber transfer valve is driven by a pressure differential between the source chamber and the collection chamber. The pressure differential may be provided by a positive pressure applied to the source chamber, and/or a negative pressure (i.e. vacuum) being applied to the collection chamber.

In one embodiment, the pressure differential is generated by pressurising the source chamber with a carrier gas, and wherein opening the inter-chamber transfer valve provides a pressure driven gas transfer event of the carrier gas comprising the emanated gaseous intermediate radioisotope from the source chamber to the collection chamber. In this embodiment, upon opening the inter-chamber transfer valve, the pressure differential "pushes" the emanated gaseous intermediate radioisotope from the source chamber through the inter-chamber transfer valve to the collection chamber.

In one embodiment, the source chamber may be pressurised with the carrier gas prior to each pressure driven gas transfer event (e.g. before each pressure driven gas transfer event, the source chamber is pressurised). Alternatively, the pressure generated in the source chamber may be effective to provide two or more pressure driven gas transfer events (e.g. two or more pressure driven gas transfer events after a single pressurisation of the source chamber).

In one embodiment, the carrier gas is introduced into the source chamber as a stream through a carrier gas inlet port. In one embodiment, the introduction of the carrier gas into the source chamber is controlled by a carrier gas inlet valve which is intermittently opened to introduce a non-continuous flow of the carrier gas into the source chamber. In one embodiment, a carrier gas is introduced into the source chamber through a carrier gas inlet port. In one embodiment, the introduction of the carrier gas into the source chamber is controlled by a carrier gas inlet valve which is intermittently opened to introduce a non-continuous flow of the carrier gas into the source chamber. The source chamber is connected to a carrier gas inlet port configured to introduce the carrier gas into the source chamber through the intermittently opened carrier gas inlet valve. The introduction of the carrier gas into the source chamber may also pressurise the source chamber.

The carrier gas may comprise any inert gas that does not react with the radioisotope (i.e. parent, intermediate and/or daughter radioisotope) and/or with constituent components of the generator. In one embodiment, the carrier gas comprises argon, helium, nitrogen, or mixtures thereof. In one embodiment, the carrier gas comprises argon.

In one embodiment, the source chamber may be pressurised with the carrier gas (307) to a pressure of between about 0.5 bar to about 8 bar (gauge) prior to opening the inter-chamber transfer valve to provide the pressure driven gas transfer event of the carrier gas comprising the emanated gaseous intermediate radioisotope from the source chamber to the collection chamber. The source chamber may be pressurised with the carrier gas to a pressure (in bar) to at least about 0.5, 1, 1.5, 2, 2.5, 3, 3.5, 4, 4.5, 5, 5.5, 6, 6.5, 7, 7.5, or 8 prior to opening the inter-chamber transfer valve to provide the pressure driven gas transfer event of the carrier gas comprising the emanated gaseous intermediate radioisotope from the source chamber to the collection chamber. The source chamber may be pressurised with the carrier gas to a pressure (in bar) of less than about 8, 7.5, 7, 6.5, 6, 5.5, 5, 4.5, 4, 3.5, 3, 2.5, 2, 1.5, 1 or 0.5 prior to opening the inter-chamber transfer valve to provide the pressure driven gas transfer event of the carrier gas comprising the emanated gaseous intermediate radioisotope from the source chamber to the collection chamber. The pressure may be in a range provided by any two of these upper and/or lower values, for example between about 0.5 bar to about 5 bar, about 0.75 bar to about 4 bar, or about 1 bar to about 2.5 bar prior to opening the inter-chamber transfer valve to provide the pressure driven gas transfer event of the carrier gas comprising the emanated gaseous intermediate radioisotope from the source chamber to the collection chamber, e.g. about 1.7 bar.

When the carrier gas inlet valve (308) is in each open state, it is open for a period of time effective to pressurise the source chamber with the carrier gas stream, for example between about 10 milliseconds to about 300 milliseconds. The carrier gas inlet valve in each open state may be open for a period of time (in milliseconds) of at least about 10, 20, 40, 60, 80, 100, 120, 140, 160, 180, 200, 240, 260, 280 or 300. The carrier gas inlet valve in each open state may be open for a period of time (in milliseconds) of less than about 300, 280, 260, 240, 200, 180, 160, 140, 120, 100, 80, 60, 40, 20 or 10. The carrier gas inlet valve in each open state may be open for a period of time in a range provided by any two of these upper and/or lower ranges, for example between about 80 milliseconds to about 140 milliseconds, e.g. about 120 milliseconds.

In another embodiment, the pressure differential is generated by evacuating the collection chamber to a vacuum, and wherein opening the inter-chamber transfer valve provides a vacuum driven gas transfer event of the emanated gaseous intermediate radioisotope from the source chamber to the collection chamber. In this embodiment, upon opening the inter-chamber transfer valve, the pressure differential "pulls" the emanated gaseous intermediate radioisotope from the source chamber through the inter-chamber transfer valve to the collection chamber.

In one embodiment, the collection chamber may be evacuated to a vacuum prior to each vacuum driven gas transfer event (e.g. before each vacuum driven gas transfer event, the collection chamber is evacuated). Alternatively, the vacuum generated in the collection chamber may be effective to provide two or more vacuum driven gas transfer events (e.g. two or more vacuum driven gas transfer events after a single evacuation of the collection chamber).

The evacuation of the collection chamber to a vacuum may be provided by a vacuum pump (309) configured to apply a vacuum to and evacuate the collection chamber to create the pressure differential. The vacuum applied to the collection chamber may be controlled by a vacuum valve (310) which is intermittently opened to evacuate the collection chamber and create the pressure differential.

The collection chamber may be evacuated to a vacuum effective to create the pressure differential between the source chamber and the collection chamber. In one embodiment, the collection chamber is evacuated to a vacuum of between about 1 mbar to about 400 mbar prior to opening the inter-chamber transfer valve to provide the vacuum driven gas transfer event of the emanated gaseous intermediate radioisotope from the source chamber to the collection chamber. The collection chamber may be evacuated to a vacuum (in mbar) of at least about 1, 2, 5, 10, 20, 40, 60, 80, 100, 150, 100, 200, 250, 300, 350 or 400 prior to opening the inter-chamber transfer valve to provide the vacuum driven gas transfer event of the emanated gaseous intermediate radioisotope from the source chamber to the collection chamber. The collection chamber may be evacuated to a vacuum (in mbar) of less than 400, 350, 300, 250, 200, 150, 100, 80, 60, 40, 20, 10, 5, 2 or 1 prior to opening the inter-chamber transfer valve to provide the vacuum driven gas transfer event of the emanated gaseous intermediate radioisotope from the source chamber to the collection chamber. The vacuum may be a range provided by any two of these upper and/or lower amounts, for example between about 5 mbar to about 80 mbar prior to opening the inter-chamber transfer valve to provide the vacuum driven gas transfer event of the emanated gaseous intermediate radioisotope from the source chamber to the collection chamber.

In one embodiment, the collection chamber may be evacuated to a vacuum for a period of time of between about 0.5 second to about 20 seconds prior to opening the inter-chamber transfer valve. The collection chamber may be evacuated to a vacuum for a period of time (in seconds) of at least about 0.5, 1, 2, 3, 4, 6, 8, 10, 12, 14, 16, 18 or 20 prior to opening the inter-chamber transfer valve. The collection chamber may be evacuated to a vacuum for a period of time (in seconds) of less than about 20, 18, 16, 14, 12, 10, 8, 6, 4, 3, 2, 1 or 0.5 prior to opening the inter-chamber transfer valve. The evacuation time may be a range provided by any two of these upper and/or lower values, for example between about 0.8 second to about 3 seconds.

In one embodiment, the intermittent opening of the inter-chamber transfer valve comprises at least one sequence of gas transfer events, the at least one sequence of gas transfer events comprising at least one pressure driven gas transfer event and at least one vacuum driven gas transfer event of the gaseous intermediate radioisotope from the source chamber to the collection chamber. The at least one pressure driven gas transfer event and at least one vacuum driven gas transfer event can occur in any order. A sequence of gas transfer events may also be called a "cycle" or "generation cycle" as described herein.

Figure 11:
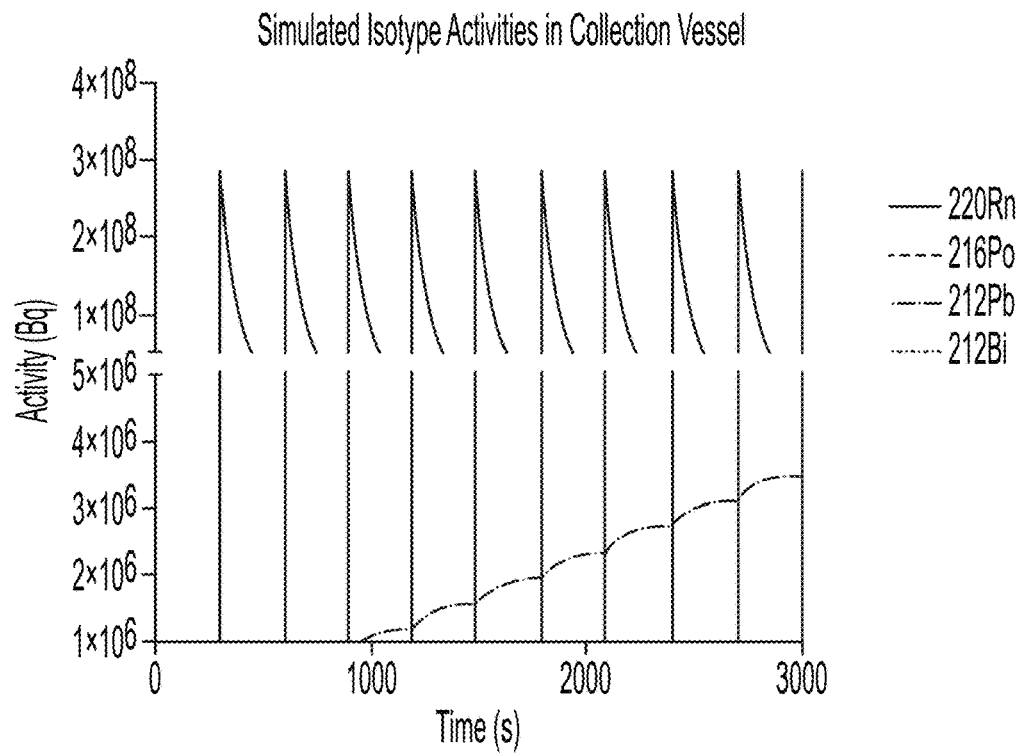
FIG. 11 shows simulated corresponding activities of the radioisotope radon-220 ($^{220}$Rn) and lead-212 ($^{212}$Pb) in the collection chamber over a 3000 second period with 200 MBq $^{228}$Th held in the source chamber (in equilibrium with (radium-224 ($^{224}$Ra)). Time points directly correlate with those shown in FIG. 10.

In one embodiment, the at least one sequence of gas transfer events consists of between 2 to 20 pressure driven gas transfer events prior to or following a vacuum driven gas transfer event. The at least one sequence of gas transfer events may consist of at least 2, 3, 4, 5, 6, 7, 8, 9, 10, 11, 12, 13, 14, 15, 16, 17, 18, 19 or 20 pressure driven gas transfer events prior to or following a vacuum driven gas transfer event. The at least one sequence of gas transfer events may consist of less than 20, 19, 18, 17, 16, 15, 14, 13, 12, 11, 10, 9, 8, 7, 6, 5, 4, 3 or 2 pressure driven gas transfer events prior to or following a vacuum driven gas transfer event. The number of pressure driven gas transfer events prior to or following a vacuum driven gas transfer event in a sequence may be a range provided by any two of these upper and/or lower values, for example between 2 to 10, 2 to 8, 2 to 6, or 2 to 5 pressure driven gas transfer events prior to or following a vacuum driven gas transfer event. According to some embodiments or examples described herein, a sequence of gas transfer events consisting of two or more pressure driven gas transfer events prior to or following a vacuum driven gas transfer event can achieve optimal yields of daughter radioisotope in the collection chamber, as shown in FIG. 11.

The number of pressure driven gas transfer events for every vacuum driven gas transfer event can also be provided as a ratio. In one embodiment, the at least one sequence of gas transfer events has a pressure driven gas transfer event to vacuum driven gas transfer event ratio of between 1:1 to 20:1. The at least one sequence of gas transfer events may have a pressure driven gas transfer event to vacuum driven gas transfer event ratio of at least about 1:1, 2:1, 3:1, 4:1, 5:1, 6:1, 7:1, 8:1, 9:1, 10:1, 11:1, 12:1, 13:1, 14:1, 15:1 16:1 17:1 18:1, 19:1 or 20:1. The at least one sequence of gas transfer events may have a pressure driven gas transfer event to vacuum driven gas transfer event ratio of less than 20:1, 19:1, 18:1, 17:1, 16:1, 15:1, 14:1, 13:1, 12:1, 10:1, 9:1, 8:1, 7:1, 6:1, 5:1, 4:1, 3:1, 2:1 or 1:1. The pressure driven gas transfer event to vacuum driven gas transfer event ratio may be a range provided by any two of these upper and/or lower values, for example between 1:1 to 20:1, for example between 1:1 to 10:1, 1:1 to 8:1, 1:1 to 6:1, or 1:1 to 5:1. for example between 1:1 to 10:1, 1:1 to 8:1, 1:1 to 6:1, or 1:1 to 5:1. The sequence of gas transfer events may be repeated any number of times. In one embodiment, the sequence of gas transfer events described herein may be repeated between 10 times to 2000 times prior to the extraction and collection of daughter radioisotope from the collection chamber. The sequence of gas transfer events described herein may be repeated at least 10, 50, 100, 150, 200, 300, 400, 500, 600, 700, 800, 900, 1000, 1100, 1200, 1300, 1400, 1500, 1600, 1700, 1800, 1900 or 2000 times.

According to some embodiments or examples described herein, the present inventors have identified that transferring the gaseous intermediate radioisotope through the intermittently opened inter-chamber transfer valve using a combination of pressure driven gas transfer events and vacuum driven gas transfer events can increase the overall yield of daughter radioisotope in the collection chamber. For example, one or more advantages can be provided by using a combination of pressure driven gas transfer events and vacuum driven gas transfer events, including: a) the generator does not need to be engineered to manage very high gas pressures and/or; b) large amounts of gaseous intermediate isotope are not lost to the vacuum system during vacuum driven gas transfer events and are retained in the daughter isotope collection chamber. According to some embodiments or examples described herein, increasing the pressure driven gas transfer event to vacuum driven gas transfer event ratio can increase the overall daughter radioisotope activity in the collection chamber, as shown in FIG. 11.

The interval between each gas transfer event may be between about 3 seconds to about 10 minutes after the previous gas transfer event to provide the non-continuous transfer of the emanated gaseous radioisotope from the source chamber to the collection chamber. The interval between each gas transfer event of the intermittent opening may be at least about 3, 4, 5, 6, 8, 10, 15, 30, 60 seconds, 1.5, 2, 2.5, 3, 3.5, 4, 4.5, 5, 5.5, 6, 6.5, 7, 7.5, 8, 8.5, 9, 9.5 or 10 minutes after the previous gas transfer event. The interval between each gas transfer event of the intermittent opening may be less than about 10, 9.5, 9, 8.5, 8, 7.5, 7, 6.5, 6, 5.5, 5, 4.5, 4, 3.5, 3, 2.5, 2, 1.5 minutes, 60, 30, 15, 10, 8, 6, 5, 4 or 3 seconds after the previous gas transfer event. The interval between each gas transfer event of the intermittent opening may be in a range provided by any two of these upper and/or lower values, for example between about 10 seconds to about 10 minutes, about 1 minute to about 10 minutes, about 1 minute to about 5 minutes, for example about 2 minutes after the previous gas transfer event.

According to some embodiments or examples described herein, it will be appreciated that only one pressure driven gas transfer event or vacuum driven gas transfer event occurs each time the inter-chamber transfer valve is opened. By way of example only, the intermittent opening may comprise at least one sequence of gas transfer events consisting of five pressure driven gas transfer events prior to or following a vacuum driven gas transfer event, each gas transfer event separated by an interval of 2 minutes. In this example, every sixth opening of the inter-chamber transfer valve is a vacuum driven gas transfer event, wherein each opening of the inter-chamber transfer valve occurs 2 minutes after the previous valve opening. The sequence can then be repeated any number of times until the desired activity of daughter radioisotope in the collection chamber is reached, following which it can be collected and extracted.

As described herein, the parent radioisotope decays to emanate a gaseous intermediate radioisotope. The gaseous intermediate radioisotope may be radon-219 ($^{219}$Rn), radon-220 ($^{220}$Rn), or a mixture thereof. In one embodiment, the gaseous intermediate radioisotope is $^{220}$Rn.

Capture of Daughter Radioisotope

Once transferred from the source chamber to the collection chamber, the gaseous intermediate radioisotope is retained in the collection chamber for a period of time effective for it to spontaneously decay into a daughter radioisotope. The amount of daughter radioisotope produced during the decay period may be useful for medical applications. The collection chamber is described herein, including under the "Radioisotope extraction" aspect and embodiment of the present disclosure.

In one embodiment, the process described herein generates daughter radioisotope in the collection chamber having an activity of between about 5% to about 80% of the parent radioisotope activity immobilised in the source chamber. The process described herein may generate daughter radioisotope in the collection chamber having an activity of at least about 5, 10, 20, 30, 40, 50, 60, 70 or 80% of the parent radioisotope activity within a 24 hour period. The process may generate daughter radioisotope in the collection chamber having an activity of less than about 80, 70, 60, 50, 40, 30, 20, 10 or 5% of the parent radioisotope activity. A percent activity range may be provided by any two of these upper and/or lower values.

Although the daughter radioisotope can be any decay product of a gaseous intermediate radioisotope described herein, and depends on the parent radioisotope immobilised in the source chamber, in some embodiments, the daughter radioisotope is a lead radioisotope or a bismuth radioisotope, or a mixture thereof, for example lead-211 ($^{211}$Pb) and/or bismuth-211 ($^{211}$Bi), lead-212 ($^{212}$Pb) and/or bismuth-212 ($^{212}$Bi), or a mixture thereof and including daughter radioisotopes thereof. In one embodiment, the daughter radioisotope is $^{212}$Pb or $^{211}$Pb, or a mixture thereof.

The daughter radioisotope can be used as a therapeutic radioisotope in radiolabelled drug applications. The daughter radioisotope can be generated in the collection chamber in clinically relevant amounts. As such, it will be appreciated that the daughter radioisotope can be a product which can be extracted from the collection chamber, collected and used, as described herein.

In one embodiment, the process generates at least one medical (e.g. clinical or pre-clinical) dose of daughter radioisotope within a 24 hour period, for example at least 1, 2, 3, 4 or 5 medical doses of daughter radioisotope within a 24 hour period. The process may generate a medical dose of daughter radioisotope (e.g. $^{212}$Pb) of at least about 50, 70, 100, 120, 140, 160, 180 or 200 MBq.

In one embodiment, the process further comprises a step of recovering at least some of the daughter radioisotope, for example from a collection surface or chamber described herein. The recovery of at least some of the daughter radioisotope is described herein, including under the "Radioisotope extraction" aspect and embodiment of the present disclosure. The daughter radioisotope may be recovered from the collection chamber after a requisite number of cycles of gas transfer event sequences have been performed and/or once the activity of the daughter radioisotope in the collection chamber reaches a desired level.

In one embodiment, the recovered daughter radioisotope can be used in a radiopharmacy. For example, the recovered daughter radioisotope may be conjugated to a targeting molecule for use as a radiopharmaceutical agent such as in radioligand therapy. Various applications and uses of the recovered daughter radioisotope are described herein, including under the "Applications" aspect and embodiment of the present disclosure.

The parent radioisotope, gaseous intermediate radioisotope and daughter radioisotope used/generated in the process are described herein. In one embodiment relating to the process, the parent radioisotope is a thorium radioisotope selected from at least one of thorium-227 ($^{227}$Th) and thorium-228 ($^{228}$Th). In one embodiment relating to the process, the gaseous intermediate radioisotope is a radon radioisotope selected from at least one of radon-219 ($^{219}$Rn) and radon-220 2 ($^{220}$Rn) In one embodiment relating to the process, the daughter radioisotope is a lead radioisotope selected from at least one of lead-211 ($^{211}$Pb) or lead-212 ($^{212}$Pb).

Collection of Daughter Radioisotope

The present inventors have developed a process to recover daughter radioisotope that has grown-in and accumulated (e.g. has been captured/collected) on the collection surface described herein, including where the collection surface is the inner wall of a collection chamber described herein. By introducing a collection fluid to gather daughter radioisotope which has accumulated on the collection surface (as a result of spontaneous decay of the gaseous intermediate radioisotope), the daughter radioisotope can be extracted from the collection surface in a fluid which can be readily used as a product, for example in clinical radiopharmacy applications such as radioligand therapy.

In one aspect or embodiment, there is provided a process for recovering a population of daughter radioisotope from a collection surface in a chamber of a radioisotope generator, the process comprising the steps of:
 a) introducing a collection fluid into the chamber through a collection fluid inlet port to collect the daughter radioisotope which has deposited on the collection surface; and
 b) extracting the collection fluid comprising the daughter radioisotope from the chamber through a collection fluid outlet port to recover the daughter radioisotope.

In one aspect or embodiment, there is provided a process for recovering a population of daughter radioisotope captured in a collection chamber, the process comprising the steps of:
 a) introducing a collection fluid into the collection chamber through a collection fluid inlet port to collect the daughter radioisotope which has deposited on the inner wall of the collection chamber; and
 b) extracting the collection fluid comprising the daughter radioisotope from the collection chamber through a collection fluid outlet port to recover the daughter radioisotope.

Referring to FIG. 8, the daughter radioisotope (305) can be readily collected, for example with a collection fluid (311) which is introduced into the collection chamber (306) through a collection fluid inlet port. A collection fluid inlet valve (312) can be used to control the introduction of the collection fluid (311) into the collection chamber (306), and for example can be intermittently opened to introduce a series of pulses of the collection fluid (311) into the collection chamber (306).

Collection Chamber Holding Daughter Radioisotope

The collection chamber is configured to capture gaseous intermediate radioisotope, for example that has been transferred from a source chamber through an inter-chamber transfer valve described herein. The gaseous intermediate radioisotope is retained in the collection chamber for a period of time effective for it to spontaneously decay into a daughter radioisotope. The collection chamber comprises a collection surface (such as the inner walls of the collection chamber) for collecting emanated gaseous intermediate isotope and daughter radioisotope. The daughter radioisotope may deposit on the collection surface (e.g. inner wall) of the collection chamber, for example as small particles.

The collection chamber may be made from any suitable material capable of capturing and retaining daughter radioisotope. In some embodiments, the collection chamber is made from an inert metal or metal alloy (e.g. stainless steel or anodised titanium alloy), a non-fluorinated polymer (e.g. polyether ether ketone (PEEK)), glass (e.g. borosilicate glass) or a fluoropolymer (e.g. polytetrafluoroethylene, polyvinyledene fluoride). In one embodiment, the collection chamber is transparent.

The collection chamber comprises a collection fluid outlet port located at one end of the collection chamber, for example at the base of the chamber. In this embodiment, the collection fluid comprising daughter radioisotope pools at the base of the collection chamber and can be extracted from the collection chamber using gravity by opening the collection fluid outlet port, or using a pump to actively pull the fluid through the fluid outlet port.

The inner wall of the collection chamber comprises a surface, such as a collection surface described herein. In one embodiment, the inner wall of the collection chamber comprises a hydrophobic surface. Upon contact with the hydrophobic inner surface, the collection fluid forms a plurality of droplets having a high contact angle (i.e. >120°) on the hydrophobic inner wall surface. Because they form a high contact angle with the inner wall surface, the droplets of collection fluid roll readily down the inner wall surface due to gravity and in doing so the droplets collect daughter radioisotope (e.g. particles) which have deposited on the inner wall of the collection chamber.

The hydrophobic surface of the collection chamber may provide a contact angle (in) with the collection fluid of greater than 90, 95, 100, 105, 110, 115, 120, 125, 130, 135, 140, 145, 150, 155, 160, 165, 170, or 175. The hydrophobic surface of the collection chamber may provide a contact angle (in °) with the collection fluid of less than 175, 170, 165, 160, 155, 150, 145, 140, 135, 130, 125, 120, 115, 110, 105, 100, 95 or 90. The contact angle may be a range provided by any two of these upper and/or lower values.

In some embodiments, the surface of the inner wall of the collection chamber is configured to optimise the flow of the collection fluid to the collection fluid outlet port at the base of the collection chamber. For example, the surface of the inner wall of the collection chamber may be physically textured and/or chemically modified in a manner that facilitates the downward flow of the collection fluid towards a collection fluid outlet port. Such physical texturing may include inscribing an internal 3D profile within the collection chamber, for example a fluted or screw-like arrangement, which can facilitate the downward flow of the collection fluid.

Although the daughter radioisotope can be any decay product of a gaseous intermediate radioisotope described herein, in some embodiments, the daughter radioisotope is a lead radioisotope or a bismuth radioisotope, or a mixture thereof, for example lead-211 ($^{211}$Pb) and/or bismuth-211 ($^{211}$Bi), lead-212 ($^{212}$Pb) and/or bismuth-212 ($^{212}$Bi), or a mixture thereof and including daughter radioisotope thereof. In one embodiment, the daughter radioisotope is $^{212}$Pb or $^{211}$Pb, or a mixture thereof.

The daughter radioisotope can be used as a therapeutic radioisotope in radiolabelled drug applications. The daughter radioisotope can be extracted from the collection chamber in clinically relevant amounts. As such, it will be appreciated that the daughter radioisotope can be a product which can be extracted from the collection chamber, collected and used, as described herein.

In one embodiment, the daughter radioisotope is captured in the collection chamber by the processes described herein, including under the "Radioisotope generation and capture" aspect and embodiment of the present disclosure.

Collection Fluid

The process comprises introducing a collection fluid into the chamber (e.g. the collection chamber) through a collection fluid inlet port to collect the daughter radioisotope which has deposited on the collection surface, for example the inner wall of the collection chamber. The collection fluid comprises any suitable medium that can collect daughter radioisotope from the collection surface. In some embodiments, the collection fluid does not substantially react with the daughter radioisotope. It will be appreciated that the term "fluid" encompasses a fluid that is in a liquid or a gaseous state thereof, for example water or steam.

In one embodiment, the collection fluid is introduced into the collection chamber as a liquid or a condensable vapour.

The collection fluid may comprise an aqueous solution. The aqueous solution may be a biologically compatible aqueous solution. The aqueous solution may comprise water, physiological saline or other pH-neutral eluent solution, for example, that is compatible with proteins to which radioisotope is labelled (e.g. PSMA ligands). The use of such biologically compatible aqueous solutions may enable the daughter radioisotope be recovered and directly utilised in radiopharmacy applications, such as in radioligand therapy. Other suitable biologically compatible aqueous solutions include, for example, isotonic solutions, buffered solutions such as acetate buffers, carbonate/HEPES buffer solutions, urea solutions, and mixtures thereof.

According to at least some embodiments or examples described herein, using a biologically compatible aqueous solution to collect daughter radioisotope can eliminate the need for concentrated acidic solutions such as hydrochloric acid that in the prior art are required to recover captured daughter radioisotope from continuous transfer resin-based ion exchange generators. For example, daughter radioisotope extracted using acidic solutions is not amenable for direct use in radiopharmacy applications and must be brought to an appropriate pH level before being put into clinical or pre-clinical use.

In one embodiment, the aqueous solution may have a pH of between about 6 to about 10. The aqueous solution may have a pH of at least about 6, 6.5, 7, 7.5, 8, 8.5, 9, 9.5 or 10. The aqueous solution may have a pH of less than about 10, 9.5, 9, 8.5, 8, 7.5, 7, 6.5 or 6. The pH may be a range provided by any two of these upper and/or lower values.

In one embodiment, the collection fluid is water. The water can be introduced into the collection chamber as steam, condensable water vapour and/or liquid water.

Introduction of Collection Fluid to Collect Daughter Radioisotope

The collection fluid is introduced into the collection chamber through a collection fluid inlet port. In one embodiment, the collection fluid inlet port is connected to a collection fluid reservoir via a collection fluid inlet valve. The collection fluid reservoir houses the collection fluid for introduction into the collection chamber. The collection fluid reservoir may be made from any suitable material capable of housing the collection fluid, for example PTFE. The collection fluid reservoir, collection fluid inlet port and collection fluid inlet valve may collectively form a collection fluid delivery system.

The collection fluid may be introduced into the collection chamber through an aperture configured to spray the collection fluid (e.g. under pressure) into the collection chamber. Alternatively, the collection fluid may be introduced via a spray nozzle, such as an automated spray nozzle. It will be appreciated that the means of introducing the collection fluid into the collection chamber is not limited to any one particular aperture.

The introduction of the collection fluid into the collection chamber through the collection fluid inlet port may be controlled by a collection fluid inlet valve. The collection fluid inlet valve may be intermittently opened to introduce the collection fluid as a series of pulses into the collection chamber.

When the collection fluid inlet valve is in each open state, it may be open for a period of time of between about 10 milliseconds to about 300 milliseconds. The collection fluid inlet valve in each open state may be open for a period of time (in milliseconds) of at least about 10, 20, 30 40, 50, 60, 70, 80, 90, 100, 120, 140, 160, 180, 200, 240, 260, 280 or 300. The collection fluid inlet valve may be opened for a period of time (in milliseconds) of less than about 300, 280, 260, 240, 200, 180, 160, 140, 120, 100, 90, 80, 70, 60, 50, 40, 30, 20 or 10. The collection fluid inlet valve in each open state may be open for a period of time in a range provided by any two of these upper and/or lower ranges, for example between about 20 milliseconds to about 100 milliseconds or about 30 milliseconds to about 90 milliseconds.

The series of pulses provided by the intermittent opening of the collection fluid inlet valve may comprise any number of valve openings prior to extraction of the collection fluid through the collection fluid outlet port. For example, the collection fluid inlet valve is intermittently opened between 1 to 20 times prior to extraction of the collection fluid from the collection chamber. The collection fluid inlet valve may be intermittently opened at least 1, 2, 3, 4, 5, 6, 7, 8, 9, 10, 12, 14, 16, 18 or 20 times prior to extraction of the collection fluid from the collection chamber. The collection fluid inlet valve may be intermittently opened less than 20, 18, 16, 14, 12, 10, 9, 8, 7, 6, 5, 4, 3, 2 or 1 times prior to extraction of the collection fluid from the collection chamber. The number of times the collection fluid inlet valve may be opened can be a range provided by any two of these upper and/or lower values, for example between 1 to 10, 1 to 8 or 1 to 5 times prior to extraction of the collection fluid from the collection chamber.

The intermittent opening of the collection fluid inlet valve may occur at any suitable interval to generate the series of pulses (i.e. non-continuous flow) of the collection fluid. In one embodiment, the collection fluid inlet valve may be opened at an interval of between about 0.5 seconds to 60 seconds after the previous valve opening to provide the non-continuous transfer of collection fluid into the collection chamber. The collection fluid inlet valve may be intermittently opened at an interval (in seconds) of at least about 0.5, 1, 2, 5, 10, 15, 20, 25, 30, 35, 40, 45, 50, 55 or 60 after the previous valve opening to provide the non-continuous transfer of the collection fluid into the collection chamber. The collection fluid inlet valve may be intermittently opened at an interval (in seconds) of less than 60, 55, 50, 45, 40, 35, 30, 25, 20, 15, 10, 5, 2, 1 or 0.5 after the previous valve opening to provide the non-continuous transfer of the collection fluid into the collection chamber. A range may be provided by any two of these upper and/or lower values.

In one embodiment, the introduction of the collection fluid is driven by a pressure differential across the collection fluid inlet valve. The pressure differential across the collection fluid inlet valve may be created by a positive pressure in the collection fluid reservoir which drives the collection fluid through the collection fluid inlet valve. Alternatively or additionally, the pressure differential across the collection fluid inlet valve is created by a negative pressure in the collection chamber. The pressure differential across the collection fluid inlet valve may be created by a positive pressure in the collection fluid reservoir and a negative pressure in the collection chamber.

The positive pressure in the collection fluid reservoir may be created by heating the collection fluid reservoir to generate hot collection fluid having a vapour pressure effective to provide a positive pressure in the collection fluid reservoir. The collection fluid reservoir may be heated to a temperature effective to generate a desired pressure within the collection fluid reservoir. In one embodiment, the collection fluid reservoir is heated to a temperature of between about 100° C. to about 140° C.

The positive pressure in the collection fluid reservoir may be between about 15 kPa to about 400 kPa, or between about 15 kPa to about 250 kPa (gauge). The positive pressure in the collection fluid reservoir (in kPa) may be at least about 15, 20, 25, 30, 35, 40, 45, 50, 55, 60, 65, 70, 75, 80, 85, 90, 95, 100, 105, 110, 115, 120, 130, 140, 150, 160, 170, 180, 190, 200, 210, 220, 230, 240, 250, 300, 350 or 400. The positive pressure in the collection fluid reservoir (in kPa) may be less than about 400, 350, 300, 250, 240, 230, 220, 210, 200, 190, 180, 170, 160, 150, 140, 130, 120, 115, 110, 105, 100, 95, 90, 85, 80, 75, 70, 65, 60, 55, 50, 45, 40, 35, 30, 25, 20 or 15. The positive pressure in the collection fluid reservoir may be a range provided by any two of these upper and/or lower values, for example between about 60 kPa to about 200 kPa.

The negative pressure in the collection chamber may be generated by evacuating the collection chamber to a vacuum prior to the intermittent opening of the collection fluid inlet valve. The evacuation of the collection chamber to a vacuum may be provided by the vacuum pump (309) and vacuum valve (310) configured to apply a vacuum to and evacuate the collection chamber to create the pressure differential as described herein.

In one embodiment, the collection chamber is evacuated to a vacuum of between about 1 mbar to about 200 mbar prior to the opening of the collection fluid inlet valve. The collection chamber may be evacuated to a vacuum (in mbar) of at least about 1, 2, 5, 10, 20, 40, 50, 60, 80, 100, 150, 100, or 200, prior to the opening of the collection fluid inlet valve. The collection chamber may be evacuated to a vacuum (in mbar) of less than 200, 150, 100, 80, 60, 50, 40, 20, 10, 5, 2 or 1 prior to the opening of the collection fluid inlet valve. The vacuum may be a range provided by any two of these upper and/or lower amounts, for example between about 5 mbar to about 50 mbar.

The pressure differential across the collection fluid inlet valve may be between about 15 kPa to about 340 kPa. The pressure differential across the collection fluid inlet valve (in kPa) may be at least about 15, 20, 25, 30, 35, 40, 45, 50, 55, 60, 65, 70, 75, 80, 85, 90, 95, 100, 105, 110, 115, 120, 130, 140, 150, 160, 170, 180, 190, 200, 210, 220, 230, 240, 250, 260, 270, 280, 290, 300, 310, 320, 330 or 340. The pressure differential across the collection fluid inlet valve (in kPa) may be less than about 340, 330, 320, 310, 300, 290, 280, 270, 260, 250, 240, 230, 220, 210, 200, 190, 180, 170, 160, 150, 140, 130, 120, 115, 110, 105, 100, 95, 90, 85, 80, 75, 70, 65, 60, 55, 50, 45, 40, 35, 30, 25, 20 or 15. The pressure differential across the collection fluid inlet valve may be a range provided by any two of these upper and/or lower values, for example between about 50 kPa to about 240 kPa. It will be appreciated that the pressures in kPa can also be provided in bar (i.e. 1 kPa≈0.01 bar). Other pressure differentials are envisaged.

In one embodiment, the collection chamber is evacuated to vacuum followed by the introduction of the collection fluid through the collection fluid inlet port described herein. The collection fluid may be introduced into the collection chamber between 0.5 to 10 seconds after the collection chamber has been evacuated to vacuum.

In one embodiment, the introduction of the collection fluid into the collection chamber may comprise a (i) priming sequence and (ii) a wash sequence. Alternatively, the introduction of the collection fluid into the collection chamber may comprise a single wash sequence.

For step (i), the priming sequence comprises an initial opening of the collection fluid inlet valve to build up an amount of collection fluid (e.g. as a hot condensate) behind the collection fluid inlet valve (e.g. a fluid bolus). The priming sequence of the collection fluid inlet port may comprise intermittently opening the collection fluid inlet valve between 1 to 5 times. The collection fluid inlet valve may be opened for a period of time (in milliseconds) as described above.

For step (ii), the wash sequence comprises intermittently opening the collection fluid inlet valve to introduce collection fluid behind the collection fluid inlet valve and in the fluid collection reservoir into the collection chamber as a series of pulses.

The introduction of the collection fluid into the collection chamber occurs such that the fluid bolus carries significant momentum and effectively covers the entire surface of the inner wall of the collection chamber, after impact on the inner wall. The wash sequence may comprise intermittently opening the collection fluid inlet valve as described above, for example 1 to 20 times prior to extraction of the collection fluid from the collection chamber. The collection fluid inlet valve may be opened for a period of time (in milliseconds) as described above.

In one embodiment, the collection fluid is a condensable vapour. The condensable vapour can condense on the inner wall of the collection chamber (for example as a multitude of small liquid droplets) and collects the daughter radioisotope which has deposited on the inner wall of the collection chamber, for example by rolling down the inner chamber walls under gravity, during which they collect miniscule daughter radioisotope particles. In one embodiment, the collection chamber is cooled to a temperature effective to condense the condensable vapour on the inner wall of the collection chamber, for example as a multitude of small liquid droplets.

In one embodiment, the collection fluid is a liquid and a pressurised carrier gas is introduced together with the collection fluid through the collection fluid inlet port to form an aerosol comprising a plurality of liquid droplets (that roll readily down the inner wall surface due to gravity and collect the daughter radioisotope which have deposited on the inner wall of the collection chamber).

According to at least some embodiments or examples described herein, the extraction of daughter radioisotope described herein can minimise the total volume of collection fluid required to effectively extract daughter radioisotope from the collection chamber, and thus provide a daughter radioisotope solution having a high specific activity (i.e. radioisotope concentration).

In another embodiment, the collection fluid is a liquid that is sprayed into the collection chamber through an aperture, for example a small orifice.

The amount of collection fluid introduced into the collection chamber may vary depending on the number of collection fluid inlet valve openings that have been used to introduce the collection fluid into the collection chamber (e.g. the number of valve openings in the wash sequence). Other factors that may influence the amount of collection fluid required including the pressure driving the collection fluid into the collection chamber. In one embodiment, between about 0.1 mL to about 10 mL, about 0.1 mL to about 5 mL or about 1 mL to about 3 mL of collection fluid is introduced into the collection chamber prior to extraction.

Extraction of Collection Fluid and Daughter Radioisotope

The process for recovering daughter radioisotope described herein comprises extracting the collection fluid comprising the daughter radioisotope from the collection chamber through a collection fluid outlet port to recover the daughter radioisotope. In one embodiment, the extraction of the collection fluid through the collection fluid outlet port is controlled by a collection fluid outlet valve which is intermittently opened to extract the collection fluid comprising the daughter radioisotope from the collection chamber. The collection fluid outlet valve may be an electronically controlled solenoid valve.

In one embodiment, the collection fluid comprising collected daughter radioisotope accumulates at the lower region/base of the collection chamber above the collection fluid outlet port. In this example, opening the collection fluid outlet valve can extract the collection fluid via gravity. Alternatively, the collection fluid may be extracted through the collection fluid outlet port using a pump, for example a peristaltic fluid pump.

The collection fluid outlet valve and/or pump may be opened periodically to recover the collection fluid and daughter radioisotope for intended therapeutic applications. For example, the collection fluid comprising daughter radioisotope may be extracted into a vessel suitable for transport to a radiochemical laboratory or radiopharmacy. For example, the collection fluid outlet port may be configured to transfer the extracted collection fluid to various collection systems, such as fraction collectors, glass vials etc. The collection fluid outlet valve and/or pump can be controlled to extract a predetermined volume of collection fluid and daughter radioisotope, for example depending on the desired activity of $^{212}$Pb for downstream medical applications.

Applications

The applications of the present technology include various applications in the medical, therapeutic and diagnostic fields, including for example, as radiopharmaceutical agents for treating cancer. For example, the nuclear medicine field provides for the radiolabelling of macromolecules such as antibodies that bind with high specificity to antigens expressed on particular cancer cells. Alpha-particle emitters (including daughter radioisotope generated, captured and collected as described herein) are particularly effective as short range cytotoxic payloads on such targeted molecular vehicles, thereby allowing for cancer cell destruction with minimal impact on surrounding healthy tissue.

In some embodiments, the daughter radioisotope (e.g. $^{212}$Pb) produced using the generator and process described herein are well suited for being attached to cancer targeting molecules since it is of high radiochemical purity and of high specific activity (for example owing to the low $^{208}$Pb content as a result of using the generator and process described herein). The generation of high purity daughter radioisotope (e.g. high purity $^{212}$Pb) s using the generator and process described herein will allow for the production of this therapeutic isotope at scale with wide geographic distribution.

The daughter radioisotope, for example $^{212}$Pb generated using the processes and generators described herein can be directly utilised in various clinical applications, including conjugation to targeting molecules/ligands for use in radiopharmacy applications, such as radioligand therapy. Examples of targeting molecules/ligands include antibodies and/or peptides, for example prostate-specific membrane antigen (PSMA) ligands.

The present application claims priority from AU2021902649 filed on 23 Aug. 2021, the entire contents of which are incorporated herein by reference.

EXAMPLES

In order that the disclosure may be more clearly understood, particular embodiments of the invention are described in further detail below by reference to the following non-limiting experimental materials, methodologies and examples.

Example 1: Loading Parent Radioisotope on or within an Inert Ceramic Substrate

Preparation of Inert Ceramic Substrate Surface by Thermal Oxidation

Inert ceramic substrates composed of tantalum pentoxide ($Ta_2O_5$) coated on tantalum metal were prepared by heating disks of tantalum metal (30 mm diameter, 6 mm thick) in a muffle furnace using a temperature program as follows: room temperature to 575° C. over 100 minutes, holding at 575° C. for 45 minutes, then allowing slow natural cooling. Before being heated, the tantalum metal disks were abraded uniformly with 240 grit sandpaper ($Al_2O_3$ abrasive) to remove machining marks, then rinsed with de-ionised water and dried using compressed nitrogen.

Inert ceramic substrates composed of zirconium dioxide ($ZrO_2$) coated on zirconium metal were prepared by heating disks of zirconium metal (30 mm diameter, 6 mm thick) in a muffle furnace using a temperature program as follows: room temperature to 750° C. over 120 minutes, holding at 750° C. for 300 minutes, then allowing slow natural cooling. Before being heated, the zirconium metal disks were abraded uniformly with 240 grit sandpaper ($Al_2O_3$ abrasive) to remove machining marks, then rinsed with de-ionised water and dried using compressed nitrogen.

Preparation of Inert Ceramic Substrate Surface by Anodic Polarisation

Tantalum metal disks were abraded uniformly with 240 grit sandpaper ($Al_2O_3$ abrasive) to remove machining marks, then rinsed with de-ionised water and dried using compressed nitrogen. The abraded tantalum metal disk was then affixed into an anodisation cell such that its abraded surface was horizontal and covered with an electrolyte solution of 0.05M citric acid in deionised water, with its rear surface electrically connected to a copper wire. A platinum counter electrode was placed into the citric acid solution above (but not touching) the tantalum disk. The two electrodes were connected to a DC power supply with the tantalum electrode as anode (having positive polarity) and the platinum electrode as cathode (having negative polarity). A constant current of 30 milliamperes was applied across the two-electrode cell for 15 minutes and the power supply then switched into constant voltage mode at 10 volts for 30 minutes, after which the voltage was increased to 20 V for a further 30 minutes, and then to 30 V for a further 30 minutes. The anodised disk comprising the $Ta_2O_5$ surface on tantalum (i.e. a tantalum/$Ta_2O_5$ disk) was then removed from the solution and washed with deionised water and air-dried.

Preparation of Aqueous Solutions Comprising Parent Radioisotope

To prepare the aqueous solution comprising the parent radioisotope for loading an immobilising on or within the inert ceramic substrate, solutions of $^{232}Th^{4+}$ with a concentration in the range 0.5 to 100 millimoles per litre (mM) were made up in aqueous nitric acid by adding appropriate amounts (0.5-15 mL) of $HNO_3$ with a concentration in the range 0.001 to 5 moles per litre (M), to 2 to 150 mg of solid thorium nitrate pentahydrate [$^{232}Th(NO_3)_{4.5}H_2O$].

In another example, solutions of $^{228}Th^{4+}$ in nitric acid (200-600 μL) were prepared by adding aqueous nitric acid with a concentration in the range 0.001 to 5 moles per litre (M) to 2 to 25 mg of solid thorium nitrate pentahydrate [$^{228}Th(NO_3)_4 \cdot 5H_2O$].

Depositing the Aqueous Radioisotope Solution onto the Inert Ceramic Substrate Surface Thorium nitrate solutions were applied to freshly prepared substrate surfaces by micropipetting the liquid (typically 50-500 μL) dropwise onto each $Ta_2O_5$ or $ZrO_2$ disk surface. The deposited $Th^{4+}$ solution was left undisturbed on the oxide substrate for a period of time (e.g. 45 minutes) at room temperature. The wettability of the $Ta_2O_5$ and $ZrO_2$ surfaces was such that minimal or no agitation was needed to ensure complete liquid coverage of the substrate surface. Alternatively, the $Ta_2O_5$ or $ZrO_2$ disk substrates can be submerged in the thorium solution described above, for example in a microwave reactor, which can then heated as described below.

Optional Addition of Aqueous Precipitant Solutions to the Parent Radioisotope Solution In some cases, after the designated period of contact between the $Ta_2O_5$ or $ZrO_2$ surface and the $Th^{4+}$ solution, a precipitant was added to the deposited aqueous solution on the surface of the substrate disk. In one instance, 40 μL of a 15 mM aqueous oxalic acid [$(COOH)_2$] solution was added to the thorium solution on the $Ta_2O_5$ surface. The solution was left for a suitable period of time (e.g. five minutes) after which the liquid on the disk surface was evaporated by placing the disk on a hot plate (e.g. at 85° C., 15 minutes). In other instances, 50 μL of a 5 mM aqueous ammonium fluoride (NFU) solution was added to the thorium solution on a $ZrO_2$ surface or on to a $Ta_2O_5$ substrate. The solution was left for a suitable period of time (e.g. five minutes) after which the liquid on the disk surface was evaporated by placing the disk on a hot plate (e.g. 85° C., 15 minutes).

Heating the Inert Ceramic Substrate to Aqueous Radioisotope Solution

The tantalum/$Ta_2O_5$ and zirconium/$ZrO_2$ disk substrates loaded with thorium were placed on a flat refractory tray in a muffle furnace to convert residual thorium nitrate and thorium (and if present other thorium-precipitant salts) to thorium dioxide ($ThO_2$). The furnace was taken from ambient temperature to 325° C. over a 150 minute period and it was then held at 325° C. for 150 minutes before being allowed to cool naturally. Alternatively, where the $Ta_2O_5$ or $ZrO_2$ disk substrates have been placed in a microwave reactor and submerged in the thorium solution described above, the substrates can then heated under suitable overpressure to a suitable temperature (e.g. between about 100° C. to about 300° C.) over a period of time (e.g. between about between 2 h to about 24 h), before being removed from the solution, cooled and washed.

Example 2: Characterisation of Inert Ceramic Substrates Comprising Immobilised Parent Radioisotope Evidence of finely dispersed thorium oxide was detected on the surfaces of both treated $Ta_2O_5$ substrate surfaces and treated $ZrO_2$ substrate surfaces, using energy dispersive X-ray spectroscopy with a scanning electron microscope.

Figure 3A:
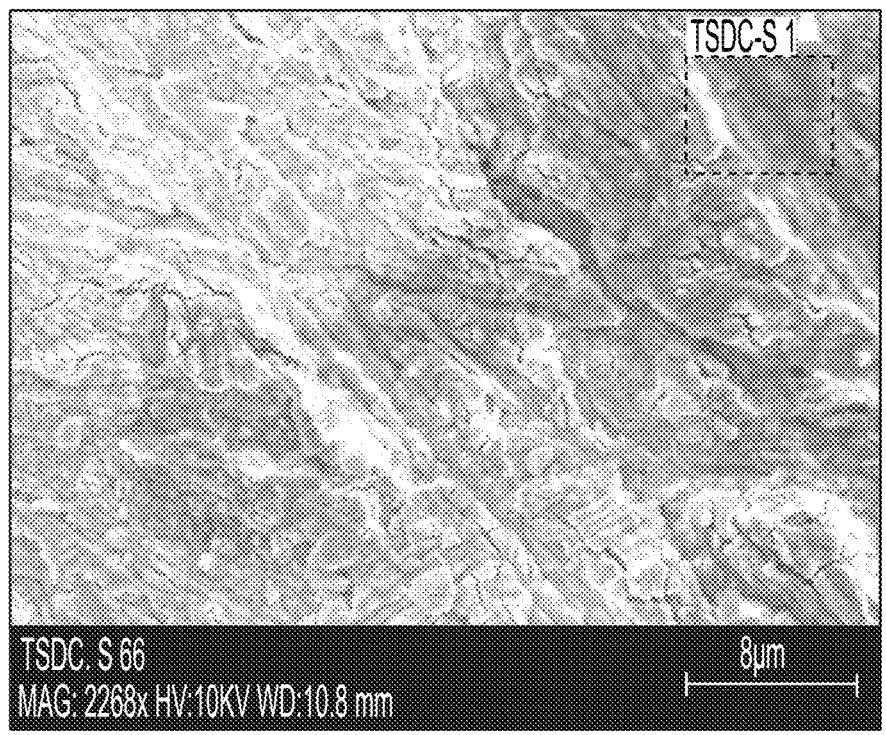
FIG. 3A shows a SEM image of a $Ta_2O_5$ substrate comprising immobilised thorium radioisotope on the surface prepared by the process described herein.
Figure 3B:
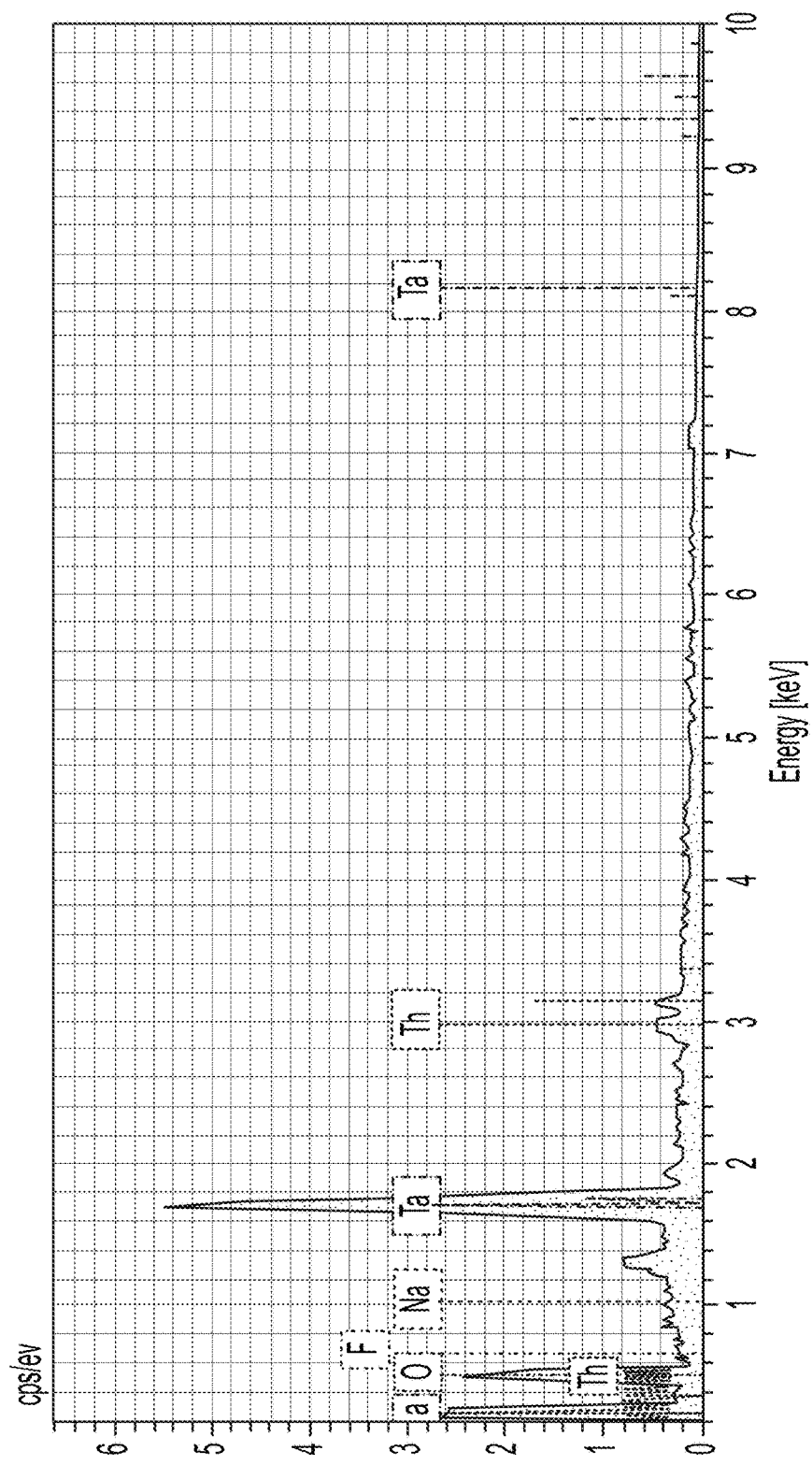
FIG. 3B shows a EDX spectrum of the surface of the substrate obtained from the boxed area. Evidence of finely dispersed thorium oxide was detected on the surface of the $Ta_2O_5$ substrate.

FIG. 3A is a magnified image of a $Ta_2O_5$ substrate showing the typical texture for such abraded oxide surfaces prepared by the heat-treatment described herein. The image also shows the patch-wise nature of thorium deposition when ammonium fluoride ($NH_4F$) is used as a precipitant-seen as darker regions under secondary electron detection—with such patches presumably comprising an oxy-fluoride phase. The EDX spectrum depicted in FIG. 3B shows a clear thorium x-ray signal from the darker region and, significantly, this is not associated with any particle-like feature or phase larger than the ~0.8 μm spatial resolution of the image, or with any feature that could have tenuous connectivity with the oxide surface.

Figure 4A:
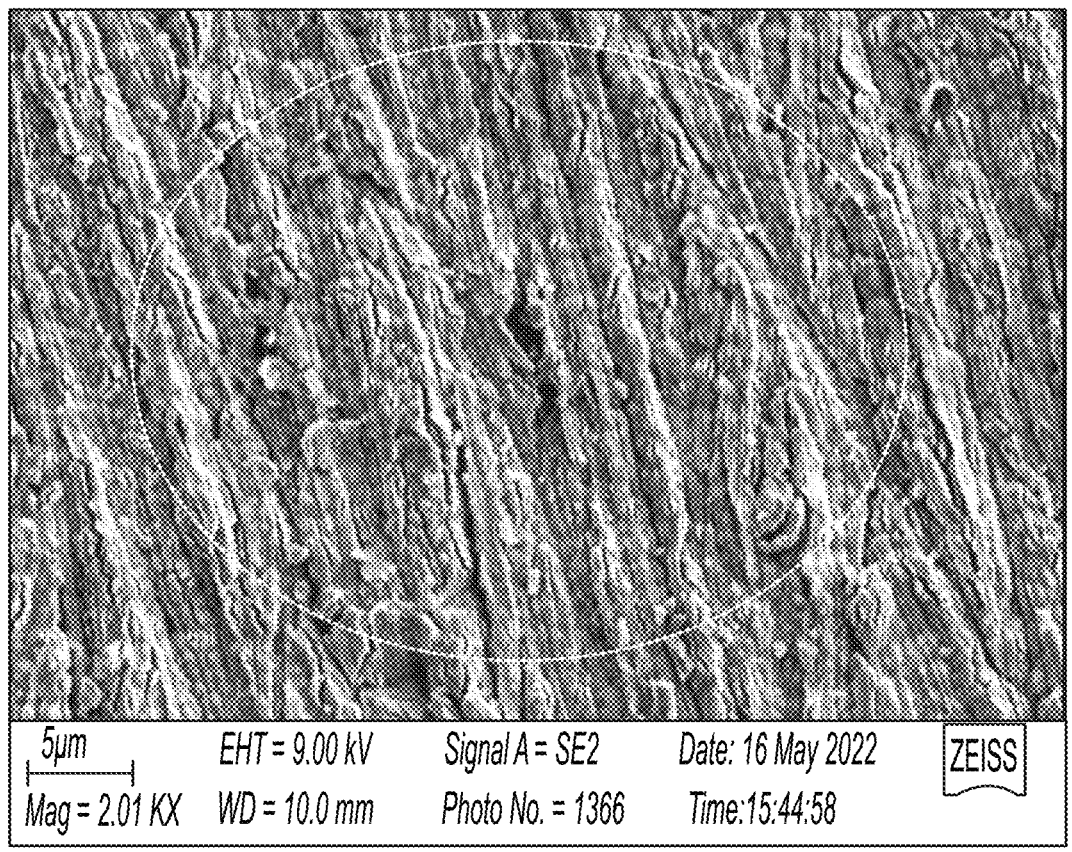
FIG. 4A shows a SEM image of a $Ta_2O_5$ substrate comprising immobilised thorium radioisotope on the surface prepared by the process described herein.
Figure 4B:
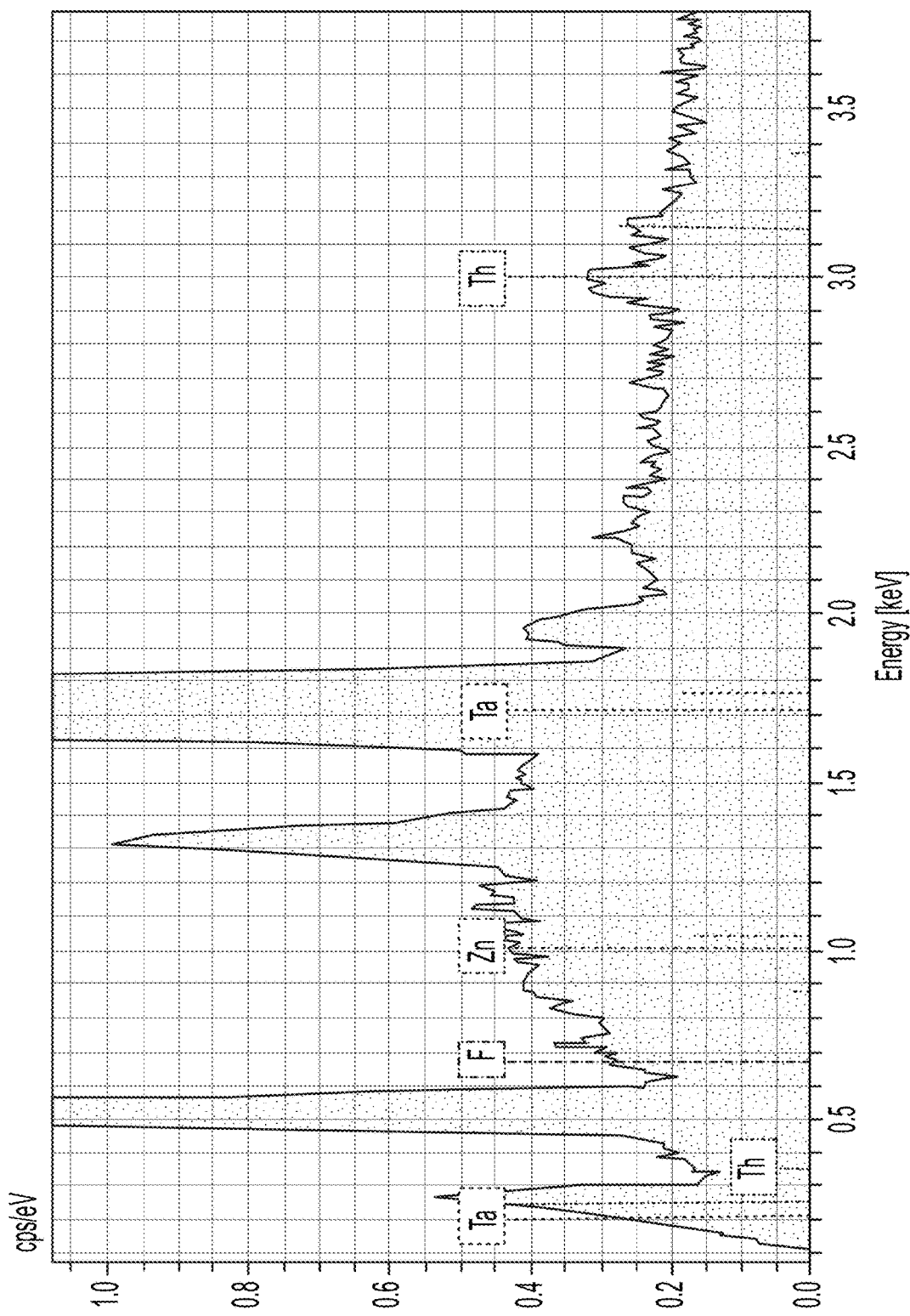
FIG. 4B shows EDX spectrum of the surface of the substrate obtained from the circular area. Evidence of finely dispersed thorium oxide was detected on the surface of the $Ta_2O_5$ substrate.

FIG. 4A is a magnified image of a $Ta_2O_5$ substrate on which NMI' was used as a precipitant during the thorium deposition process. In FIG. 4A, the area sampled for EDX analysis is shown together with the resultant x-ray spectrum in FIG. 4B. A clear thorium x-ray signal is evident, yet is not associated with any particle-like feature or phase larger than the 0.4 μm spatial resolution of the image, or with any feature that could have a tenuous connectivity with the oxide surface.

Figure 5A:
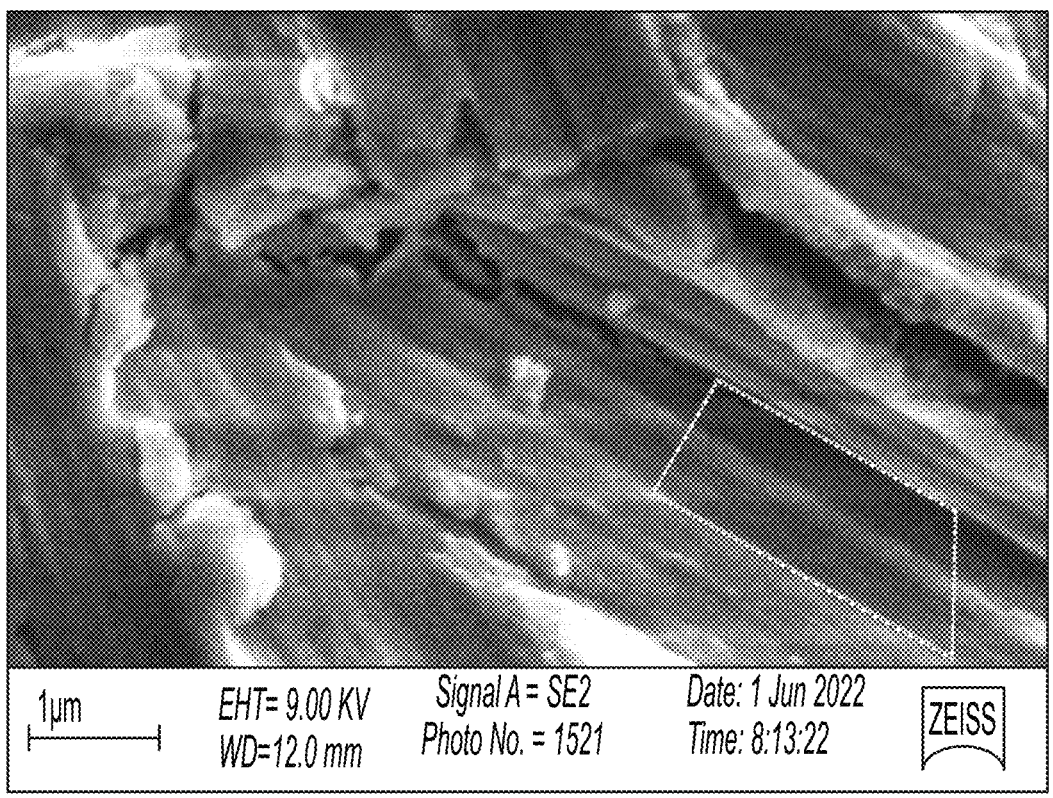
FIG. 5A shows a SEM image of a $ZrO_2$ substrate comprising immobilised thorium radioisotope on the surface prepared by the process described herein.
Figure 5B:
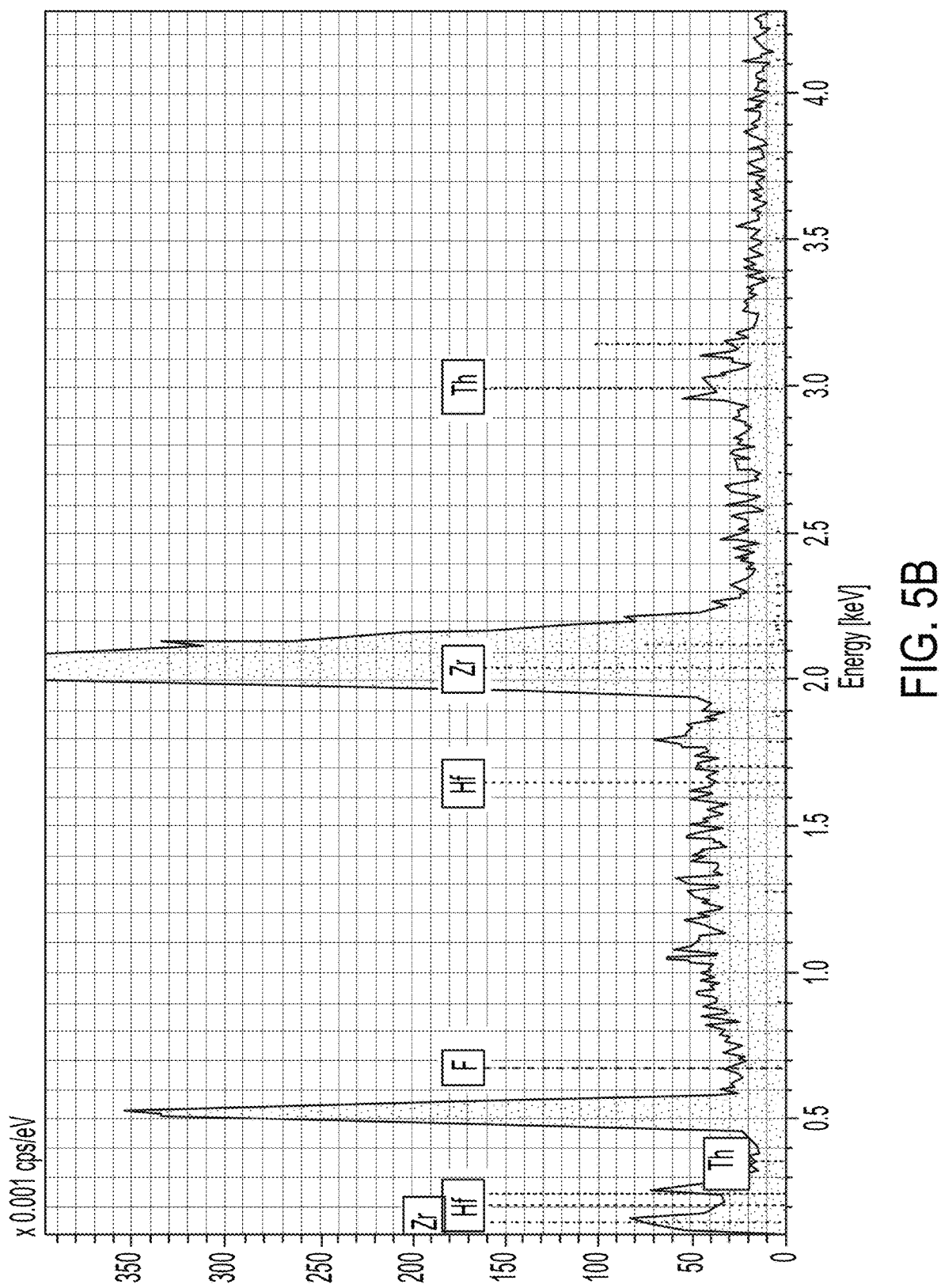
FIG. 5B shows EDX spectrum of the surface of the substrate obtained from the boxed area. Evidence of finely dispersed thorium oxide was detected on the surface of the $ZrO_2$ substrate.

FIG. 5A is an image of a $ZrO_2$ substrate showing the abraded oxide surface at quite high magnification together with the area sampled for EDX analysis and the resultant spectrum which is shown in FIG. 5B. A clear thorium signal is evident, yet is not associated with any particle-like feature or phase larger than the ~ 0.08 μm spatial resolution of the image, or with any feature that could have a tenuous connectivity with the oxide surface.

Figure 6A:
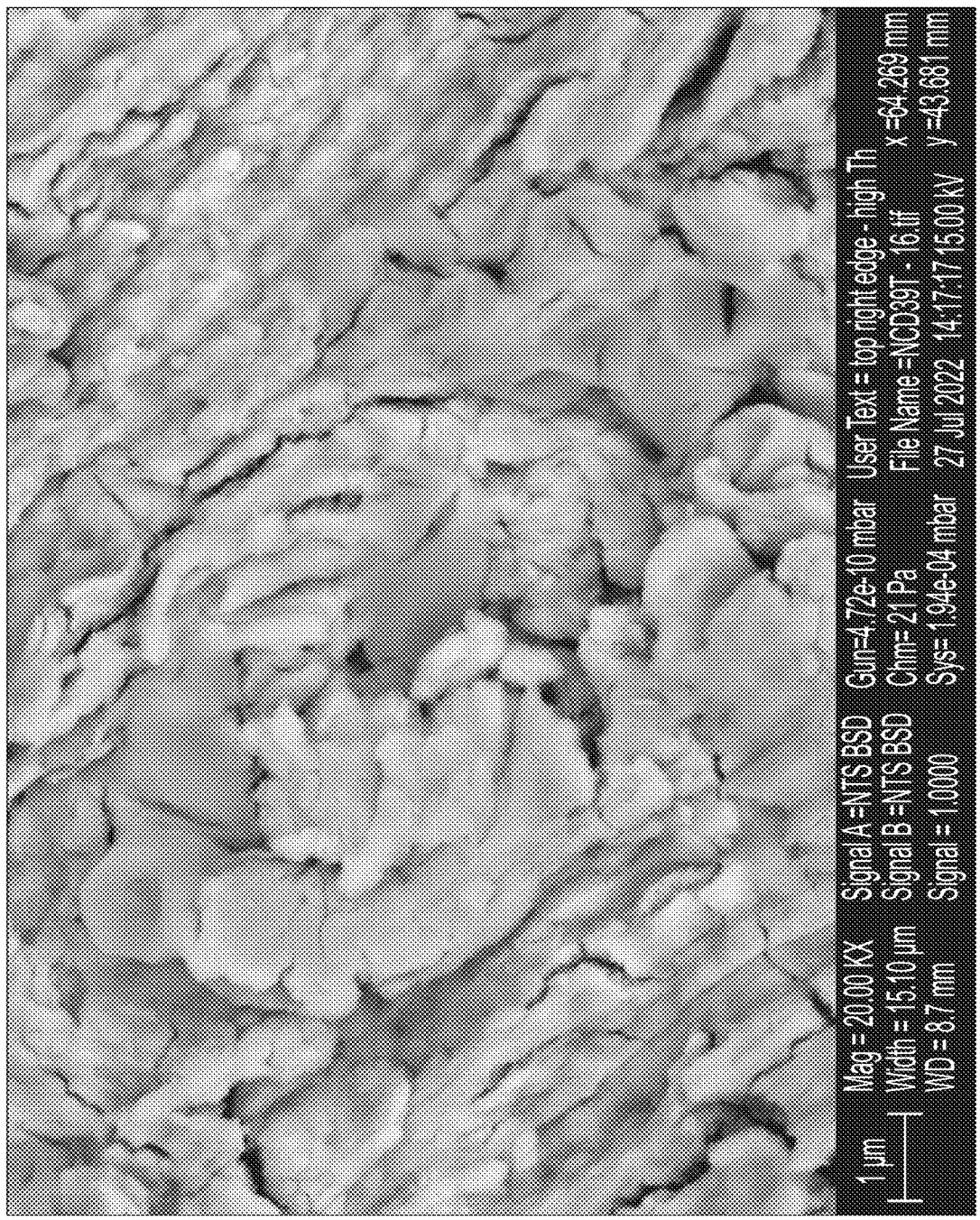
FIG. 6A shows a SEM image of a $Ta_2O_5$ substrate comprising immobilised thorium radioisotope on the surface prepared by the process described herein.
Figure 6B:
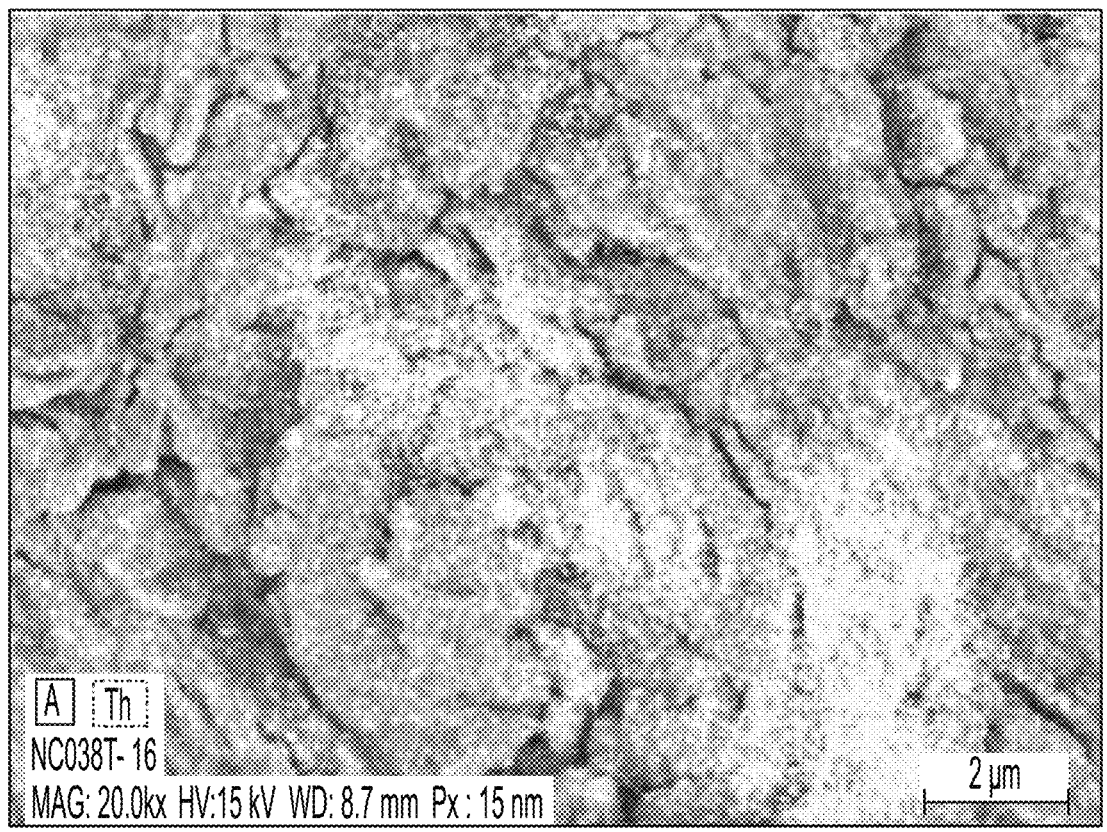
FIG. 6B shows a SEM image of a $Ta_2O_5$ substrate comprising immobilized thorium radioisotope on the surface prepared by the process described herein, with evidence of finely dispersed thorium oxide detected on the surface of the $Ta_2O_5$ substrate.
Figure 6C:
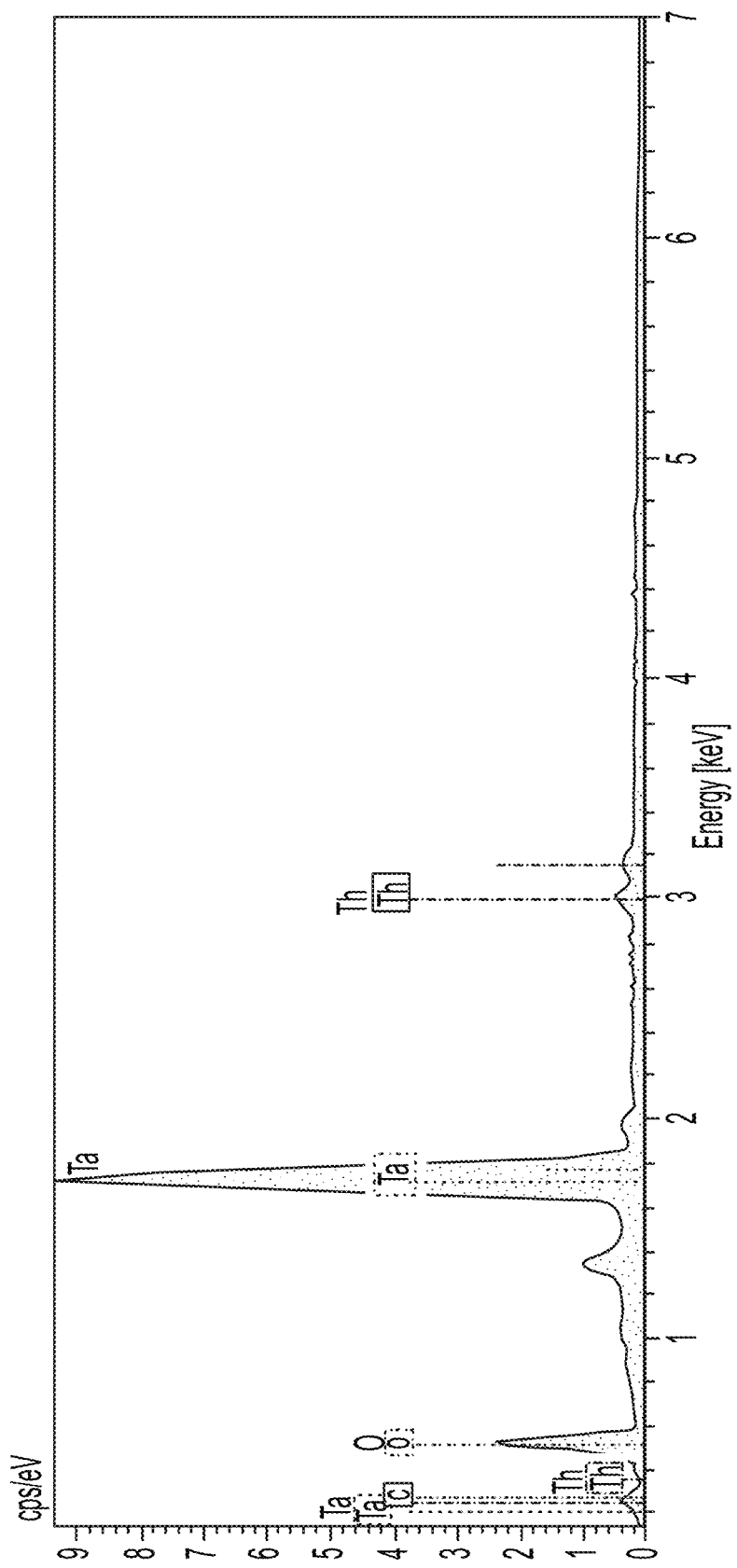
FIG. 6C shows EDX spectrum and spatial map of thorium distribution. Evidence of finely dispersed thorium oxide was detected on the surface of the $Ta_2O_5$ substrate.

FIG. 6A is a magnified image of a $Ta_2O_5$ substrate on which oxalic acid ($C_2O_4H_2$) was used as a precipitant during the thorium deposition process. FIG. 6B shows a SEM image of a $Ta_2O_5$ substrate comprising immobilized thorium radioisotope on the surface prepared by the process described herein, with evidence of finely dispersed thorium oxide detected on the surface of the $Ta_2O_5$ substrate. For this sample the entire image area was sampled for EDX analysis as shown in FIG. 6C and a spatial map for the thorium signal was also produced. A clear thorium signal is evident from these, from which it is apparent that deposited thorium is associated with a distinct solid on the substrate surface, with a different morphology, comprising sub-micron irregular-shaped crystallites that appear well bound to the substrate surface.

Example 3: Generation of $^{212}Pb$ Using the Inert Ceramic Substrates

Figure 15:
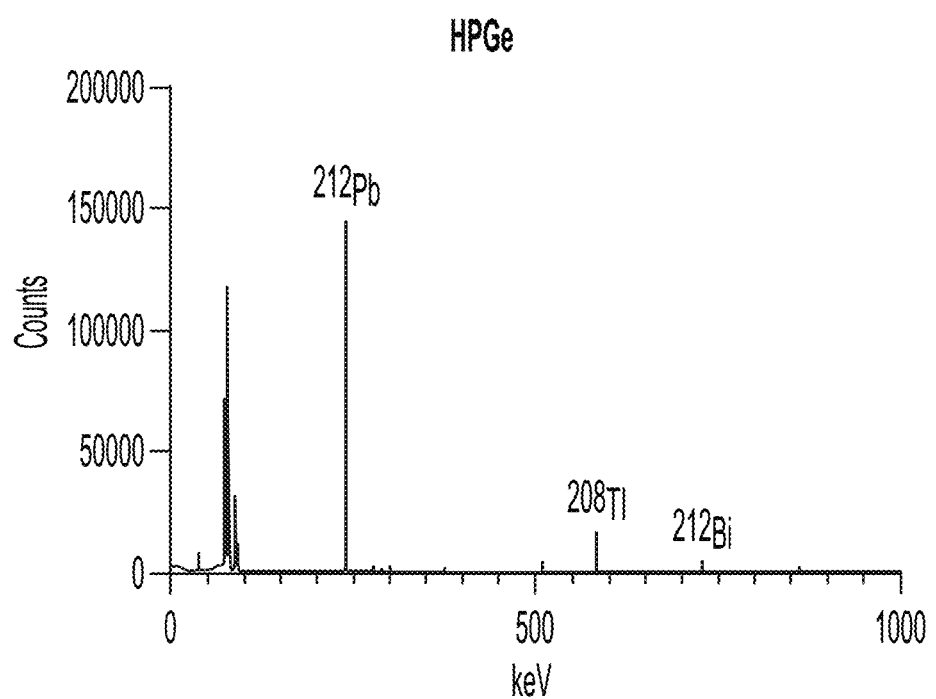
FIG. 15 shows gamma spectrum of $^{212}$Pb captured using a generator housing a tantalum oxide ($Ta_2O_5$) substrate comprising immobilised thorium-228 ($^{228}$Th) radioisotope described herein.

A tantalum oxide substrate comprising immobilised $^{228}Th$ prepared according to Example 1 was housed within a radioisotope generator comprising a tungsten shroud (50 mm thick, for gamma shielding purposes) holding the inert ceramic substrate in an inverted configuration above the bench surface. A PTFE collection surface was placed directly under the inert ceramic substrate such that the thoriated surface of the substrate was in line-of-sight configuration with the collection surface, and left for defined periods, (e.g. 1 hour, 4 hours, 12 hours) to collect $^{212}Pb$ radioisotope. The collected $^{212}Pb$ radioisotope was subsequently washed off the PTFE surface with dilute HCl and placed in a wash fluid vial. The wash fluid vial comprising the collected $^{212}Pb$ radioisotope was then placed in an ionisation chamber instrument to measure the activity of collected $^{212}Pb$ radioisotope. Chemical and radiometric assays on $^{212}Pb$ radioisotope produced using a thoriated inert ceramic substrate of Example 1 in the "line-of-sight" generator showed very low levels of contamination by parent isotope (thorium and radium), as shown in FIG. 15.

Example 4: Simulation of Transfer of Gaseous Intermediate from Source Chamber to Collection Chamber To determine the optimal timing between each transfer of gaseous intermediate radioisotope, a series of simulations were constructed using numerical solutions to the coupled differential Bateman equations describing the $^{228}Th$ decay series (see FIG. 7) to calculate the activity of each isotope in the series at any point in time under a particular set of conditions.

Two systems were modelled in parallel: a) one covered the source chamber in which $^{228}Th$ was in secular equilibrium with its full decay chain; and b) the other covered the collection chamber in which $^{220}Rn$ decayed into its progeny. Following the establishment of secular equilibrium in the source chamber (i.e., after a constant $^{224}Ra$ population was present) all $^{220}Rn$ present in the source chamber was periodically removed and transferred into the collection chamber where it immediately began to decay into its various daughters. This process was simulated 10-1500 times at 60 different time intervals of $^{220}Rn$ transfer. The computed activities of isotopes in the decay series in each of the source chamber and collection chamber are shown in FIGS. 10 and 11.

Figure 12:
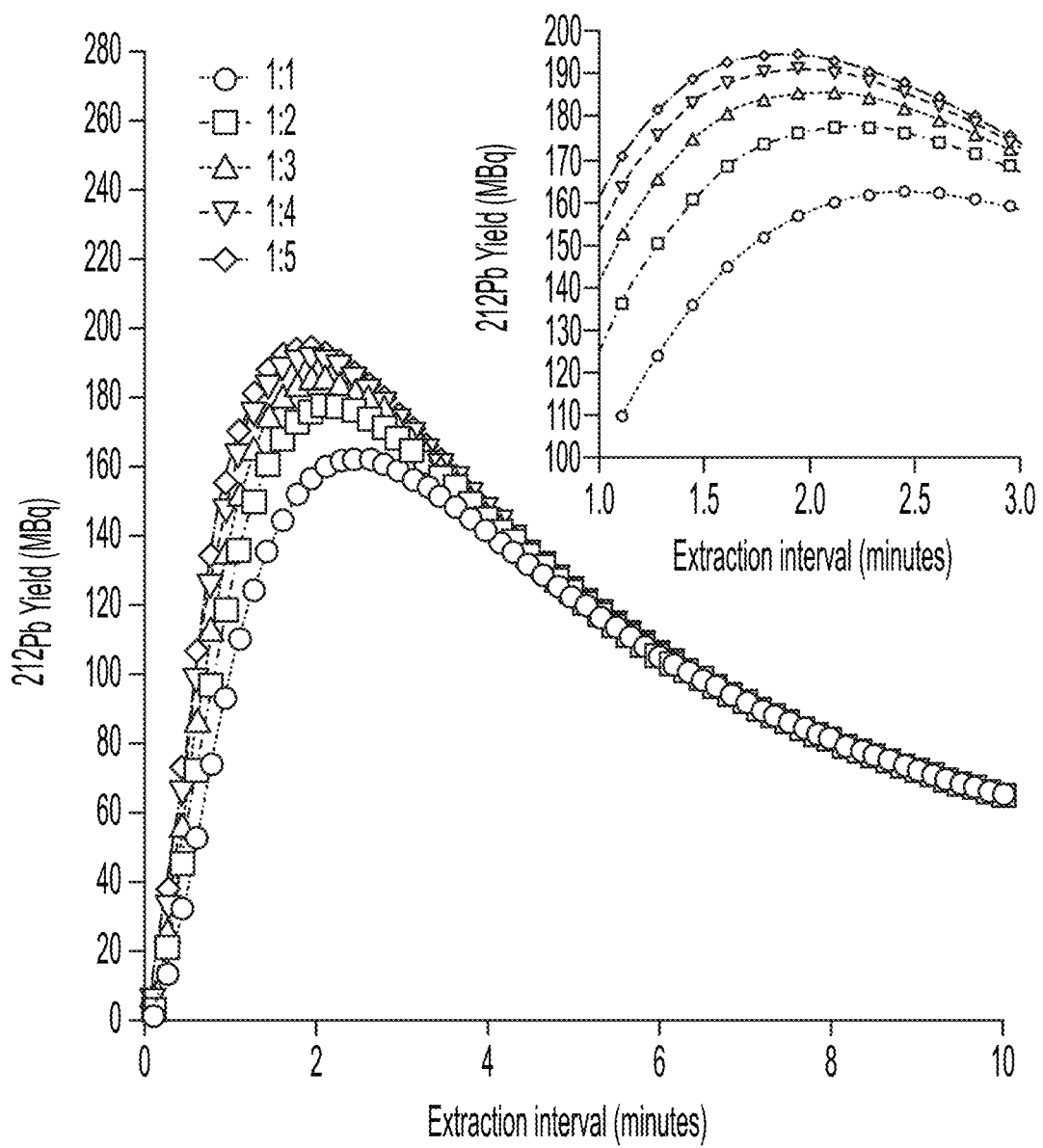
FIG. 12 shows a plot of the simulated total yield of lead-212 ($^{212}$Pb)
Figure 13:
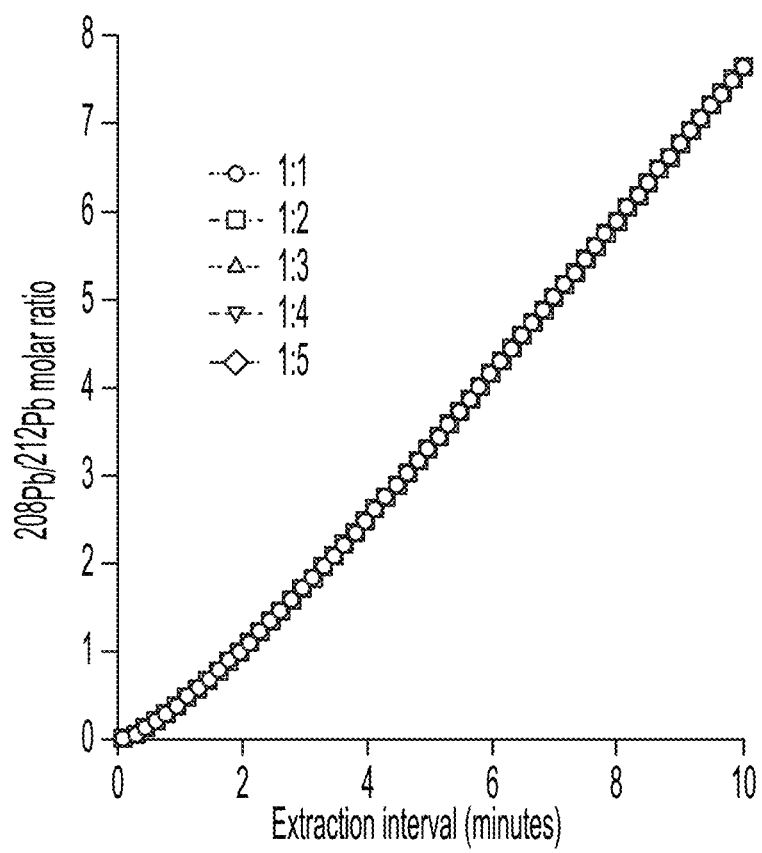
FIG. 13 shows a plot of the simulated molar ratio of lead-208/lead-212 ($^{208}$Pb/$^{212}$Pb) in the collection chamber based on the time intervals between successive transfers of gaseous radon-220 ($^{220}$Rn) from the source chamber to the collection chamber. The different lines denote different configurations for driving the gaseous radon-220 ($^{220}$Rn) between the source chamber and the collection chamber.
Figure 14A:
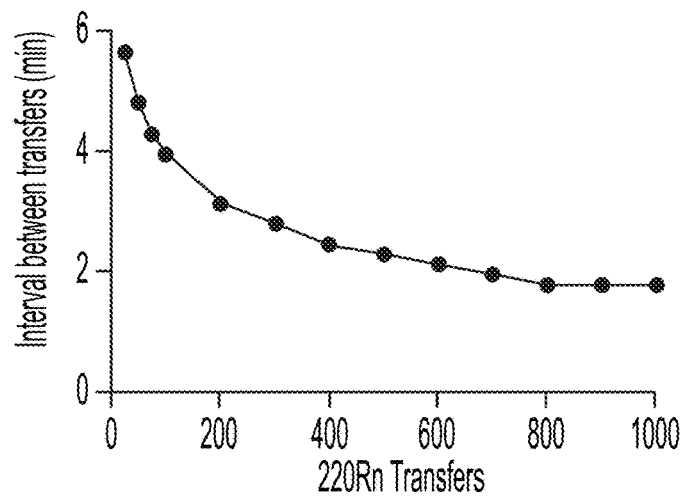
FIG. 14A shows a simulation plot of the relationship between the number of gas transfer events of radon-220 ($^{220}$Rn) (operating at a 5:1 ratio of pressure driven gas transfer event:vacuum driven gas transfer event) and interval between transfer events.
Figure 14B:
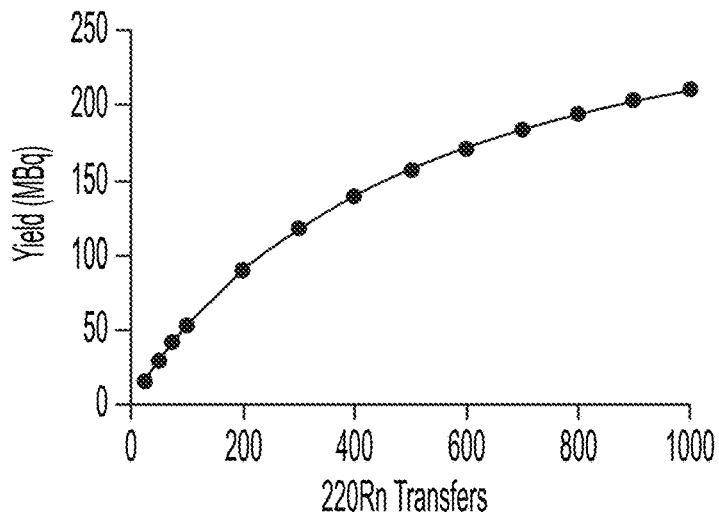
FIG. 14B shows a simulation plot of the relationship between the number of gas transfer events of radon-220 ($^{220}$Rn) (operating at a 5:1 ratio of pressure driven gas transfer event:vacuum driven gas transfer event) and total yield (MBq) of lead-212 ($^{212}$Pb) in the collection chamber.
Figure 14C:
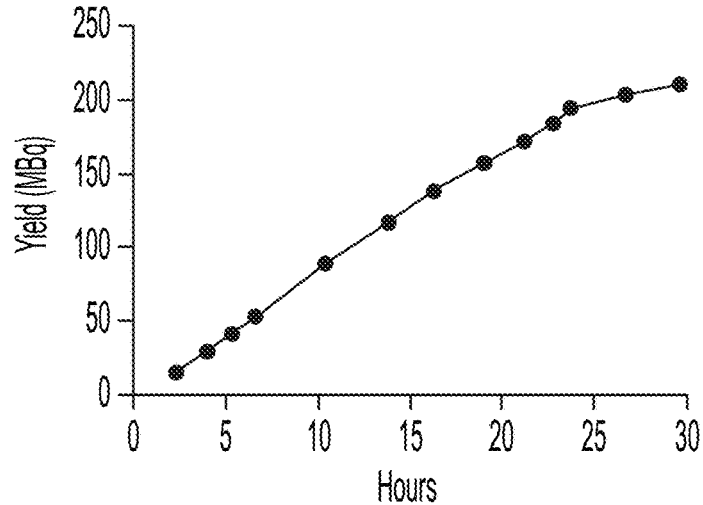
FIG. 14C shows a simulation plot showing the relationship between the total time of generator operation and the total yield (in MBq) of lead-212 in the collection chamber, based on optimal gaseous radon-220 ($^{220}$Rn) transfer intervals.

The computed $^{212}Pb$ activity in the collection chamber was plotted as a function of the time interval between successive $^{220}Rn$ transfer events to determine the optimal transfer time and optimal transfer event configuration (i.e. number of pressure driven gas transfer events vs vacuum driven gas transfer events). In each simulation, a pressure driven gas transfer event assumed no loss of $^{220}Rn$ in the collection chamber following the start of the next transfer event. For a vacuum driven gas transfer event, it was assumed that all $^{220}Rn$ present in the collection chamber at the time of initiation of the vacuum driven gas transfer event is lost from the system. $^{212}Pb$ yields as a function of transfer time are shown in FIG. 11. In addition, the simulations demonstrated that shorter transfer intervals generated $^{212}Pb$ with a lower content of $^{208}Pb$ (FIG. 12).

Example 5: Generation of Radioisotope

One embodiment of the generator utilised to generate and capture radioisotope is provided, and is illustrated in FIG. 8.

The inert ceramic substrate comprising immobilised $^{228}Th$ of Example 1 can be used as a parent radioisotope to generate and capture a population of $^{212}Pb$. The inert ceramic substrate can be sealed within the source chamber where the $^{228}Th$ spontaneously decays (via 22+R a) into $^{220}Rn$ which emanates and separates away from the inert ceramic substrate.

The emanated $^{220}Rn$ can be transferred from the source chamber to the collection chamber through the inter-chamber transfer valve which is intermittently opened at well-defined time intervals. The intervals can be selected based on several factors including the activity of the $^{220}$Rn in the source chamber. In this example, to achieve optimal yields of $^{212}$Pb, the generator can be operated by transferring the emanated $^{220}$Rn by a vacuum driven gas transfer event followed by a series of pressure driven gas transfer events at defined time intervals.

The timing of the sequence of opening and closing of the inter-chamber transfer valve and vacuum valve can be modified to optimise $^{212}$Pb yield. For example, sufficient time must be allowed for the $^{220}$Rn to grow in the source chamber between each pressure driven transfer event. Similarly, sufficient time must be allowed for the collected $^{220}$Rn to decay in the collection chamber before application of vacuum to the collection chamber when generating the vacuum driven gas transfer event.

To achieve optimal yields of $^{212}$Pb the transfer of $^{220}$Rn from the source chamber to the collection chamber utilises the intermittent opening of the inter-chamber transfer valve comprising a series (e.g. two or more) of pressure driven gas transfer events at defined time intervals followed by a vacuum driven gas transfer event to re-equilibrate pressures within the generator, for example at a ratio of 5:1.

Example 6: Extraction of Lead Radioisotope

The recovery of accumulated $^{212}$Pb (or $^{211}$Pb) product isotope from the collection chamber in a small volume (<5 mL) of metal-free water can be demonstrated by the following examples:

Preparation of the Wash Fluid Reservoir.

90 cm$^3$ of deionised water was added to a PTFE water reservoir, by syringe, through ¼" (BSP) threaded port in the PTFE lid. A 120° C. temperature-rated polymer T-piece was then screwed into the port using PTFE tape on the male threads to assure a tight seal. The top of T-piece supported an analogue pressure gauge fitted via a PTFE diaphragm seal (Stubbe). The side-arm of the T-piece was connected to a short segment of silicone tubing (8 mm OD I 6 mm ID) about 70 mm long. At its other end, this tubing segment was coupled with a wash fluid solenoid valve using a polymer push-in fitting. The solenoid valve was a type (Gemii-52) having all wetted parts made of fluoropolymer (PVDF body/PTFE seals).

Preparation of a Simulated Collection Chamber and Connecting this to the Wash Fluid Reservoir Via a Solenoid Valve.

A simulated radon-collection chamber made from borosilicate glass was custom built with very similar internal dimensions to collection chambers made from (opaque) fluoropolymer, such that it became possible to visualise the washing of internal chamber walls. The glass chamber was connected to the Gemii-52 solenoid valve with a short segment of silicone tubing (4 mm OD|2.5 mm ID) about 70 mm long. The glass chamber was also connected to a vacuum line via a second solenoid valve using polyurethane tubing (4 mm OD|2.5 mm ID) and a custom-built digital pressure gauge was built into this line. In some instances, a small amount of water-soluble dye (Evans Blue) was introduced into the glass chamber at specific locations using a micropipette and drying the dye onto the internal glass wall by heating with a heat-gun. This enabled better visualisation and assessment of wash efficacy under various water transfer conditions.

Heating and Pressurising the Wash-Water.

The reservoir was heated to a nominal temperature of 110° C.-120° C. as measured by a thermometer in the heating bed surrounding the PTFE water reservoir, however, the key process parameter was the internal pressure indicated on the analogue gauge. Tests were run at pressures ranging between 35 kPa and 230 kPa (relative to atmospheric pressure).

Performing Sequences of Valve-Openings to Transfer Wash-Water Under Pressure into the Collection Chamber.

The vacuum line solenoid valve and the pure water line solenoid valve were connected to a custom-built electronic control unit based on an Arduino microcontroller interfaced to a PC. Valve open/close commands and their relative timings were dictated using the Arduino software and compiler. The water-transfer sequences can commence with an evacuation of the glass chamber to ~80 mbar by opening the solenoid valve on the vacuum line for 2-5 seconds. The vacuum valve was then closed and 1-5 seconds later a number of short water-transfer valve (Gemü-52) openings were effected.

For reservoir pressures under ~75 kPa, a wash cycle was made up of two separate sequences, starting with a priming sequence comprising two or three openings of 60-90 milliseconds to prime the wash-fluid line and build up an amount of hot condensate water behind the transfer valve, followed by a wash sequence comprising between two and four openings of 30-50 milliseconds in which pulses of hot water and steam moved rapidly into the glass chamber. For reservoir pressures over ~75 kPa a wash cycle was made up of a single sequence of three to six valve openings of 50-75 milliseconds. The water/steam pulses had sufficient momentum to entirely cover all internal surfaces if the driving pressure was over ~35 kPa. The optimum sequencing depends on the initial reservoir pressure and available heating power. In general, water transfers using reservoir pressure over 150 kPa were more consistent and reproducible. The total volume of water transferred into the glass chamber also depends on initial reservoir pressure, which, if higher, leads to more water vapour transfer, though this can be reduced somewhat by using shorter valve openings.

Withdrawing Isotope-Laden Wash Fluid from the Outlet Port of the Collection Chamber Typical volumes of wash-water that had accumulated in the lower region of the glass chamber were 1.5-3.0 mL, depending on the number of water-transfer valve openings that had been used in the wash sequence for a particular test, e.g., 2.0 mL was delivered by a sequence of four 60 millisecond openings with a reservoir pressure of 200 kPa (g). The fluid sat upon a barbed port carrying a silicone tube running into a proximal mini-peristaltic pump, and was able to pass through this port whenever the peristaltic pump is activated.

Example 7: Conjugation of Collected Daughter Radioisotope to Targeting Molecule/Ligands for Use in Radiopharmacy Collected $^{212}$Pb can be conjugated to biomolecules such as antibodies, antibody fragments or peptides through the use of radiometal chelators such as 1,4,7,10-tetraaza-1,4,7,10-tetra(2-carbamoylmethyl) cyclododecane (TCMC). For example; a TCMC functionalised ligand was dissolved in 80 μL of 0.4M NaOAc buffer at pH 5 to a final concentration of 1 mM. The ligand solution was added to 200 MBq of $^{212}$PbCh formulated in 4 mL of 0.4 M NaOAc buffer at pH 5 containing 20% ascorbic acid. The mixture was heated at 70° C. for 30 minutes followed by purification from any unbound $^{212}$Pb or $^{208}$Pb using a Pb specific resin.

The invention claimed is:

1. A $^{220}$Rn emanating tantalum oxide substrate comprising a 228Th oxide layer disposed on and as a part of a surface of the tantalum oxide substrate, where the 228Th oxide layer permits emanation from the surface of the tantalum oxide substrate of gaseous $^{220}$Rn produced by radioactive decay of $^{228}$Th in the $^{228}$Th oxide layer.

2. The tantalum oxide substrate of claim 1, wherein the $^{228}$Th oxide layer is associated with the tantalum oxide substrate such that the emanating gaseous $^{220}$Rn contains less than 0.1% $^{228}$Th as a contaminant.

3. The tantalum oxide substrate of claim 1, wherein the $^{228}$Th oxide layer contains at least 200 MBq of $^{228}$Th.

4. The tantalum oxide substrate of claim 3, wherein the $^{228}$Th oxide layer contains at least 500 MBq of $^{228}$Th.

5. The tantalum oxide substrate of claim 4, wherein the $^{228}$Th oxide layer contains at least 1000 MBq of $^{228}$Th.

6. The tantalum oxide substrate of claim 1, wherein the tantalum oxide substrate has a porosity in volume percentage of total volume of the tantalum oxide substrate of less than 10%.

7. The tantalum oxide substrate of claim 6, wherein the tantalum oxide substrate has a porosity in volume percentage of total volume of the tantalum oxide substrate of less than 5%.

8. The tantalum oxide substrate of claim 1, wherein the $^{228}$Th oxide layer has an average activity of at least 10 MBq per cm$^2$.

9. The tantalum oxide substrate of claim 8, wherein the $^{228}$Th oxide layer has an average activity of at least 100 MBq per cm$^2$.

10. The tantalum oxide substrate of claim 1, wherein at least a portion of $^{228}$Th atoms from the $^{228}$Th oxide layer have exchanged with tantalum atoms in the tantalum oxide substrate and have become immobilized therein.

11. The tantalum oxide substrate of claim 10, wherein the $^{228}$Th oxide layer is formed by applying an aqueous solution of $^{228}$Th to the tantalum oxide substrate and heating the aqueous solution and tantalum oxide substrate to convert the $^{228}$Th in aqueous solution to $^{228}$Th oxide.

12. The tantalum oxide substrate of claim 11, wherein the aqueous solution of $^{228}$Th is $^{228}$Th nitrate.

13. The tantalum oxide substrate of claim 1, wherein the substrate has a substantially planar surface on which the $^{228}$Th oxide layer is disposed.

14. A $^{220}$Rn emanating tantalum oxide substrate comprising a $^{228}$Th oxide layer, containing at least 200 MBq of $^{228}$Th, disposed on and as a part of a surface of the tantalum oxide substrate, where the $^{228}$Th oxide layer permits emanation from the surface of the tantalum oxide substrate of gaseous $^{22}$Rn produced by radioactive decay of $^{228}$Th in the $^{228}$Th oxide layer, and the $^{228}$Th oxide layer is associated with the tantalum oxide substrate through $^{228}$Th migration into the tantalum oxide substrate such that the emanating gaseous $^{220}$Rn contains less than 0.1% $^{228}$Th as a contaminant.

15. The tantalum oxide substrate of claim 14, wherein the $^{228}$Th oxide layer contains at least 500 MBq of $^{228}$Th.

16. The tantalum oxide substrate of claim 15, wherein the $^{228}$Th oxide layer contains at least 1000 MBq of $^{228}$Th.

17. The tantalum oxide substrate of claim 14, wherein the tantalum oxide substrate has a porosity in volume percentage of total volume of the tantalum oxide substrate of less than 10%.

18. The tantalum oxide substrate of claim 14, wherein the $^{228}$Th oxide layer has an average activity of at least 10 MBq per cm$^2$.

19. The tantalum oxide substrate of claim 18, wherein the $^{228}$Th oxide layer has an average activity of at least 100 MBq per cm$^2$.

20. The tantalum oxide substrate of claim 14, wherein the $^{228}$Th oxide layer is formed by applying an aqueous solution of $^{228}$Th to the tantalum oxide substrate and heating the aqueous solution and tantalum oxide substrate to convert the $^{228}$Th in aqueous solution to $^{228}$Th oxide.

21. The tantalum oxide substrate of claim 14, wherein the substrate has a substantially planar surface on which the $^{228}$Th oxide layer is disposed.

22. The tantalum oxide substrate of claim 1, wherein the $^{228}$Th oxide layer is immobilized on the surface of the tantalum oxide substrate.

* * * * *